United States Patent
Choo et al.

(10) Patent No.: US 7,851,216 B2
(45) Date of Patent: Dec. 14, 2010

(54) METHODS AND COMPOSITIONS FOR LINKING BINDING DOMAINS IN NUCLEIC ACID BINDING PROTEINS

(75) Inventors: Yen Choo, Cambridge (GB); Aaron Klug, Cambridge (GB); Michael Moore, Bucks (GB)

(73) Assignee: Gendaq, Ltd., London (GB)

( * ) Notice: Subject to any disclaimer, the term of this patent is extended or adjusted under 35 U.S.C. 154(b) by 1342 days.

(21) Appl. No.: 10/198,677

(22) Filed: Jul. 17, 2002

(65) Prior Publication Data

US 2003/0119023 A1 Jun. 26, 2003

(51) Int. Cl.
C07H 21/04 (2006.01)
C12N 15/00 (2006.01)
C12N 5/00 (2006.01)
A61K 48/00 (2006.01)

(52) U.S. Cl. .................. 435/325; 536/23.1; 536/23.4; 435/320.1; 514/44 R

(58) Field of Classification Search .................. None
See application file for complete search history.

(56) References Cited

U.S. PATENT DOCUMENTS

| | | |
|---|---|---|
| 4,990,607 A | 2/1991 | Katagiri et al. |
| 5,096,814 A | 3/1992 | Aivasidis et al. |
| 5,096,815 A | 3/1992 | Ladner et al. |
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid et al. |
| 5,350,840 A | 9/1994 | Call et al. |
| 5,356,802 A | 10/1994 | Chandrasegaran |
| 5,376,530 A | 12/1994 | De The et al. |
| 5,403,484 A | 4/1995 | Ladner |
| 5,436,150 A | 7/1995 | Chandrasegaran |
| 5,487,994 A | 1/1996 | Chandrasegaran |
| 5,498,530 A | 3/1996 | Schatz et al. |
| 5,578,483 A | 11/1996 | Evans |
| 5,597,693 A | 1/1997 | Evans et al. |
| 5,639,592 A | 6/1997 | Evans et al. |
| 5,674,738 A | 10/1997 | Abramson et al. |
| 5,702,914 A | 12/1997 | Evans et al. |
| 5,789,538 A | 8/1998 | Rebar et al. |
| 5,792,640 A | 8/1998 | Chandrasegaran |
| 5,869,618 A | 2/1999 | Lippman et al. |
| 5,871,902 A | 2/1999 | Weininger et al. |
| 5,871,907 A | 2/1999 | Winter et al. |
| 5,916,794 A | 6/1999 | Chandrasegaran |
| 5,939,538 A | 8/1999 | Leavitt et al. |
| 5,972,615 A | 10/1999 | An et al. |
| 6,001,885 A | 12/1999 | Vega et al. |
| 6,007,988 A | 12/1999 | Choo et al. |
| 6,013,453 A | 1/2000 | Choo et al. |
| 6,110,747 A | 8/2000 | Blaschuk et al. |
| 6,140,081 A | 10/2000 | Barbas |
| 6,140,466 A | 10/2000 | Barbas, III et al. |
| 6,242,568 B1 | 6/2001 | Barbas, III et al. |
| 6,453,242 B1 | 9/2002 | Eisenberg et al. |
| 6,479,626 B1 | 11/2002 | Kim et al. |
| 6,534,261 B1 | 3/2003 | Cox, III et al. |
| 6,610,512 B1 | 8/2003 | Barbas |
| 6,903,185 B2 | 6/2005 | Kim et al. |
| 2002/0165356 A1 | 11/2002 | Barbas, III et al. |
| 2002/0168714 A1 | 11/2002 | Barbas, III et al. |
| 2002/0173006 A1 | 11/2002 | Kim et al. |
| 2003/0037355 A1 | 2/2003 | Barbas, III et al. |
| 2003/0059767 A1 | 3/2003 | Barbas, III et al. |
| 2003/0186841 A1 | 10/2003 | Barbas, III et al. |
| 2005/0202498 A1 | 9/2005 | Kim et al. |

FOREIGN PATENT DOCUMENTS

| | | |
|---|---|---|
| EP | 0 875 567 A2 | 11/1998 |
| WO | WO 95/19431 A1 | 7/1995 |
| WO | WO 96/06110 | 2/1996 |
| WO | WO 96/06166 A1 | 2/1996 |
| WO | WO 96/11267 | 4/1996 |

(Continued)

OTHER PUBLICATIONS

Greisman et al. A general strategy for selecting high-affinity zinc finger proteins for diverse DNA target sites. Science, vol. 275, pp. 657-661, 1997.*
Liu et al., "Design of polydactyl zinc-finger proteins for the unique addressing within complex genomes", *PNAS* USA (1997), 94(11): 5525-5530.
Moore et al, "Design of polyzinc finger peptides with structured linkers", *PNAS* USA (2001), 98 (4): 1432-1436.
Moore et al, "Improved DNA binding specificity from polyzinc finger peptides by using strings of two-finger units", *PNAS* USA (2001), 98 (4): 1437-1441.
Nolte et al., "Differing roles for zinc fingers in DNA recognition: Structure of a six-finger transcription factor IIIA complex", *PNAS* USA (1998), 95: 2938-2943.
Pomerantz et al., "Structure-based design of transcription factors," *Science* (1995) 267:93-96.

(Continued)

*Primary Examiner*—Jennifer Dunston
(74) *Attorney, Agent, or Firm*—Robins & Pasternak LLP

(57) ABSTRACT

We describe a method of producing a modified nucleic acid binding polypeptide, the method comprising the steps of: (a) providing a nucleic acid binding polypeptide comprising a plurality of nucleic acid binding modules; (b) selecting a first binding domain consisting of one or two contiguous nucleic acid binding modules; (c) selecting a second binding domain consisting of one or two contiguous nucleic acid binding modules; and (d) introducing a flexible linker sequence to link the first and second binding domains, the flexible linker sequence comprising five or more amino acid residues. Use of structured linkers, alone or in combination with flexible linkers, is also disclosed.

11 Claims, 27 Drawing Sheets

FOREIGN PATENT DOCUMENTS

| | | |
|---|---|---|
| WO | WO 96/20951 A1 | 7/1996 |
| WO | WO 96/32475 A2 | 10/1996 |
| WO | WO 97/27212 | 7/1997 |
| WO | WO 97/27213 | 7/1997 |
| WO | WO 9724137 A1 * | 7/1997 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 99/36553 | 7/1999 |
| WO | WO 99/41371 | 8/1999 |
| WO | WO 99/45132 A1 | 9/1999 |
| WO | WO 99/47656 A2 | 9/1999 |
| WO | WO 99/48909 | 9/1999 |
| WO | WO 00/27878 A1 | 5/2000 |
| WO | WO 01/53480 A1 | 7/2001 |

OTHER PUBLICATIONS

Pomerantz et al., "Structure-based design of a dimeric zinc finger protein" Biochemistry (1998) 37(4):965-970.

Rebar et al., "Induction of angiogenesis in a mouse model using engineered transcription factors", Nature Medicine (2002) 8:1427-1432.

Segal et al., "Toward controlling gene expression at will: Selection and design of zinc finger domains recognizing each of the 5'-GNN-3' DNA target sequences", PNAS USA (1999), 96 (6): 2758-63.

Smith et al., "A detailed study of the substrate specificity of a chimeric restriction enzyme", Nucleic Acids Research (1999) 27(2):674-681.

Takatsuji et al., "Target-sequence recognition by separate-type $Cys_2$/$His_2$ zinc finger proteins in plants", J. Biol. Chem. (1996), 271: 23368-23373.

Verschueren et al., "SIP1, a novel zinc finger/homeodomain repressor, interacts with Smad protein and binds to 5'-CACCT sequences in candidate target genes," J. Biol. Chem. (1999) 274(29):20489-20498.

Agarwal et al., "Stimulation of Transcript Elongation Requires Both the Zinc Finger and RNA Polymerase II Binding Domains of Human TFIIS," Biochemistry 30(31): 7842-7851 (1991).

Antao et al., "A Thermodynamic Study of Unusually Stable RNA and DNA Hairpins," Nuc. Acids. Res. 19(21): 5901-5905 (1991).

Barbas, C.F. "Recent Advances in Phage Display," Curr. Opin. Biotech. 4: 526-530 (1993).

Barbas et al., "Assembly of Combinatorial Antibody Libraries on Phage Surfaces: The Gene III Site," PNAS 88: 7978-7982 (1991).

Barbas et al., "Semisynthetic Combinatorial Antibody Libraries: A Chemical Solution to the Diversity Problem," PNAS 89: 4457-4461 (1992).

Bellefroid et al., "Clustered Organization of Homologous Krab Zinc-Finger Genes With Enhanced Expressoin in Human T Lymphoid Cells," Embo J. 12(4): 1363-1374 (1993).

Berg, J.M., "DNA Binding Specificity of Steroid Receptors," Cell 57: 1065-1068 (1989).

Berg, J.M., "SP1 and the Subfamily of Zinc-Finger Proteins With Guanine-Rich Binding Sites," PNAS 89: 11109-11110 (1992).

Berg et al., "The Galvanization of Biology: A Growing Appreciation for the Roles of Zinc," Science 271: 1081-1085 (1996).

Berg, J.M., "Letting Your Fingers Do the Walking," Nature Biotechnology 15: 323 (1997).

Bergqvist et al., "Loss of DNA-Binding and New Transcriptiional Trans-Activiation Function in Polyomavirus Large T—Antigen With Mutation of Zinc Finger Motif," Nature Biotechnology 18(9): 2715-2720 (1990).

Blaese et al., "Vectors in Cancer Therapy: How Will They Deliver?" Cancer Gene Therapy 2(4): 291-297 (1995).

Caponigro et al., "Transdominant Genetic Analysis of a Growth Control Pathway," PNAS 95: 7508-7513 (1998).

Celenza et al., "A Yeast Gene that is Essential for Release from Glucose Repression Encodes a Protein Kinase," Science 233: 1175-1180 (1986).

Cheng et al., "Identification of Potential Target Genes for ADRLP Through Characterization of Essential Nucleotides in UAS1," Mol. Cellular Biol. 14(6): 3842-3852 (1994).

Cheng et al., "A Single Amino Acid Subsitutton in Zinc Finger 2 of ADRLP Changes its Binding Specificity at Two Positions in UAS1," J. Mol. Boil. 251: 1-8 (1995).

Choo et al., "Designing DNA-Binding Proteins on the Surface of Filamentous Phage," Curr. Opin. Biotechnology 6: 431-436 (1995).

Choo et al., "Physical Basis of Protein-DNA Recognition Code," Curr. Opin. Struct. Biol. 7(1): 117-125 (1997).

Choo et al., "Promoter-Specific Activiation of Gene Expression Directed by Bacteriophage-Selected Zinc Fingers," J. Mol. Biol. 273: 525-532 (1997).

Choo et al., "In Vivo Repression by a Site-Specific DNA-Binding Protein Deisned Against an Onogenic Sequence," Nature 372: 642-645 (1994).

Choo et al., "All Wrapped Up," Nature Struct. Biol. 5(4): 253-255 (1998).

Choo, Y., "Recognition of DNA Methylation by Zinc Fingers," Nature Struct. Biol. 5(4): 264-265 (1998).

Choo, Y., "End Effects in DNA Recognition Code," Nuc. Acids. Res. 26(2): 554-557 (1998).

Choo et al., "A Role in DNA-Binding for the Linker Sequences of the First Three Zinc Fingers of TFIIIA" Nuc. Acids Res. 21(15): 3341-3346 (1993).

Choo et al., "Toward a Code for the Interactions of Zinc Fingers With DNA: Selection of Randomized Fingers Displayed on Phage," PNAS 91: 11163-11167 (1994).

Choo et al., "Selection of DNA Binding Sites for Zinc Fingers Using Randomized DNAS Reveals Coded Interactions," PNAS 91: 11168-11172 (1994).

Clarke et al., "Zinc Fingers in Caenorhabditis elegans: Finding Familiies and Probing Patheways," Science 282: 2018-2022 (1998).

Corbi et al., "Synthesis of a New Zinc Finger Peptide: Comparison of Its "Code" Deduced and "Casting" Derived Binding Sites," FEBS Letters 417: 71-74 (1997).

Crozatier et al., "Single Amino Acid Exchanges in Separate Domains of the Drosophilia Serendipity Zinc Finger Protein Cause Embroyonic and Sex Biased Lethality," Genetics 131: 905-916 (1992).

Debs et al., "Regulation of Gene Expression in Vivo by Liposome-Mediated Delivery of a Purified Transcription Factor," J. Biological Chemistry 265(18): 10189-10192 (1990).

Desjarlais et al., "Redesigning the DNA-Binding Specificity of a Zinc Finger Protein: A Data Base-Guided Approach," Proteins: Structure, Function, and Genetics 13(2): 272 (1992).

Desjarlais et al., "Toward Rules Relating Zinc Finger Protein Sequences and DNA Binding Site Preferences," Proc Natl Acad Sci USA 89:7345-7349 (1992).

Desjarlais et al., "Use of a Zinc-Finger Consensus Sequences Framework and Specificity Rules to Design Specific DNA Binding, Proteins" PNAS 90: 2256-2260 (1993).

Desjarlais et al., "Length-Encoded Multiplex Binding Site Determination: Application to Zinc Finger Proteins," PNAS 91: 11099-11103 (1994).

Dibello et al., "The Drosophila Broad-Complex Encodes a Family of Related Proteins Containing Zinc Fingers," Genetics 129: 385-397 (1991).

Elrod-Erickson et al., "High-Resolution Structures of Variant ZIF268-DNA Complexes: Implications for Understanding Zinc Finger-DNA Recognition," Structure 6(4): 451-464 (1998).

Fairall et al., "The Crystal Structure of a Two Zinc-Finger Peptide Reveals an Extension to the Rules for Zinc-Finger/ DNA Recognition," Nature 366: 483-487 (1993).

Frankel et al., "Fingering Too Many Proteins," Cell 53: 675 (1988).

Friesen et al., "Phage Display of RNA Binding Zinc Fingers From Transcription Factor IIA," J. Biological Chem. 272(17): 10994-10997 (1997).

Friesen et al., "Specific RNA Binding Proteins Constructed From Zinc Fingers," Nature Structural Biology 5(7): 543-546 (1998).

Gogos et al., "Recognition of Diverse Sequences by Class 1 Zinc Fingers: Asymmetries and Indirect Effects on Specificty in the Interaction Between CF2II and A+T-Rich Sequences Elements," PNAS 93(5): 2159-2164 (1996).
Gossen et al.., "Tight Control of Gene Expression in Mammalian Cells by Tetracycline-Responsive Promoter,"PNAS 89:5547-5551 (1992).
Hamilton et al., "High Affinity Binding Sites for the Wilms' Tumor Suppressor Protein WTI," Nuc. Acids. Res. 23(2): 277-284 (1995).
Hamilton et al., "Comparison of the DNA Binding Characteristics of the Related Zinc Finger Proteins WT1 and EGR1" Biochemistry 37: 2051-2058 (1998).
Hanas et al., "Internal Deletion Mutants of *Xenopus* Transcription Factor IIIA," Nuc. Acids. Res. 17(23): 9861-9870 (1989).
Hayes et al., "Locations of Contacts Between Individual Zinc Fingers *Xenopus laevis* Transcription Factor IIIA and the Internal Control Region of a 5S RNA Gene," Biochemistry 31: 11600-11605 (1992).
Heinzel et al., "A Complex Containing N-CoR, MSin3 and Histone Deacetylese Medates Transcriptional Repression," Nature 387: 43-48 (1997).
Hirst et al., "Discrimination of DNA Response Elements for Thyroid Hormone and Estrogen is Dependent on Dimerization of Receptor DNA Binding Domains," PNAS 89: 5527-5531 (1992).
Hoffman et al., "Structures of DNA-Binding Mutant Zinc Finger Domains: Implications for DNA Binding," Protein Science 2: 951-965 (1993).
Isalan et al., "Synergy Between Adjacent Zinc Fingers in Sequence-Specific DNA Recognition," PNAS 94(11): 5617-5621 (1997).
Isalan et al., "Comprehensive DNA Recogniition Through Concerted Interactions From Adjacent Zinc Fingers," *Biochemistry* 37:12026-12033 (1998).
Jacobs, G. H., "Determination of the Base Recognition Positions of Zinc Fingers From Sequence Analysis," EMBO J. 11(12): 4507-4517 (1992).
Jamieson et al., "A Zinc Finger Directory for High-Affinity DNA Recognition," PNAS 93: 12834-12839 (1996).
Jamieson et al., "In Vitro Selection of Zinc Fingers With Altered DNA-Binding Specificity," *Biochemistry* 33:5689-5695 (1994).
Julian et al., "Replacement of H1S23 by CYS in a Zinc Finger of HIV-INCP7 Led to a Change in 1H NMR-Derived 3D Structure and to a Loss of Biological Activity," FEBS Letters 331(1,2): 43-48 (1993).
Kamiuchi et al., "New Multi Zinc Finger Protein: Biosynthetic Design and Characteristics of DNA Recognition," Nucleic Acids Symposium Series 37: 153-154 (1997).
Kang et al., "Zinc Finger Proteins as Designer Transcription Factors,"*J.Biol Chem* 245(12):8742-8748 (2000).
Kim et al., "Serine at Position 2 in the DNA Recognition Helix of a CYS2-HIS2 Zinc Finger Peptide is Not, in General Responsible for Base Recognition," J. Mol. Biol. 252: 1-5 (1995).
Kim et al., "Site-Specific Cleavage of DNA-RNA Hybrids by Zinc Finger/FOKI/Cleavage Domain Fusions," Gene 203: 43-49 (1997).
Kim et al., "A 2.2 A° Resolution Crystal Structure of a Designed Zinc Finger Protein Bound to DNA," Nat. Struct. Biol. 3(11): 940-945 (1996).
Kim et al., "Transcriptional Repression by Zinc Finger Peptides. Exploring the Potential for Applications in Gene Therapy" J. Biol. Chem. 272: 29795-29800 (1997).
Kinzler et al., "The GLI Gene is Member of the Kruppel Family of Zinc Finger Proteins," Nature 332: 371-374 (1988).
Klug, A. "Gene Regulatory Proteins and Their Interaction With DNA," Ann. NY Acad. Sci. 758: 143-160 (1995).
Klug et al., "Protein Motifs 5: Zinc Fingers," FASEB J. 9: 597-604 (1995).
Klug, "Zinc Finger Peptides for the Regulation of Gene Expression," J. Mol. Biol. 293: 215-218 (1999).
Kothekar, "Computer Simulation of Zinc Finger Motif From Cellular Nucleic Acid Binding Proteins and Their Interaction With Consensus DNA Sequences," FEBS Letters 274(1,2): 217-222 (1990).
Kriwacki et al., "Sequence-Specific Recognition of DNA by Zinc Finger Peptides Derived From the Transcription Factor SP-I," PNAS 89: 9759-9763 (1992).

Kudla et al., "The Regulatory Gene Area Mediating Nitrogen Metabolite R in *Aspergillus nidulans* Mutations Affecting Specificity of Gene Activation Alter a Loop Residue of Putative Zinc Finger," EMBO J. 9(5): 1355-1364 (1990).
Laird-Offringa et al., "RNA-Binding Proteins Tamed," Nat. Structural Biol. 5(8): 665-668 (1998).
Mandel-Gutfreund et al., "Quantitative Parameters for Amino Acid-Base Interaction: Implication for Predication of Protein-DNA Binding Sites," Nuc. Acids Res. 26(10): 2306-2312 (1998).
Margolin et al., "Kruppel-Associated Boxes are Potent Transcriptional Repression Domains," PNAS 91: 4509-4513 (1994).
Mizushima et al., "PEF-BOS, a Powerful Mammilian Expression Vector," Nuc. Acids. Res. 18(17): 5322 (1990).
Nakagama et al, "Sequence and Structural Requirements for High-Affinity DNA Binding by the WTI Gene Product," Molecular and Cellular Biology 15(3): 1489-1498 (1995).
Nardelli et al., "Zinc Finger-DNA Recognition: Analysis of Base Specificity by Site-Directed Mutagenesis," Nucleic Acids Research 20(16): 4137-4144 (1992).
Nardelli et al., "Base Sequence Discrimination by Zinc-Finger DNA-Binding Domains," Nature 349: 175-178 (1991).
Nekludova et al., "Distinctive DNA Conformation With Enlarged Major Groove is Found in ZN-Finger-DNA and Other Protein-DNA Complexes," PNAS 91: 6948-6952 (1994).
Orkin et al., "Report and Recommendations of the Panel to Assess the NIH Investment in Research on Gene Therapy," (Dec. 7, 1995).
Pabo et al., "Systematic Analysis of Possible Hydrogen Bonds Between Amino Acid Side Chains and B-Form DNA," J. Biomolecular Struct. Dynamic 1: 1039-1049 (1983).
Pabo et al., Protein-DNA Recognition, Ann. Rev. Biochem. 53: 293-321 (1984).
Pabo, C.O., "Transcription Factors: Structural Families and Principles of DNA Recognition," Ann. Rev. Biochem. 61: 1053-1095 (1992).
Pavletich et al., "Crystal Structure of a Five-Finger GLI-DNA Complex: New Perspectives on Zinc Fingers," Science, 261: 1701-1707 (1993).
Pavletich et al., "Zinc Finger-DNA Recognition: Crystal Structure of a ZIF268-DNA Complex At 2.1A," Science 252: 809-817 (1991).
Pengue et al., "Repression of Transcriptional Activity at a Distance by the Evolutionarily Conserved Krab Domain Present in a Subfamily of Zinc Finger Proteins," Nuc. Acids Res. 22(15): 2908-2914 (1994).
Pengue et al., "Transcriptional Silencing of Human Immunodeficiency Virus Type 1 Long Terminal Repeat-Driven Gene Expression by the Kruppel-Associated Box Repressor Domain Targeted to the Transactivating Response Element," J. Virology 69(10): 6577-6580 (1995).
Pengue et al., "Kruppel-Associated Box-Mediated Repression of RNA Polymerase II Promoters is Influenced by the Arrangement of Basal Promoter Elements," PNAS 93: 1015-1020 (1996).
Pomerantz et al., "Analysis of Homeodomain Function by Structure-Based Design of a Transcription Factor," PNAS 92: 9752-9756 (1995).
Qian et al., "Two-Dimensional NMR Studies of the Zinc Finger Motif: Solution Structures and Dynamics of Mutant ZFY Domains Containing Aromatic Substitutions in the Hydrophobic Core," Biochemistry 31: 7463-7476 (1992).
Quigley et al., "Complete Androgen Insensitivity Due to Deletion of Exon C of the Androgen Receptor Gene Highlights the Functional Importance of the Second Zinc Finger of the Androgen Receptor In Vivo," Molecular Endocrinology 6(7): 1103-1112 (1992).
Rauscher et al., "Binding of the Wilms' Tumor Locus Zinc Finger Protein to the EGR-I Consensus Sequence," Science 250: 1259-1262 (1990).
Ray et al., "Repressor to Activator Switch by Mutations in the First ZN Finger of the Glucocorticoid Receptor: is Direct DNA Binding Necessary?" PNAS 88: 7086-7090 (1991).
Rebar et al., "Phage Display Methods for Selecting Zinc Finger Proteins With Novel DNA-Binding Specificities," Methods in Enzymology 267: 129-149 (1996).
Rebar et al, "Zinc Finger Phage: Affinity Selection of Fingers With New DNA-Binding Specifities," Science 263: 671-673 (1994).

Reith et al, "Cloning of the Major Histocompatibility Complex Class II Promoter Binding Protein Affected in a Hereditary Defect in Class II Gene Regulation," PNAS 86: 4200-4204 (1989).

Rhodes et al., "Zinc Fingers: They Play a Key Part in Regulating the Activity of Genes in Many Species, From Yeast to Humans. Fewer Than 10 Years Ago No On Knew They Existed." Scientific American 268:56-65 (1993).

Rice et al., "Inhibitors of HIV Nucleocapsid Protein Zinc Fingers As Candidates for the Treatment of AIDS," Science 270: 1194-1197 (1995).

Rivera et al., "A Humanized System for Pharmacologic Control of Gene Expression," Nature Medicine 2(9): 1028-1032 (1996).

Rollins et al., "Role of TFIIIA Zinc Fingers In Vivo: Analysis of Single-Finger Function in Developing *Xenopus* Embryos," Molecular Cellular Biology 13(8): 4776-4783 (1993).

Saleh et al., "A Novel Zinc Finger Gene on Human Chromosome 1 QTER That is Alternatively Spliced in Human Tissues and Cell Lines," American Journal of Human Genetics 52: 192-203 (1993).

Shi et al., "Specific DNA-RNA Hybrid Binding by Zinc Finger Proteins," Science 268: 282-284 (1995).

Shi et al., "DNA Unwinding Induced by Zinc Finger Protein Binding," Biochemistry 35: 3845-3848 (1996).

Shi et al., "A Direct Comparison of the Properties of Natural and Designed Finger Proteins," Chem. & Biol. 2(2): 83-89 (1995).

Singh et al., "Molecular Cloning of an Enhancer Binding Protein: Isolation by Screening of an Expression Library With a Recognition Site DNA," Cell 52: 415-423 (1988).

Skerka et al., "Coordinate Expression and Distinct DNA-Binding Characteristics of the Four EGR-Zinc Finger Proteins in Jurkat T Lymphocytes," Immunobiology 198: 179-191 (1997).

South et al., "The Nucleocapsid Protein Isolated From HIV-1 Particles Binds Zinc and Forms Retroviral-Type Zinc Fingers," Biochemistry 29: 7786-7789 (1990).

Suzuki et al., "Stereochemical Basis of DNA Recognition by ZN Fingers," Nuc. Acids Res. 22(16): 3397-3405 (1994).

Suzuki et al., "DNA Recognition Code of Transcriptional Factors in the Helix-Turn-Helix, Probe Helix, Hormone Receptor, and Zinc Finger Families," PNAS 91: 12357-12361 (1994).

Swirnoff et al, "DNA-Binding Specificity of NGFI-A and Related Zinc Finger Transcriptional Factors," Mol. Cell. Biol. 15(14): 2275-2287 (1995).

Taylor et al., "Designing Zinc-Finger ADRI Mutants With Altered Specificity of DNA Binding to T in UASI Sequences," Biochemistry 34: 3222-3230 (1995).

Thiesen et al., "Amino Acid Substitutions in the SPI Zinc Finger Domain Alter the DNA Binding Affinity to Cognate SP1 Target Site," Biochem. Biophys. Res. Communications 175(1): 333-338 (1991).

Thiesen et al., "Determination of DNA Binding Specificities of Mutated Zinc Finger Domains," FEBS letters 283(1): 23-26 (1991).

Thukral et al., "Localization of a Minimal Binding Domain and Activation Regions in Yeast Regulatory Protein ADRI1," Molecular Cellular Biology 9(6): 2360-2369 (1989).

Thukral et al., "Two Monomers of Yeast Transcription Factor ADR1 Bind a Paldromic Sequence Symmetrically to Activate ADH2 Expression," Molecular Cellular Biol. 11(3): 1566-1577 (1991).

Thukral et al., "Mutations in the Zinc Fingers of ADR1 That Change the Specificity of DNA Binding and Transactivation," Mol. Cell. Biol. 12(6): 2784-2792 (1992).

Thukral et al., "Alanine Scanning Site-Directed Mutagenesis of the Zinc Fingers of Transcription Factor ADR1: Residues That Contact DNA and That Transactivate," PNAS 88: 9188-9192 (1991).

Vortkamp et al., "Identification of Optimized Target Sequences for the GL 13 Zinc Finger Protein," DNA Cell Biol. 14(7): 629-634 (1995).

Wang et al., "Dimerization of Zinc Fingers Mediated by Peptides Evolved In Vitro From Random Sequences," PNAS 96: 9568-9573 (1999).

Webster et al., "Conversion of the E1A CYS4 Zinc Finger to a Nonfunctional HIS2, CYS2 Zinc Finger by a Single Point Mutation," PNAS 88: 9989-9993 (1999).

Whyatt et al., "The Two Zinc Finger-Like Domains of GATA-1 Have Different DNA Binding Specificities," EMBO J. 12(13): 4993-5005 (1993).

Wilson et al., "In Vivo Mutational Analysis of the NGFI-A Zinc Fingers," J. Biol. Chem. 267(6): 3718-3724 (1992).

Witzgall et al., "The Kruppel-Associated Box-A (KRAB-A) Domain of Zinc Finger Proteins Mediates Transcriptional Repression," PNAS 91: 4514-4518 (1994).

Wolfe et al., "Analysis of Zinc Fingers Optimized Via Phage Display: Evaluating the Utility of a Recognition Code," J. Mol. Biol. 285: 1917-1934 (1999).

Wright et al., "Expression of a Zinc Finger Gene in HTLV-I and HTLV-II Transformed Cell," Science 248:588-591 (1990).

Wu et al., "Building Zinc Fingers by Selection: Toward a Therapeutic Application," PNAS 92: 344-348(1995).

Yang et al., "Surface Plasmon Resonance Based Kinetic Studies of Zinc Finger-DNA Interaction," J. Immunol. Methods 183: 175-182 (1995).

Yu et al., "A Hairpin Ribozyme Inhibits Expression of Diverse Strains of Human Immunodeficiency Virus Type 1," PNAS 90: 6340-6344 (1993).

Search of Swissprot. Data Base Performed CA Aug. 2000.

* cited by examiner

ZIF-GAC

SEQ ID NO: 21

```
1/1                                    31/11
ATG GCA GAA CGC CCG TAT GCT TGC CCT GTC GAG TCC TGC GAT CGC CGC TTT TCT CGC TCG
 M   A   E   R   P   Y   A   C   P   V   E   S   C   D   R   R   F   S   R   S
61/21                                  91/31
GAT GAG CTT ACC CGC CAT ATC CGC ATC CAC ACA GGC CAG AAG CCC TTC CAG TGT CGA ATC
 D   E   L   T   R   H   I   R   I   H   T   G   Q   K   P   F   Q   C   R   I
121/41                                 151/51
TGC ATG CGT AAC TTC AGT CGT AGT GAC CAC CTT ACC ACC CAC ATC CGC ACC CAC ACA GGC
 C   M   R   N   F   S   R   S   D   H   L   T   T   H   I   R   T   H   T   G
181/61                                 211/71
GAG AAG CCT TTT GCC TGT GAC ATT TGT GGG AGG AAG TTT GCC AGG AGT GAT GAA CGC AAG
 E   K   P   F   A   C   D   I   C   G   R   K   F   A   R   S   D   E   R   K
241/81                                 271/91
AGG CAT ACC AAA ATC CAT TTA AGA CAG AAG GAC GGC GAA CGG CCG TAT GCT TGC CCT GTC
 R   H   T   K   I   H   L   R   Q   K   D   G   E   R   P   Y   A   C   P   V
301/101                                331/111
GAG TCC TGC GAT CGC CGC TTT TCT CGC TCG GAT GAG CTT ACC CGC CAT ATC CGC ATC CAC
 E   S   C   D   R   R   F   S   R   S   D   E   L   T   R   H   I   R   I   H
361/121                                391/131
ACA GGC CAG AAG CCC TTC CAG TGT CGA ATC TGC ATG CGT AAC TTC AGT GAT AGA AGC AAT
 T   G   Q   K   P   F   Q   C   R   I   C   M   R   N   F   S   D   R   S   N
421/141                                451/151
CTT GAA CGT CAC ACG AGG ACC CAC ACA GGC GAG AAG CCT TTT GCC TGT GAC ATT TGT GGG
 L   E   R   H   T   R   T   H   T   G   E   K   P   F   A   C   D   I   C   G
481/161                                511/171
AGG AAG TTT GCC AGG AGT GAT GAA CGC AAG AGG CAT ACC AAA ATC CAT TTA AGA CAG AAG
 R   K   F   A   R   S   D   E   R   K   R   H   T   K   I   H   L   R   Q   K
541/181
GAC
 D
```

FIG. 2

3x2F ZGS

SEQ ID NO: 22

```
1/1                                     31/11
ATG GCA GAA CGC CCG TAT GCT TGC CCT GTC GAG TCC TGC GAT CGC CGC TTT TCT CGC TCG
 M   A   E   R   P   Y   A   C   P   V   E   S   C   D   R   R   F   S   R   S
61/21                                   91/31
GAT GAG CTT ACC CGC CAT ATC CGC ATC CAC ACA GGC CAG AAG CCC TTC CAG TGT CGA ATC
 D   E   L   T   R   H   I   R   I   H   T   G   Q   K   P   F   Q   C   R   I
121/41                                  151/51
TGC ATG CGT AAC TTC AGT CGT AGT GAC CAC CTT ACC ACC CAC ATC CGC ACC CAC ACA GGT
 C   M   R   N   F   S   R   S   D   H   L   T   T   H   I   R   T   H   T   G
181/61                                  211/71
GGC GAG AAG CCT TTT GCC TGT GAC ATT TGT GGG AGG AAG TTT GCC AGG AGT GAT GAA CGC
 G   E   K   P   F   A   C   D   I   C   G   R   K   F   A   R   S   D   E   R
241/81                                  271/91
AAG AGG CAT ACC AAA ATC CAT ACC GGT GAA CGG CCG TAT GCT TGC CCT GTC GAG TCC TGC
 K   R   H   T   K   I   H   T   G   E   R   P   Y   A   C   P   V   E   S   C
301/101                                 331/111
GAT CGC CAC TTT TCT CGC TCG GAT GAG CTT ACC CGC CAT ATC CGC ATC CAC ACA GGT GGC
 D   R   H   F   S   R   S   D   E   L   T   R   H   I   R   I   H   T   G   G
361/121                                 391/131
CAG AAG CCC TTC CAG TGT CGA ATC TGC ATG CGT AAC TTC AGT GAT AGA AGC AAT CTT GAA
 Q   K   P   F   Q   C   R   I   C   M   R   N   F   S   D   R   S   N   L   E
421/141                                 451/151
CGT CAC ACG AGG ACC CAC ACA GGC GAG AAG CCT TTT GCC TGT GAC ATT TGT GGG AGG AAG
 R   H   T   R   T   H   T   G   E   K   P   F   A   C   D   I   C   G   R   K
481/161                                 511/171
TTT GCC AGG AGT GAT GAA CGC AAG AGG CAT ACC AAA ATC CAT TTA AGA CAG AAG GAC
 F   A   R   S   D   E   R   K   R   H   T   K   I   H   L   R   Q   K   D
```

FIG. 3

3x2F ZGL

SEQ ID NO: 23

```
1/1                                     31/11
ATG GCA GAA CGC CCG TAT GCT TGC CCT GTC GAG TCC TGC GAT CGC CGC TTT TCT CGC TCG
 M   A   E   R   P   Y   A   C   P   V   E   S   C   D   R   R   F   S   R   S
61/21                                   91/31
GAT GAG CTT ACC CGC CAT ATC CGC ATC CAC ACA GGC CAG AAG CCC TTC CAG TGT CGA ATC
 D   E   L   T   R   H   I   R   I   H   T   G   Q   K   P   F   Q   C   R   I
121/41                                  151/51
TGC ATG CGT AAC TTC AGT CGT AGT GAC CAC CTT ACC ACC CAC ATC CGC ACC CAC ACA GGC
 C   M   R   N   F   S   R   S   D   H   L   T   T   H   I   R   T   H   T   G
181/61                                  211/71
GGT TCT GGC GAG AAG CCT TTT GCC TGT GAC ATT TGT GGG AGG AAG TTT GCC AGG AGT GAT
 G   S   G   E   K   P   F   A   C   D   I   C   G   R   K   F   A   R   S   D
241/81                                  271/91
GAA CGC AAG AGG CAT ACC AAA ATC CAT ACC GGT GAA CGG CCG TAT GCT TGC CCT GTC GAG
 E   R   K   R   H   T   K   I   H   T   G   E   R   P   Y   A   C   P   V   E
301/101                                 331/111
TCC TGC GAT CGC CAC TTT TCT CGC TCG GAT GAG CTT ACC CGC CAT ATC CGC ATC CAC ACA
 S   C   D   R   H   F   S   R   S   D   E   L   T   R   H   I   R   I   H   T
361/121                                 391/131
GGC GGT TCT GGC CAG AAG CCC TTC CAG TGT CGA ATC TGC ATG CGT AAC TTC AGT GAT AGA
 G   G   S   G   Q   K   P   F   Q   C   R   I   C   M   R   N   F   S   D   R
421/141                                 451/151
AGC AAT CTT GAA CGT CAC ACG AGG ACC CAC ACA GGC GAG AAG CCT TTT GCC TGT GAC ATT
 S   N   L   E   R   H   T   R   T   H   T   G   E   K   P   F   A   C   D   I
481/161                                 511/171
TGT GGG AGG AAG TTT GCC AGG AGT GAT GAA CGC AAG AGG CAT ACC AAA ATC CAT TTA AGA
 C   G   R   K   F   A   R   S   D   E   R   K   R   H   T   K   I   H   L   R
541/181
CAG AAG GAC
 Q   K   D
```

FIG. 4

3x2F ZGXL

SEQ ID NO: 24

```
1/1                                           31/11
ATG GCA GAA CGC CCG TAT GCT TGC CCT GTC GAG TCC TGC GAT CGC CGC TTT TCT CGC TCG
 M   A   E   R   P   Y   A   C   P   V   E   S   C   D   R   R   F   S   R   S
61/21                                         91/31
GAT GAG CTT ACC CGC CAT ATC CGC ATC CAC ACA GGC CAG AAG CCC TTC CAG TGT CGA ATC
 D   E   L   T   R   H   I   R   I   H   T   G   Q   K   P   F   Q   C   R   I
121/41                                        151/51
TGC ATG CGT AAC TTC AGT CGT AGT GAC CAC CTT ACC ACC CAC ATC CGC ACC CAC ACA GGC
 C   M   R   N   F   S   R   S   D   H   L   T   T   H   I   R   T   H   T   G
181/61                                        211/71
GGT TCT GGC GGT TCT GGC GAG AAG CCT TTT GCC TGT GAC ATT TGT GGG AGG AAG TTT GCC
 G   S   G   G   S   G   E   K   P   F   A   C   D   I   C   G   R   K   F   A
241/81                                        271/91
AGG AGT GAT GAA CGC AAG AGG CAT ACC AAA ATC CAT ACC GGT GAA CGG CCG TAT GCT TGC
 R   S   D   E   R   K   R   H   T   K   I   H   T   G   E   R   P   Y   A   C
301/101                                       331/111
CCT GTC GAG TCC TGC GAT CGC CAC TTT TCT CGC TCG GAT GAG CTT ACC CGC CAT ATC CGC
 P   V   E   S   C   D   R   H   F   S   R   S   D   E   L   T   R   H   I   R
361/121                                       391/131
ATC CAC ACA GGC GGT TCT GGC GGT TCT GGC CAG AAG CCC TTC CAG TGT CGA ATC TGC ATG
 I   H   T   G   G   S   G   G   S   G   Q   K   P   F   Q   C   R   I   C   M
421/141                                       451/151
CGT AAC TTC AGT GAT AGA AGC AAT CTT GAA CGT CAC ACG AGG ACC CAC ACA GGC GAG AAG
 R   N   F   S   D   R   S   N   L   E   R   H   T   R   T   H   T   G   E   K
481/161                                       511/171
CCT TTT GCC TGT GAC ATT TGT GGG AGG AAG TTT GCC AGG AGT GAT GAA CGC AAG AGG CAT
 P   F   A   C   D   I   C   G   R   K   F   A   R   S   D   E   R   K   R   H
541/181                                       571/191
ACC AAA ATC CAT TTA AGA CAG AAG GAC
 T   K   I   H   L   R   Q   K   D
```

FIG. 5

3x2F ZGSL

SEQ ID NO: 25

```
1/1                                                             31/11
ATG GCA GAA CGC CCG TAT GCT TGC CCT GTC GAG TCC TGC GAT CGC CGC TTT TCT CGC TCG
 M   A   E   R   P   Y   A   C   P   V   E   S   C   D   R   R   F   S   R   S
61/21                                                           91/31
GAT GAG CTT ACC CGC CAT ATC CGC ATC CAC ACA GGC CAG AAG CCC TTC CAG TGT CGA ATC
 D   E   L   T   R   H   I   R   I   H   T   G   Q   K   P   F   Q   C   R   I
121/41                                                          151/51
TGC ATG CGT AAC TTC AGT CGT AGT GAC CAC CTT ACC ACC CAC ATC CGC ACC CAC ACA GGT
 C   M   R   N   F   S   R   S   D   H   L   T   T   H   I   R   T   H   T   G
181/61                                                          211/71
GGC GAG AAG CCT TTT GCC TGT GAC ATT TGT GGG AGG AAG TTT GCC AGG AGT GAT GAA CGC
 G   E   K   P   F   A   C   D   I   C   G   R   K   F   A   R   S   D   E   R
241/81                                                          271/91
AAG AGG CAT ACC AAA ATC CAT ACC GGT GAA CGG CCG TAT GCT TGC CCT GTC GAG TCC TGC
 K   R   H   T   K   I   H   T   G   E   R   P   Y   A   C   P   V   E   S   C
301/101                                                         331/111
GAT CGC CAC TTT TCT CGC TCG GAT GAG CTT ACC CGC CAT ATC CGC ATC CAC ACA GGC GGT
 D   R   H   F   S   R   S   D   E   L   T   R   H   I   R   I   H   T   G   G
361/121                                                         391/131
TCT GGC CAG AAG CCC TTC CAG TGT CGA ATC TGC ATG CGT AAC TTC AGT GAT AGA AGC AAT
 S   G   Q   K   P   F   Q   C   R   I   C   M   R   N   F   S   D   R   S   N
421/141                                                         451/151
CTT GAA CGT CAC ACG AGG ACC CAC ACA GGC GAG AAG CCT TTT GCC TGT GAC ATT TGT GGG
 L   E   R   H   T   R   T   H   T   G   E   K   P   F   A   C   D   I   C   G
481/161                                                         511/171
AGG AAG TTT GCC AGG AGT GAT GAA CGC AAG AGG CAT ACC AAA ATC CAT TTA AGA CAG AAG
 R   K   F   A   R   S   D   E   R   K   R   H   T   K   I   H   L   R   Q   K
541/181
GAC
 D
```

FIG. 6

3x2F ZGLS

SEQ ID NO: 26

```
1/1                                             31/11
ATG GCA GAA CGC CCG TAT GCT TGC CCT GTC GAG TCC TGC GAT CGC CGC TTT TCT CGC TCG
 M   A   E   R   P   Y   A   C   P   V   E   S   C   D   R   R   F   S   R   S
61/21                                           91/31
GAT GAG CTT ACC CGC CAT ATC CGC ATC CAC ACA GGC CAG AAG CCC TTC CAG TGT CGA ATC
 D   E   L   T   R   H   I   R   I   H   T   G   Q   K   P   F   Q   C   R   I
121/41                                          151/51
TGC ATG CGT AAC TTC AGT CGT AGT GAC CAC CTT ACC ACC CAC ATC CGC ACC CAC ACA GGC
 C   M   R   N   F   S   R   S   D   H   L   T   T   H   I   R   T   H   T   G
181/61                                          211/71
GGT TCT GGC GAG AAG CCT TTT GCC TGT GAC ATT TGT GGG AGG AAG TTT GCC AGG AGT GAT
 G   S   G   E   K   P   F   A   C   D   I   C   G   R   K   F   A   R   S   D
241/81                                          271/91
GAA CGC AAG AGG CAT ACC AAA ATC CAT ACC GGT GAA CGG CCG TAT GCT TGC CCT GTC GAG
 E   R   K   R   H   T   K   I   H   T   G   E   R   P   Y   A   C   P   V   E
301/101                                         331/111
TCC TGC GAT CGC CAC TTT TCT CGC TCG GAT GAG CTT ACC CGC CAT ATC CGC ATC CAC ACA
 S   C   D   R   H   F   S   R   S   D   E   L   T   R   H   I   R   I   H   T
361/121                                         391/131
GGT GGC CAG AAG CCC TTC CAG TGT CGA ATC TGC ATG CGT AAC TTC AGT GAT AGA AGC AAT
 G   G   Q   K   P   F   Q   C   R   I   C   M   R   N   F   S   D   R   S   N
421/141                                         451/151
CTT GAA CGT CAC ACG AGG ACC CAC ACA GGC GAG AAG CCT TTT GCC TGT GAC ATT TGT GGG
 L   E   R   H   T   R   T   H   T   G   E   K   P   F   A   C   D   I   C   G
481/161                                         511/171
AGG AAG TTT GCC AGG AGT GAT GAA CGC AAG AGG CAT ACC AAA ATC CAT TTA AGA CAG AAG
 R   K   F   A   R   S   D   E   R   K   R   H   T   K   I   H   L   R   Q   K
541/181
GAC
 D
```

FIG. 7

3x1F ZIF
SEQ ID NO: 27

```
1/1                                        31/11
ATG GCA GAA CGC CCG TAT GCT TGC CCT GTC GAG TCC TGC GAT CGC CGC TTT TCT CGC TCG
 M   A   E   R   P   Y   A   C   P   V   E   S   C   D   R   R   F   S   R   S
61/21                                      91/31
GAT GAG CTT ACC CGC CAT ATC CGC ATC CAC ACA GGT GGC CAG AAG CCC TTC CAG TGT CGA
 D   E   L   T   R   H   I   R   I   H   T   G   G   Q   K   P   F   Q   C   R
121/41                                     151/51
ATC TGC ATG CGT AAC TTC AGT CGT AGT GAC CAC CTT ACC ACC CAC ATC CGC ACC CAC ACA
 I   C   M   R   N   F   S   R   S   D   H   L   T   T   H   I   R   T   H   T
181/61                                     211/71
GGT GGC GAG AAG CCT TTT GCC TGT GAC ATT TGT GGG AGG AAG TTT GCC AGG AGT GAT GAA
 G   G   E   K   P   F   A   C   D   I   C   G   R   K   F   A   R   S   D   E
241/81                                     271/91
CGC AAG AGG CAT ACC AAA ATC CAT TTA AGA CAG AAG GAC
 R   K   R   H   T   K   I   H   L   R   Q   K   D
```

FIG. 8

TFIIIA(F1-4)-ZIF

SEQ ID NO: 53

```
1/1                                             31/11
ATG GGA GAG AAG GCG CTG CCG GTG GTG TAT AAG CGG TAC ATC TGC TCT TTC GCC GAC TGC
 M   G   E   K   A   L   P   V   V   Y   K   R   Y   I   C   S   F   A   D   C
61/21                                           91/31
GGC GCT GCT TAT AAC AAG AAC TGG AAA CTG CAG GCG CAT CTG TGC AAA CAC ACA GGA GAG
 G   A   A   Y   N   K   N   W   K   L   Q   A   H   L   C   K   H   T   G   E
121/41                                          151/51
AAA CCA TTT CCA TGT AAG GAA GAA GGA TGT GAG AAA GGC TTT ACC TCG CTT CAT CAC TTA
 K   P   F   P   C   K   E   E   G   C   E   K   G   F   T   S   L   H   H   L
181/61                                          211/71
ACC CGC CAC TCA CTC ACT CAT ACT GGC GAG AAA AAC TTC ACA TGT GAC TCG GAT GGA TGT
 T   R   H   S   L   T   H   T   G   E   K   N   F   T   C   D   S   D   G   C
241/81                                          271/91
GAC TTG AGA TTT ACT ACA AAG GCA AAC ATG AAG AAG CAC TTT AAC AGA TTC CAT AAC ATC
 D   L   R   F   T   T   K   A   N   M   K   K   H   F   N   R   F   H   N   I
301/101                                         331/111
AAG ATC TGC GTC TAT GTG TGC CAT TTT GAG AAC TGT GGC AAA GCA TTC AAG AAA CAC AAT
 K   I   C   V   Y   V   C   H   F   E   N   C   G   K   A   F   K   K   H   N
361/121                                         391/131
CAA TTA AAG GTT CAT CAG TTC AGT CAC ACA CAG CAG CTG CCG TAT GCT TGC CCT GTC GAG
 Q   L   K   V   H   Q   F   S   H   T   Q   Q   L   P   Y   A   C   P   V   E
421/141                                         451/151
TCC TGC GAT CGC CGC TTT TCT CGC TCG GAT GAG CTT ACC CGC CAT ATC CGC ATC CAC ACA
 S   C   D   R   R   F   S   R   S   D   E   L   T   R   H   I   R   I   H   T
481/161                                         511/171
GGC CAG AAG CCC TTC CAG TGT CGA ATC TGC ATG CGT AAC TTC AGT CGT AGT GAC CAC CTT
 G   Q   K   P   F   Q   C   R   I   C   M   R   N   F   S   R   S   D   H   L
541/181                                         571/191
ACC ACC CAC ATC CGC ACC CAC ACA GGC GAG AAG CCT TTT GCC TGT GAC ATT TGT GGG AGG
 T   T   H   I   R   T   H   T   G   E   K   P   F   A   C   D   I   C   G   R
601/201                                         631/211
AAG TTT GCC AGG AGT GAT GAA CGC AAG AGG CAT ACC AAA ATC CAT TTA AGA CAG AAG GAC
 K   F   A   R   S   D   E   R   K   R   H   T   K   I   H   L   R   Q   K   D
```

FIG. 15

GAC-F4-ZIF
SEQ ID NO: 54

```
1/1                                          31/11
ATG GCA GAA CGC CCG TAT GCT TGC CCT GTC GAG TCC TGC GAT CGC CGC TTT TCT CGC TCG
 M   A   E   R   P   Y   A   C   P   V   E   S   C   D   R   R   F   S   R   S
61/21                                        91/31
GAT GAG CTT ACC CGC CAT ATC CGC ATC CAC ACA GGC CAG AAG CCC TTC CAG TGT CGA ATC
 D   E   L   T   R   H   I   R   I   H   T   G   Q   K   P   F   Q   C   R   I
121/41                                       151/51
TGC ATG CGT AAC TTC AGT GAT AGA AGC AAT CTT GAA CGT CAC ACG AGG ACC CAC ACA GGC
 C   M   R   N   F   S   D   R   S   N   L   E   R   H   T   R   T   H   T   G
181/61                                       211/71
GAG AAG CCT TTT GCC TGT GAC ATT TGT GGG AGG AAG TTT GCC AGG AGT GAT GAA CGC AAG
 E   K   P   F   A   C   D   I   C   G   R   K   F   A   R   S   D   E   R   K
241/81                                       271/91
AGG CAT ACC AAA ATC CAT TTA AGA CAG AAG GAC AAC ATC AAG ATC TGC GTC TAT GTG TGC
 R   H   T   K   I   H   L   R   Q   K   D   N   I   K   I   C   V   Y   V   C
301/101                                      331/111
CAT TTT GAG AAC TGT GGC AAA GCA TTC AAG AAA CAC AAT CAA TTA AAG GTT CAT CAG TTC
 H   F   E   N   C   G   K   A   F   K   K   H   N   Q   L   K   V   H   Q   F
361/121                                      391/131
AGT CAC ACA CAG CAG CTG CCG TAT GCT TGC CCT GTC GAG TCC TGC GAT CGC CGC TTT TCT
 S   H   T   Q   Q   L   P   Y   A   C   P   V   E   S   C   D   R   R   F   S
421/141                                      451/151
CGC TCG GAT GAG CTT ACC CGC CAT ATC CGC ATC CAC ACA GGC CAG AAG CCC TTC CAG TGT
 R   S   D   E   L   T   R   H   I   R   I   H   T   G   Q   K   P   F   Q   C
481/161                                      511/171
CGA ATC TGC ATG CGT AAC TTC AGT CGT AGT GAC CAC CTT ACC ACC CAC ATC CGC ACC CAC
 R   I   C   M   R   N   F   S   R   S   D   H   L   T   T   H   I   R   T   H
541/181                                      571/191
ACA GGC GAG AAG CCT TTT GCC TGT GAC ATT TGT GGG AGG AAG TTT GCC AGG AGT GAT GAA
 T   G   E   K   P   F   A   C   D   I   C   G   R   K   F   A   R   S   D   E
601/201                                      631/211
CGC AAG AGG CAT ACC AAA ATC CAT TTA AGA CAG AAG GAC
 R   K   R   H   T   K   I   H   L   R   Q   K   D
```

FIG. 16

ZIF-ZnF-GAC

SEQ ID NO: 55

```
1/1                                              31/11
ATG GCA GAA CGC CCG TAT GCT TGC CCT GTC GAG TCC TGC GAT CGC CGC TTT TCT CGC TCG
 M   A   E   R   P   Y   A   C   P   V   E   S   C   D   R   R   F   S   R   S
61/21                                            91/31
GAT GAG CTT ACC CGC CAT ATC CGC ATC CAC ACA GGC CAG AAG CCC TTC CAG TGT CGA ATC
 D   E   L   T   R   H   I   R   I   H   T   G   Q   K   P   F   Q   C   R   I
121/41                                           151/51
TGC ATG CGT AAC TTC AGT CGT AGT GAC CAC CTT ACC ACC CAC ATC CGC ACC CAC ACA GGC
 C   M   R   N   F   S   R   S   D   H   L   T   T   H   I   R   T   H   T   G
181/61                                           211/71
GAG AAG CCT TTT GCC TGT GAC ATT TGT GGG AGG AAG TTT GCC AGG AGT GAT GAA CGC AAG
 E   K   P   F   A   C   D   I   C   G   R   K   F   A   R   S   D   E   R   K
241/81                                           271/91
AGG CAT ACC AAA ATC CAT ACC GGT GAA CGG CCG TTC CAG TGT CGA ATC TGC ATG CGT AAC
 R   H   T   K   I   H   T   G   E   R   P   F   Q   C   R   I   C   M   R   N
301/101                                          331/111
TTC AGT TCT AGT AGC TCT CTT ACC AGC CAC ATC CGC ACC CAC ACA GGT GAG CGG CCG TAT
 F   S   S   S   S   L   T   S   H   I   R   T   H   T   G   E   R   P   Y
361/121                                          391/131
GCT TGC CCT GTC GAG TCC TGC GAT CGC CGC TTT TCT CGC TCG GAT GAG CTT ACC CGC CAT
 A   C   P   V   E   S   C   D   R   R   F   S   R   S   D   E   L   T   R   H
421/141                                          451/151
ATC CGC ATC CAC ACA GGC CAG AAG CCC TTC CAG TGT CGA ATC TGC ATG CGT AAC TTC AGT
 I   R   I   H   T   G   Q   K   P   F   Q   C   R   I   C   M   R   N   F   S
481/161                                          511/171
GAT AGA AGC AAT CTT GAA CGT CAC ACG AGG ACC CAC ACA GGC GAG AAG CCT TTT GCC TGT
 D   R   S   N   L   E   R   H   T   R   T   H   T   G   E   K   P   F   A   C
                   541/181                                571/191
GAC ATT TGT GGG AGG AAG TTT GCC AGG AGT GAT GAA CGC AAG AGG CAT ACC AAA ATC CAT
 D   I   C   G   R   K   F   A   R   S   D   E   R   K   R   H   T   K   I   H
601/201
TTA AGA CAG AAG GAC
 L   R   Q   K   D
```

FIG. 17

METHODS AND COMPOSITIONS FOR LINKING BINDING DOMAINS IN NUCLEIC ACID BINDING PROTEINS

CROSS REFERENCE TO RELATED APPLICATIONS

This applications claims priority under 35 U.S.C. §365(c) and 35 U.S.C. §120 to PCT/GB01/00202 and priority under 35 U.S.C. §119/363 to United Kingdom applications serial nos. 0001582.6, 0013102.9, 0013103.7 and 0013104.5.

FIELD OF THE INVENTION

This invention also relates to linkers for linking together nucleic acid binding polypeptide modules. This invention further relates to nucleic acid binding polypeptides, in particular nucleic acid binding polypeptides capable of binding sequences separated by one or more gaps of varying sizes, and methods for designing such polypeptides.

BACKGROUND OF THE INVENTION

Protein-nucleic acid recognition is a commonplace phenomenon which is central to a large number of biomolecular control mechanisms which regulate the functioning of eukaryotic and prokaryotic cells. For instance, protein-DNA interactions form the basis of the regulation of gene expression and are thus one of the subjects most widely studied by molecular biologists. Many DNA-binding proteins contain independently folded domains for the recognition of DNA, and these domains in turn belong to a large number of structural families, such as the leucine zipper, the "helix-turn-helix" and zinc finger families. Despite the great variety of structural domains, the specificity of the interactions observed to date between protein and DNA most often derives from the complementarity of the surfaces of a protein α-helix and the major groove of DNA (Klug, 1993, *Gene* 135:83-92).

Zinc finger proteins are ubiquitous eukaryotic DNA-binding modules first identified in *Xenopus* transcription factor IIIA (TFIIIA). Each zinc finger protein consists of a number of autonomous DNA binding units. For example, the mouse Zif268 zinc finger protein is a protein of 90 amino acid residues belonging to the $Cys_2$-$His_2$ zinc family. Zif268 contains three independent zinc finger domains of 24 residues each. Each zinc finger domain ("finger") consists of a single α helix joined to two strands of antiparallel β-sheets and held together via chelation of a zinc ion (Pavletich and Pabo, 1991, *Science* 252, 809-817). Sequence-specific DNA binding is mediated by residues located on the exposed face of the αhelix, which interacts with the major groove of DNA. One zinc finger domain interacts with about three base pairs, so that a number of fingers, which are linked together by linkers, are required to bind a longer DNA sequence. The linkers of various zinc finger proteins have been compared, and a consensus sequence (the "canonical sequence") determined, consisting of four amino acids Gly-Glu-Lys-Pro (SEQ ID NO:56). This canonical linker is termed the "GEKP linker". However, variants of this sequence are possible, for example, Gly-Gln-Lys-Pro (SEQ ID NO:58), Gly-Glu-Arg-Pro (SEQ ID NO:57) and Gly-Gln-Arg-Pro (SEQ ID NO:59).

It has been suggested that the contacts between particular amino acids and DNA base sequence may be described by a simple set of rules. However, current methods for the design and selection of zinc finger modules are not generally capable of producing zinc finger proteins that are capable of binding to any given DNA sequence. This is because certain nucleotide sequences will constitute favourable binding sites for zinc finger binding. It is known, for example, that DNA sequences which contain G-rich regions are highly specific binding sites for zinc finger proteins. In particular, zinc fingers tend to bind DNA sequences which contain G at every third position with high specificity. On the other hand, with regard to other sequences it will be difficult or impossible to design zinc fingers which bind specifically to that sequence. Thus, for example, pyrimidine-rich DNA sequences comprise less favourable binding sites for zinc fingers. In order to increase the affinity and specificity of binding, it is therefore desirable to construct zinc fingers which will tolerate gaps between the nucleotide sequences which are contacted by the fingers.

It is known in the prior art to attempt to increase affinity and specificity of zinc finger binding by linking together separate zinc finger domains with a canonical sequence. Thus, Rebar (1997, PhD Thesis, Massachusetts Institute of Technology, Massachusetts, USA) and Shi (1995, PhD Thesis, Johns Hopkins University, Maryland, USA) describe linking additional fingers to a three-finger protein using a GERP linker, and observe a relatively modest increase in affinity. Furthermore, tandem linkage of two three-finger proteins using a canonical linker has been described by Liu et al (1997), *Proc. Natl. Acad. Sci. USA* 94, 5525-5530. The affinity of binding of this six finger protein is found to be increased approximately 68-74 fold relative to each three-finger peptide, which is a poor result compared to that predicted by theory. A different approach is described by Kim and Pabo (1998, *Proc. Natl. Acad. Sci. USA* 95, 2812-2817), who use structure based design to generate a six-finger construct, using flexible linkers comprising 8 or 11 amino acids to link two three finger peptides (Zif268 and NRE). However, this construct is only capable of spanning a single gap (comprising 0-2 base pairs) in the composite DNA target site. Structure based design has also been used to construct a fusion protein consisting of zinc fingers from Zif268 and the homeodomain from Oct-1 (Pomerantz et al., 1995, Science 267, 93-6). Thus, in summary, to date, several groups have created six (or nine)-finger fusion peptides to bind long stretches of DNA with high affinity (Kim, J-S. & Pabo, C, O. (1998) *Proc. Natl. Acad. Sci. USA* 95, 2812-2817; Liu, Q., Segal, D. J., Ghiara, J. B. & Barbas, C. F. III (1997) *Proc. Natl. Acad. Sci. USA* 94, 5525-5530; Kamiuchi, T., Abe, E., Imanishi, M., Kaji, T., Nagaoka, M. & Sugiura, Y. (1998) *Biochemistry* 37, 13827-13834). However, the affinities of these constructs vary greatly and have generally been far weaker than expected. In addition, all of these peptides have targeted either contiguous DNA sequences, or those containing just one or two nucleotides of unbound DNA.

It is therefore an object of the present invention to provide nucleic acid binding polypeptides which are capable of spanning longer gaps between DNA binding subsites. It is a further object of the invention to provide nucleic acid binding polypeptides which are capable of spanning a greater number of gaps between the DNA binding subsites. It is a yet further object of the invention to provide nucleic acid binding polypeptides which are capable of spanning variable gaps between DNA binding subsites.

SUMMARY OF THE INVENTION

The invention in general provides for the use of linkers to link two or more nucleic acid domains. The linkers according to the invention are non-canonical linkers, which are flexible or structured. According to the invention in its various aspects, we provide methods of producing a modified nucleic acid binding polypeptide, nucleic acid binding polypeptides as made by such a method, nucleic acid binding polypeptides, nucleic acids encoding such nucleic acid binding polypeptides, host cells transformed with such nucleic acids, pharmaceutical compositions comprising such polypeptides or such nucleic acids, and uses of certain linkers.

According to a first aspect of the invention, we provide a nucleic acid binding proteins comprising nucleic acid binding domains linked by flexible linkers. This aspect of the invention is summarised by the following paragraphs:

We describe a method of producing a modified nucleic acid binding polypeptide, the method comprising the steps of: (a) providing a nucleic acid binding polypeptide comprising a plurality of nucleic acid binding modules; (b) selecting a first binding domain consisting of one or two contiguous nucleic acid binding modules; (c) selecting a second binding domain consisting of one or two contiguous nucleic acid binding modules; and (d) introducing a linker sequence to link the first and second binding domains, the linker sequence comprising five or more amino acid residues. Preferably, the linker sequence is a flexible linker sequence.

Preferably, steps (b) to (d) are repeated. More preferably, in which the binding affinity and/or specificity of the modified polypeptide to a nucleic acid sequence is increased compared to the binding affinity and/or specificity of an unmodified polypeptide.

Preferably, the nucleic acid sequence comprises a sequence which is bound by the unmodified polypeptide. More preferably, the nucleic acid sequence comprises a sequence bound by the unmodified nucleic acid binding polypeptide, into which one or more nucleic acid residues has been inserted. Most preferably, the nucleic acid residue(s) are inserted between target subsites bound by the first and second binding domains of the unmodified polypeptide.

We further describe a method of making a nucleic acid binding polypeptide, the method comprising the steps of: (a) providing a first binding domain and a second binding domain, at least one of the first and second binding domains consisting of one or two nucleic acid binding module(s); and (b) linking the first and second binding domains with a linker sequence comprising five or more amino acid residues.

We further describe a nucleic acid binding polypeptide comprising a first binding domain and a second binding domain linked by a linker sequence comprising five or more amino acid residues, in which at least one of the first and second binding domains consists of one or two nucleic acid binding module(s).

The method or polypeptide may be one in which the nucleic acid binding module is a zinc finger of the $Cys_2$-$His_2$ type. Preferably, the nucleic acid binding module is selected from the group consisting of naturally occurring zinc fingers and consensus zinc fingers. Most preferably, the nucleic acid binding polypeptide is Zif-GAC.

Preferably, the method or polypeptide is such that each of the first and the second binding domains consists of two binding modules. More preferably, the linker sequence comprises between 5 and 8 amino acid residues.

Preferably, the linker sequence is provided by insertion of one or more amino acid residues into a canonical linker sequence. The canonical linker sequence may be selected from GEKP (SEQ ID NO:56), GERP (SEQ ID NO:57), GQKP (SEQ ID NO:58) and GQRP (SEQ ID NO:59). Preferably, the linker sequence comprises a sequence selected from: GGEKP (SEQ ID NO:60), GGQKP (SEQ ID NO:61), GGSGEKP (SEQ ID NO:62), GGSGQKP (SEQ ID NO:63), GGSGGSGEKP (SEQ ID NO:64), and GGSGGSGQKP (SEQ ID NO:65).

Preferably, the nucleic acid binding polypeptide comprises a nucleic acid sequence selected from SEQ ID Nos: 22, 23, 24, 25, 26 and 27.

We further describe a nucleic acid binding polypeptide produced by a method as described above, a nucleic acid encoding a nucleic acid binding polypeptide as described above, and a host cell transformed with a nucleic acid as described above.

We further describe a pharmaceutical composition comprising a polypeptide as described above or a nucleic acid as described above, together with a pharmaceutically acceptable carrier.

We further describe a nucleic acid binding polypeptide comprising a repressor domain and a plurality of nucleic acid binding domains, the nucleic acid binding domains being linked by at least one non-canonical linker. The repressor domain may be a transcriptional repressor domain selected from the group consisting of: a KRAB-A domain, an engrailed domain and a snag domain. Preferably, the nucleic acid binding domains are linked by at least one flexible linker.

According to a second aspect of the invention, we provide nucleic acid binding proteins comprising nucleic acid binding domains linked by structured linkers. This aspect of the invention is summarised by the following paragraphs:

We describe a method of producing a modified nucleic acid binding polypeptide, the method comprising the steps of: (a) providing a nucleic acid binding polypeptide comprising a plurality of nucleic acid binding modules; (b) selecting a first binding domain comprising a nucleic acid binding module; (c) selecting a second binding domain comprising a nucleic acid binding module; and (d) introducing a linker sequence comprising a structured linker to link the first and second binding domains.

Preferably, steps (b) to (d) are repeated. More preferably, the binding affinity and/or specificity of the modified polypeptide to a nucleic acid sequence is increased compared to the binding affinity and/or specificity of an unmodified polypeptide.

Preferably, the nucleic acid sequence comprises a sequence which is bound by the unmodified polypeptide. More preferably, the nucleic acid sequence comprises a sequence bound by the unmodified nucleic acid binding polypeptide, into which one or more nucleic acid residues has been inserted. Most preferably, the nucleic acid residue(s) are inserted between target subsites bound by the first and second binding domains of the unmodified polypeptide. The number of inserted nucleic acid residues maybe 1, 2, 3, 4, 5, 6, 7, 8, 9, 10 or 11 or more.

We further describe a method of making a nucleic acid binding polypeptide, the method comprising the steps of: (a) providing a first binding domain comprising a nucleic acid binding module; (b) providing a second binding domain comprising a nucleic acid binding module; and (c) linking the first and second binding domains with a linker sequence comprising a structured linker.

We further describe provide a non-naturally occurring nucleic acid binding polypeptide comprising a first binding domain comprising a nucleic acid binding module and a second binding domain comprising a nucleic acid binding module, the first and second binding domains being linked by a linker sequence comprising a structured linker.

Preferably, the nucleic acid binding module is a zinc finger of the $Cys_2$-$His_2$ type. More preferably, the method or polypeptide is one in which the nucleic acid binding module is selected from the group consisting of naturally occurring zinc fingers and consensus zinc fingers.

Preferably, the structured linker comprises an amino acid sequence which is not capable of specifically binding nucleic acid. More preferably, the structured linker is derived from a zinc finger by mutation of one or more of its base contacting residues to reduce or abolish nucleic acid binding activity of the zinc finger. The structured linker may comprise the amino acid sequence of TFIIIA finger IV. Alternatively, the zinc finger is finger 2 of wild type Zif268 mutated at positions −1, 2, 3 and 6.

Preferably, the method or polypeptide is one in which the first or second nucleic acid binding domain is selected from the group consisting of: fingers 1 to 3 of TFIIIA, GAC and Zif. More preferably, the nucleic acid binding polypeptide comprises substantially the sequence of TF(1-4)-ZIF (SEQ ID NO: 53), GAC-F4-Zif (SEQ ID NO: 54) or Zif-ZnF-GAC (SEQ ID NO: 55). Most preferably, the or each linker sequence comprises one or more further sequence(s), each further sequence comprising a canonical linker sequence, preferably GEKP (SEQ ID NO:56), GERP (SEQ ID NO:57), GQKP (SEQ ID NO:58) or GQRP (SEQ ID NO:59), optionally comprising one or more amino acid sequences inserted into the canonical sequence. The further sequences may be selected from: GGEKP (SEQ ID NO:60), GGQKP (SEQ ID NO:61), GGSGEKP (SEQ ID NO:62), GGSGQKP (SEQ ID NO:63), GGSGGSGEKP (SEQ ID NO:64), and GGSGGSGQKP (SEQ ID NO:65).

We further describe a nucleic acid binding polypeptide produced by any of the methods described above, a nucleic acid encoding a nucleic acid binding polypeptide as described above, and a host cell transformed with a nucleic acid as described above. We further describe a pharmaceutical composition comprising a polypeptide as described above or a nucleic acid as described above together with a pharmaceutically acceptable carrier.

We further describe the use of a structured linker in a method of making a nucleic acid binding polypeptide. The structured linker may separate first and second nucleic acid binding domains of the nucleic acid binding polypeptide, to enable the polypeptide to bind a nucleic acid target in which subsites bound by respective domains of the polypeptide are separated by one or more nucleic acid residues.

We further describe a nucleic acid binding polypeptide comprising a repressor domain and a plurality of nucleic acid binding domains, the nucleic acid binding domains being linked by at least one non-canonical linker. The repressor domain may be a transcriptional repressor domain selected from the group consisting of: a KRAB-A domain, an engrailed domain and a snag domain. The nucleic acid binding domains may be linked by at least one structured linker.

According to a third aspect of the invention, we provide nucleic acid binding proteins comprising nucleic acid binding domains linked by structured and flexible linkers in any combination. This aspect of the invention is summarised by the following paragraphs:

We describe a method of producing a modified nucleic acid nucleic acid binding polypeptide, the method comprising the steps of: (a) providing a nucleic acid binding polypeptide comprising a plurality of nucleic acid binding modules; (b) selecting a first binding domain consisting of one or two contiguous nucleic acid binding modules; (c) selecting a second binding domain consisting of one or two contiguous nucleic acid binding modules; (d) introducing a first linker sequence to link the first and second binding domains, the linker sequence comprising five or more amino acid residues; (e) selecting a third binding domain comprising a nucleic acid binding module; (f) selecting a fourth binding domain comprising a nucleic acid binding module; and (g) introducing a second linker sequence comprising a structured linker to link the third and fourth binding domains.

Preferably, steps (b) to (d) are repeated. More preferably, steps (e) to (g) are repeated. Preferably, the binding affinity and/or specificity of the modified polypeptide to a nucleic acid sequence is increased compared to the binding affinity and/or specificity of an unmodified polypeptide.

Preferably, the nucleic acid sequence comprises a sequence which is bound by the unmodified polypeptide. More preferably, the nucleic acid sequence comprises a sequence bound by the unmodified nucleic acid binding polypeptide, into which one or more nucleic acid residues has been inserted. Most preferably, the nucleic acid residue(s) are inserted between target subsites bound by the first and second binding domains of the unmodified polypeptide. The number of inserted nucleic acid residues maybe 1, 2, 3, 4, 5, 6, 7, 8, 9, 10 or 11 or more.

We also describe a method of making a nucleic acid binding polypeptide, the method comprising the steps of: (a) providing a first binding domain and a second binding domain, at least one of the first and second binding domains consisting of one or two nucleic acid binding module(s); (b) liking the first and second binding domains with a first linker sequence comprising five or more amino acid residues; (c) providing a third binding domain comprising a nucleic acid binding module; (d) providing a fourth binding domain comprising a nucleic acid binding module; and (e) linking the third and fourth binding domains with a second linker sequence comprising a structured linker.

We further describe a nucleic acid binding polypeptide comprising a first binding domain consisting of one or two contiguous nucleic acid binding modules and a second binding domain consisting of one or two contiguous nucleic acid binding modules, the first and second binding domains being linked by a first linker sequence comprising five or more amino acid residues; a third binding domain comprising a nucleic acid binding module and a fourth binding domain comprising a nucleic acid binding module, the third and fourth binding domains being linked by a second linker sequence comprising a structured linker.

In the methods and polypeptides described above, the first linker sequence may comprise a flexible linker. Preferably, the nucleic acid binding module is a zinc finger of the $Cys_2$-$His_2$ type. More preferably, the nucleic acid binding module is selected from the group consisting of naturally occurring zinc fingers and consensus zinc fingers.

Preferably, each of the first and the second binding domains consists of two binding modules. More preferably, the first linker sequence comprises between 5 and 8 amino acid residues. The first linker sequence may be provided by insertion of one or more amino acid residues into a canonical linker sequence. Preferably, the canonical linker sequence is selected from GEKP (SEQ ID NO:56), GERP (SEQ ID NO:57), GQKP (SEQ ID NO:58) and GQRP (SEQ ID NO:59). More preferably, the first linker sequence comprises a sequence selected from: GGEKP (SEQ ID NO:60), GGQKP (SEQ ID NO:61), GGSGEKP (SEQ ID NO:62), GGSGQKP (SEQ ID NO:63), GGSGGSGEKP (SEQ ID NO:64), and GGSGGSGQKP (SEQ ID NO:65). Most preferably, the nucleic acid binding polypeptide comprises a nucleic acid sequence selected from SEQ ID Nos: 22, 23, 24, 25, 26 and 27.

Preferably, the structured linker comprises an amino acid sequence which is not capable of specifically binding nucleic acid. More preferably, the structured linker comprises the amino acid sequence of TFIIIA finger IV. Alternatively, or in addition, the structured linker is derived from a zinc finger by mutation of one or more of its base contacting residues to reduce or abolish nucleic acid binding activity of the zinc finger. The zinc finger may be finger 2 of wild type Zif268 mutated at positions −1, 2, 3 and 6. Preferably, the third or fourth nucleic acid binding domain is selected from the group consisting of: fingers 1 to 3 of TFIIIA, GAC and Zif.

Preferably, the method or polypeptide as described above is one in which the nucleic acid binding polypeptide comprises substantially the sequence of TF(1-4)-ZIF (SEQ ID NO: 53), GAC-F4 -Zif (SEQ ID NO: 54) or Zif-ZnF-GAC (SEQ ID NO: 55). The second linker sequence may comprise one or more further sequence(s), each further sequence comprising a canonical linker sequence, preferably GEKP (SEQ ID NO:56), GERP (SEQ ID NO:57), GQKP (SEQ ID NO:58) or GQRP (SEQ ID NO:59), optionally comprising one or more amino acid sequences inserted into the canonical sequence. The further sequences may be selected from: GGEKP (SEQ ID NO:60), GGQKP (SEQ ID NO:61), GGSGEKP (SEQ ID NO:62), GGSGQKP (SEQ ID NO:63), GGSGGSGEKP (SEQ ID NO:64), and GGSGGSGQKP (SEQ ID NO:65).

We further describe a nucleic acid binding polypeptide produced by a method as described above, a nucleic acid encoding a nucleic acid binding polypeptide as described above, and a host cell transformed with a nucleic acid as described above.

We further describe a pharmaceutical composition comprising a polypeptide as described above, or a nucleic acid as described above, together with a pharmaceutically acceptable carrier.

We further describe a nucleic acid binding polypeptide comprising a repressor domain and a plurality of nucleic acid binding domains, the nucleic acid binding domains being linked by at least one flexible linker and by at least one structured linker.

We further describe a nucleic acid binding polypeptide in which the repressor domain is a transcriptional repressor domain selected from the group consisting of: a KRAB-A domain, an engrailed domain and a snag domain. The nucleic acid binding domains may be linked by at least one flexible linker, or they may be linked by at least one structured linker.

According to a further aspect of the invention, we provide the use of a nucleic acid binding domain comprising two zinc finger modules as a basic unit in the construction of a nucleic acid binding polypeptide.

According to a yet further aspect of the invention, we provide a method of producing a nucleic acid binding polypeptide, the method comprising providing a first and a second nucleic acid binding domain each comprising two zinc finger modules, and linking the first and second nucleic acid binding domains with a structured linker sequence or a flexible linker sequence.

According to a yet further aspect of the invention, we provide the use of a amino acid sequence comprising five or more amino acid residues as a flexible linker to join two or more nucleic acid binding domains comprising two zinc finger modules. According to a yet further aspect of the invention, we provide the use of an amino acid sequence comprising a zinc finger which is not capable of specifically binding nucleic acid, as a structured linker to join two or more nucleic acid binding domains comprising two zinc finger modules. The nucleic acid binding domain is preferably selected from a zinc finger polypeptide library, in which each polypeptide in the library comprises more than one zinc finger and wherein each polypeptide has been at least partially randomised such that the randomisation extends to cover the overlap of a single pair of zinc fingers.

According to a yet further aspect of the invention, we provide a method for producing nucleic acid binding domains comprising two zinc finger modules for use in constructing a nucleic acid binding polypeptide, the method comprising the steps of: (a) providing a zinc finger polypeptide library, in which each polypeptide in the library comprises more than one zinc finger and wherein each polypeptide has been at least partially randomised such that the randomisation extends to cover the overlap of a single pair of zinc fingers; (b) providing a nucleic acid sequence comprising at least 6 nucleotides; and (c) selecting sequences in the zinc finger library which are capable of binding to the nucleic acid sequence. Preferably, substantially one and a half zinc fingers are randomised in each polypeptide.

According to a yet further aspect of the invention, we provide a nucleic acid binding polypeptide comprising units of zinc finger binding domains linked by flexible and/or structured linkers, each zinc finger binding domain comprising two zinc finger modules.

BRIEF DESCRIPTION OF THE DRAWINGS

FIG. 2 shows the nucleic acid (SEQ ID NO:21) and amino acid (SEQ ID NO:131) sequence of the ZIF-GAC fusion construct, which is made by joining the third finger of wild-type ZIF to the first finger of the GAC clone using the peptide LRQKDGERP (SEQ ID NO:66).

FIG. 3 shows the nucleic acid (SEQ ID NO:22) and amino acid (SEQ ID NO:132) sequence of the 3x2F ZGS construct.

FIG. 4 shows the nucleic acid (SEQ ID NO:23) and amino acid (SEQ ID NO:133) sequence of the 3x2F ZGL construct.

FIG. 5 shows the nucleic acid (SEQ ID NO:24) and amino acid (SEQ ID NO:134) sequence of the 3x2F ZGXL construct.

FIG. 6 shows the nucleic acid (SEQ ID NO:25) and amino acid (SEQ ID NO:135) sequence of the 3x2F ZGSL construct.

FIG. 7 shows the nucleic acid (SEQ ID NO:26) and amino acid (SEQ ID NO:136) sequence of the 3x2F ZGLS construct.

FIG. 8 shows the nucleic acid (SEQ ID NO:27) and amino acid (SEQ ID NO:137) sequence of the 3x1F ZIF construct.

FIG. 15 shows the nucleic acid (SEQ ID NO:53) and amino acid (SEQ ID NO:138) sequence of the TF(F1-4)-ZIF fusion construct.

FIG. 16 shows the nucleic acid (SEQ ID NO:54) and amino acid (SEQ ID NO:139) sequence of the GAC-F4-ZIF construct.

FIG. 17 shows the nucleic acid (SEQ ID NO:55) and amino acid (SEQ ID NO:140) sequence of the ZIF-ZnF-GAC construct.

DETAILED DESCRIPTION OF THE INVENTION

Figure 1:
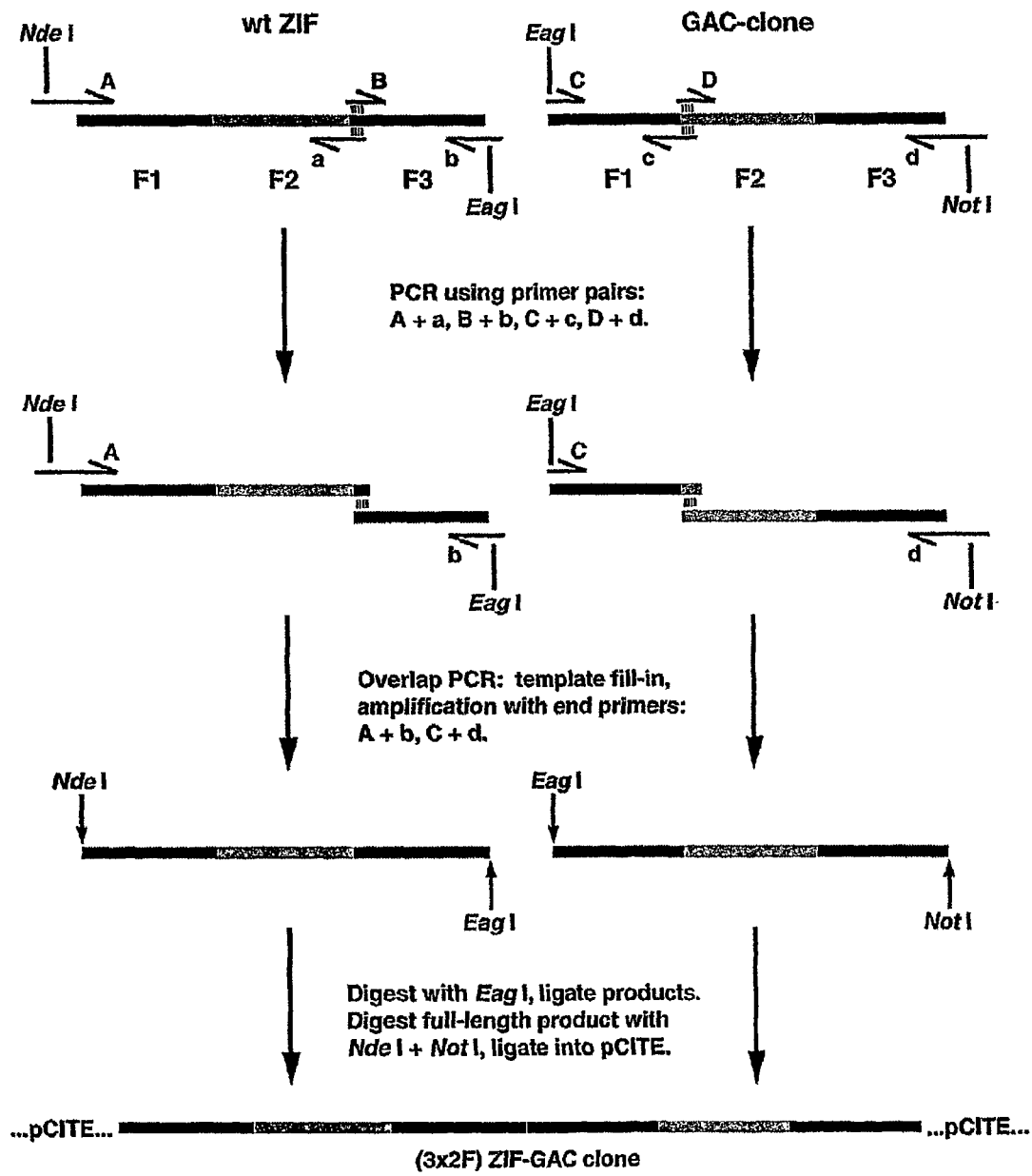
FIG. 1 is a schematic diagram showing the construction of the 3x2F and ZIF-GAC zinc finger constructs described here. Step 1: PCR using primer pairs A+a, B+b, C+c, D+d. Step 2: Overlap PCR; template fill-in and amplification with end primers A+b, C+d. Step 3: Digestion with EagI, ligation of resulting products; digestion of full-length product with NdeI+NotI, ligation into pCITE vector.

The invention relates to modified nucleic acid binding polypeptides and methods of producing these. A number of different novel nucleic acid binding polypeptides are disclosed. Methods are also disclosed for modifying an existing nucleic acid binding polypeptide comprising a plurality of nucleic acid binding modules. Where the nucleic acid binding polypeptide is provided by modification of an existing nucleic acid binding polypeptide, the binding affinity and/or specificity of the modified polypeptide to a substrate may be as good as, or better, than the corresponding binding affinity and/or specificity of the unmodified or starting nucleic acid to the same substrate.

Thus, the methods of our invention allow the production of nucleic acid binding polypeptides with higher binding affinity, or higher binding specificity, or both. As the term is used here, "specificity" means the ability of a nucleic acid binding polypeptide to discriminate between two or more putative nucleic acid targets. The higher its specificity, the less tolerant a nucleic acid binding polypeptide is to changes to the nature of the target, for example, nucleotide insertions, deletions, mutations, inversions, modifications (e.g., methylation, addition of a chemical moiety), etc. A nucleic acid binding polypeptide with high specificity for a target sequence is more discriminatory, and will likely bind to its target with a certain affinity (which may be a high affinity), and less likely to bind another target (which may comprise the target with changes as described above).

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons, J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

In a first aspect, we disclose the use of "flexible" linkers to link nucleic acid binding domains consisting of one or two nucleic acid binding modules. Thus, a method according to this aspect of our invention involves selecting binding domains within the nucleic acid binding polypeptide, each domain consisting of one or two nucleic acid binding modules, and linking these by means of a flexible linker sequence comprising five or more amino acid residues. Use of such flexible linkers allows the binding domains to bind to their cognate binding sites in the nucleic acid even when these are separated by one or more gaps, for example 2 gaps, of one, two, three or more nucleic acid residues. Thus, the peptides according to this aspect of the invention are capable of being able to span two short gaps of unbound DNA, while still binding with picomolar affinity to their target sites. In a highly preferred embodiment, the number of nucleic acid binding modules in each of the first and second binding domains is two.

Our invention is also based in part on the surprising discovery that use of linker sequences which adopt a specific conformational structure, rather than flexible linkers, to link two nucleic acid binding modules or domains results in modified nucleic acid binding polypeptides having improved binding characteristics. Such modified polypeptides are capable of binding nucleic acid targets comprising one or more relatively wide gaps of varying sizes inserted between target subsites.

In a second aspect, therefore, we disclose the use of "structured" linkers to link nucleic acid binding domains comprising at least one nucleic acid binding module. Thus, a method according to this aspect of our invention involves selecting binding domains within the nucleic acid binding polypeptide, each domain comprising one or more nucleic acid binding modules, and introducing a linker sequence comprising a structured linker to link the binding domains. By the use of such structured linkers, the binding domains in the modified nucleic acid binding polyptide are able to bind to their cognate binding sites in the nucleic acid even when these are separated by gaps of five or more nucleic acid residues.

The terms "flexible linker" and "structured linker" will be described and explained in further detail below.

A nucleic acid binding polypeptide may also be made which comprises a combination of flexible and structured linkers. Therefore, according to a third aspect, a method involves selecting first and second binding domains within the nucleic acid binding polypeptide, each domain consisting of one or two nucleic acid binding modules, and linking these by means of a flexible linker sequence comprising five or more amino acid residues. Further binding domains (third and fourth) within the nucleic acid binding polypeptide are then selected, each domain comprising one or more nucleic acid binding modules, and a linker sequence comprising a structured linker is introduced to link the third and fourth binding domains.

By "nucleic acid binding module" we mean a unit of peptide sequence which has nucleic acid binding activity. Examples of peptide sequences having nucleic acid binding activity include zinc fingers, leucine zippers, helix-turn-helix domains, and homeodomains. Preferably, the nucleic acid binding polypeptide comprises a zinc finger protein, and the nucleic acid binding modules comprise zinc fingers. A zinc finger binding motif is a structure well known to those in the art and defined in, for example, Miller et al., (1985) EMBO J. 4:1609-1614; Berg (1988) PNAS (USA) 85:99-102; Lee et al., (1989) Science 245:635-637; see International patent applications WO 96/06166 and WO 96/32475, corresponding to U.S. Ser. No. 08/422,107, now abandoned incorporated herein by reference. More preferably, the polypeptide is a zinc finger protein of the Cys2-His2 class. Accordingly, in preferred embodiments, the nucleic acid binding polypeptides of our invention are zinc finger proteins which comprise one or more structured linkers, or one or more flexible linkers, or a combination of flexible and structured linkers. Where the zinc finger comprises only flexible linkers, the number of zinc fingers in each binding domain linked by a flexible linker is preferably two. The zinc finger as a whole will preferably comprise 2 or more zinc fingers, for example 2, 3, 4, 5 or 6 zinc fingers. More preferably, the polypeptide comprises 6 zinc finger modules.

The nucleic acid binding polypeptides according to the invention need not consist of a uniform number of modules within each linked domain. Thus, polypeptides which comprise linked domains, in which the number of modules within each domain is different from domain to domain, are envisaged. Our invention therefore includes a zinc finger polypeptide comprising any combination of single finger domains and double finger domains, for example, the polypeptide comprising: finger pair-linker-single finger-single finger-finger pair, etc. The nucleic acid binding polypeptides according to this invention furthermore need not consist of only a single type of binding module. For example, hybrid polypeptides comprising more than one type of binding module are envisaged. Such hybrids include fusion proteins comprising: zinc finger and homeodomain, zinc finger and helix-loop-helix, helix-loop-helix and homeodomain, etc. These hybrid polypeptides may be made by modifications of the methods described in, for example, Pomerantz et al., 1995, Science 267, 93-6. Such modifications are regarded as within the skills of the reader. Furthermore, the linkages between the binding domains need not be uniform; they may comprise flexible linkers, structured linkers, or any combination of the two.

According to a further aspect of the invention, a zinc finger domain consisting of two zinc finger modules may be used as a basic unit or building block for the construction of multi-finger nucleic acid binding polypeptides. The two finger module units may be linked by one or more flexible linkers, one or more structured linkers, or a combination of the two. The two finger module units may be produced in a number of ways, by recombinant DNA techniques, or by selection from suitable libraries. We disclose the use of polypeptide and nucleic acid libraries, which comprise or encode zinc finger polypeptides comprising more than one finger, in which the relevant base contacting positions are fully or partially randomised. We show how such libraries, in particular, libraries encoding substantially one and a half fingers, may be used to select zinc finger pairs. We show that such multifinger polypeptides are effective in spanning one or more gaps in the target nucleic acid sequence.

Gap Spanning and Selective Binding

Nucleic acid binding polypeptides according to our invention are capable of binding to nucleic acids having a number of gaps between binding subsites, and are therefore capable of accommodating more stretches of unbound DNA within target sequences than those previously known. They therefore allow greater flexibility in the choice of potential binding sites. Furthermore, because the nucleic acid binding polypeptides of our invention are capable of spanning a number of gaps of varying stretches, they allow the targeting of the most favourable base contacts while avoiding less favourable nucleotide sequences. By extending the linker sequence between zinc finger pairs, we show that 3x2F peptides are able to accommodate two regions of unbound DNA within their recognition sequence, rather than one, as is the case for 2x3F peptides. Hence, these constructs also allow more flexibility in the selection of DNA target sequences for 'designer' transcription factors.

Furthermore, the nucleic acid binding polypeptides of our invention show a high degree of specificity for their cognate target sites, in that the polypeptides are not tolerant of deletions in the target sequence. We show that by changing the way in which zinc finger arrays are constructed—by linking three 2-finger domains rather than two 3-finger units—far greater selectivity can be achieved through increased sensitivity to mutated or closely related sequences.

Figure 21:
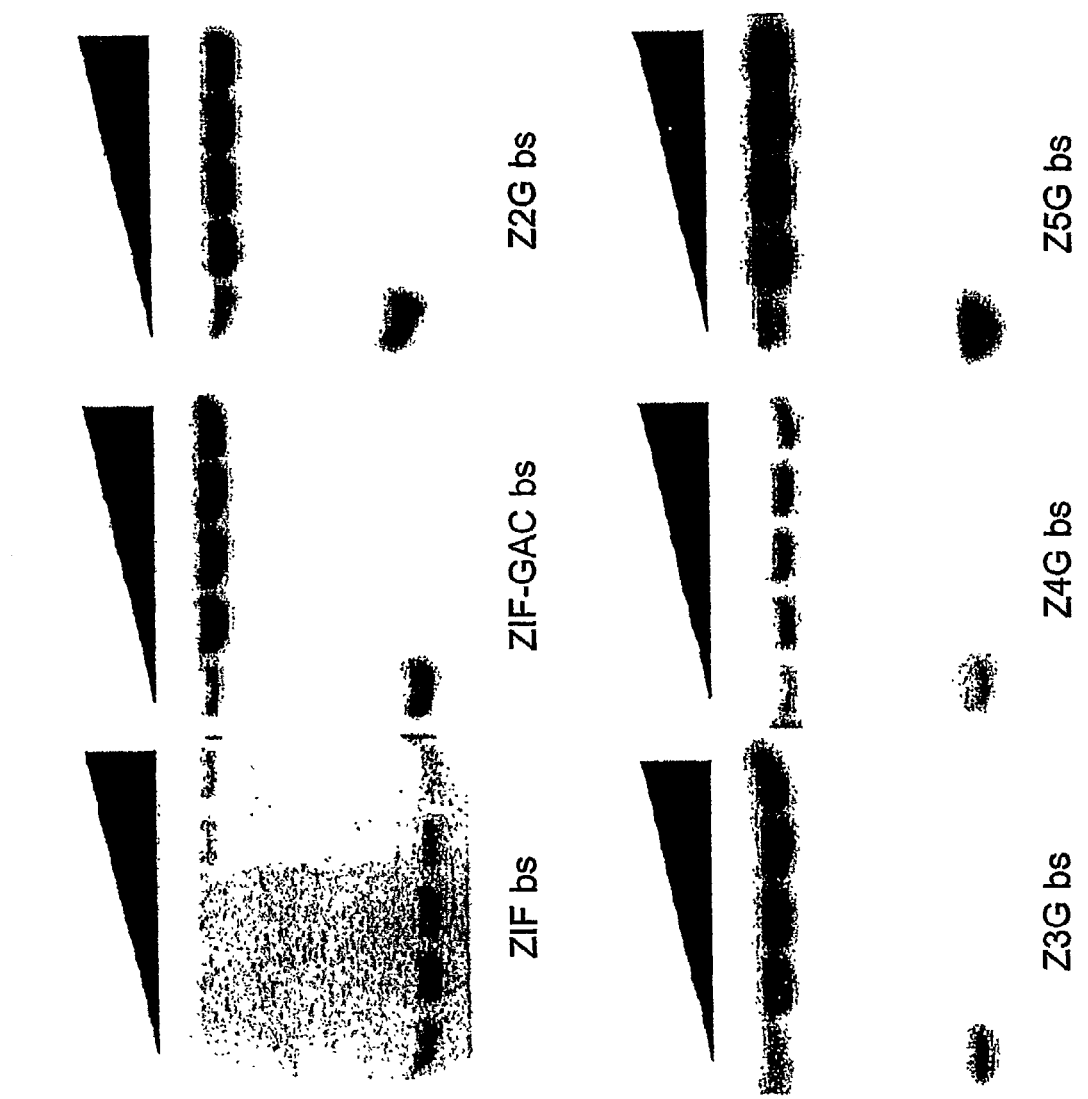
FIG. 21 shows results of gel-shift experiments in which the ZIF-ZnF-GAC peptide is tested for binding to the 9 base pair ZIF binding site (target bsA), the full length 18 base pair ZIF-GAC binding site (bsC), and sites with 2, 3, 4 and 5 base pairs between the ZIF and GAC-clone binding sites (labelled respectively Z2G, Z3G, Z4G and Z5G). The nucleotide sequences of Z2G, Z3G, Z4G and Z5G are as follow: Z2G: 5' GCG GAC GCG gtG CGT GGG CG 3' (SEQ ID NO:67), Z3G: 5' GCG GAC GCG agt GCG TGG GCG 3' (SEQ ID NO:68), Z4G: 5' GCG GAC GCG tag tGC GTG GGC G 3' (SEQ ID NO:69), Z5G: 5' GCG GAC GCG cta gtG CGT GGG CG 3' (SEQ ID NO:70). Serial 5-fold dilutions of peptide are indicated by the black triangle (reactions corresponding to left-hand lanes have less peptide than right-hand lanes), and binding site concentration is 0.10 nM.
Figure 22:
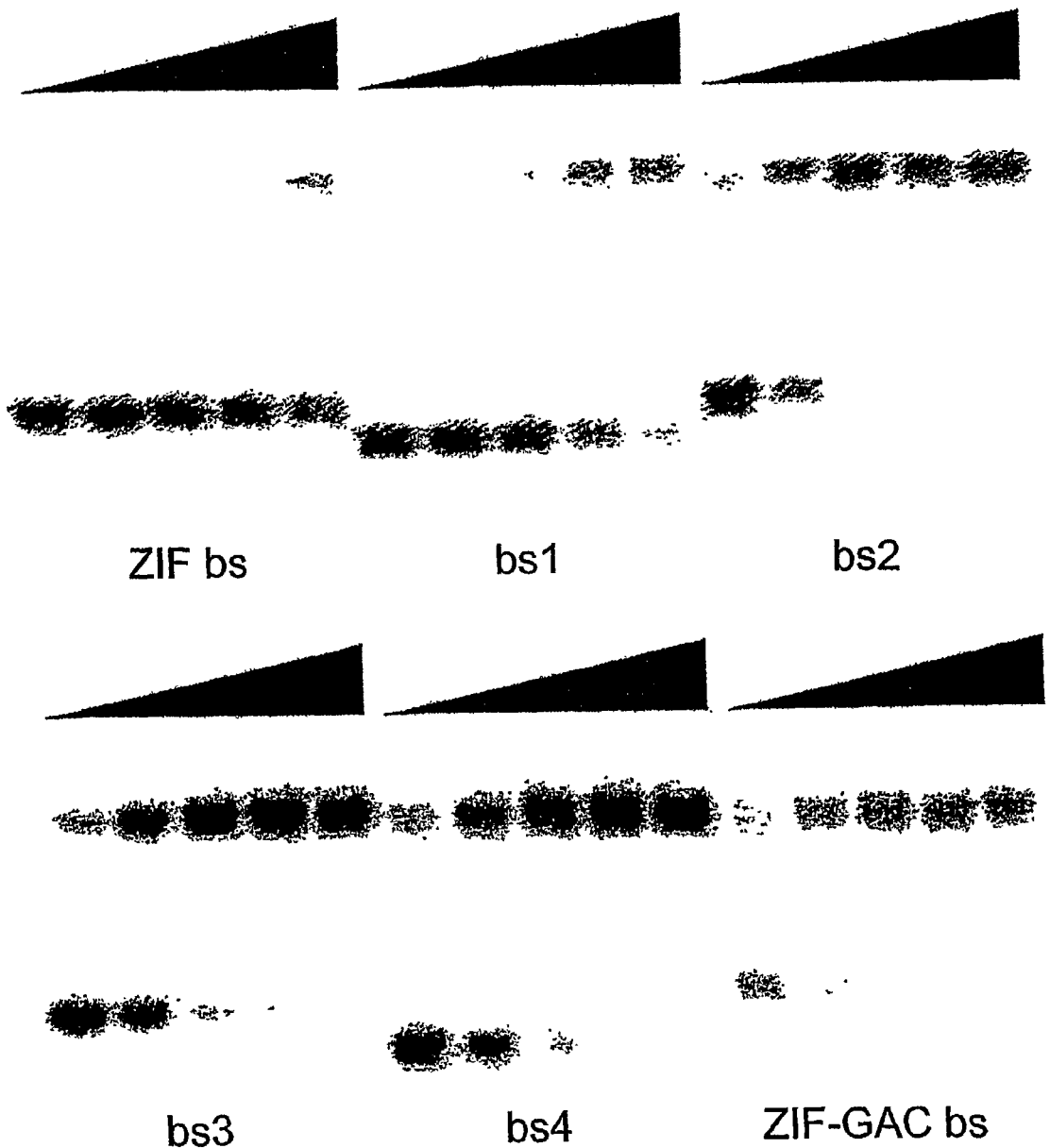
FIG. 22 shows results of gel-shift experiments in which the 2x3F ZIF-GAC peptide is tested for binding to the 9 base pair ZIF binding site (target bsA), the 18 base pair ZIF-GAC binding site (bsC) as well as bs1, bs2, bs3 and bs4, which comprise the ZIF-GAC bsC sequence, but with the three base subsequence recognised by finger 4 of 2x3F ZIF-GAC removed, and 0, 1, 2 or 3 base pairs respectively inserted in its place. The nucleotide sequences of bs1, bs2, bs3 and bs4 are as follow: bs1: GCG GAC GCG TGG GCG (SEQ ID NO:71), bs2: GCG GAC t GCG TGG GCG (SEQ ID NO:72), bs3: GCG GAC tc GCG TGG GCG (SEQ ID NO:73) and bs4: GCG GAC atc GCG TGG GCG (SEQ ID NO:74). Serial 5-fold dilutions of peptide are indicated by the black triangle (reactions corresponding to left-hand lanes have less peptide than right-hand lanes), and binding site concentration is 0.01 nM.

Thus, we have found that it is possible for known zinc finger proteins (for example, those comprising canonical linkers and Zif268/NRE as disclosed in WO99/45132) to bind to a subsequence consisting of a cognate target sequence with a target subsite deleted, by one or more of the fingers looping out of the protein-DNA complex. Thus, for example, we have found that a polypeptide consisting of 6 zinc fingers, besides being capable of binding to its cognate 18 base pair target site, is also capable of binding to a 15 base pair subsequence consisting of a 3 base pair deletion of the cognate 18 base pair target site. Thus, a ZIF-ZnF-GAC construct, having the sequences shown in FIG. 17, is able to bind to an 18 base pair nucleic acid sequences consisting of the 9 base pair ZIF recognition sequence linked to the 9 base pair GAC recognition sequence. In addition, this zinc finger construct is capable of binding with similar affinity to nucleic acid sequences consisting of 15, 16 or 17 base pairs (i.e., nucleic acid constructs consisting of ZIF and GAC recognition sites, but with 3, 2 or 1 residue removed). Furthermore, this zinc finger construct is also capable of binding with similar affinity to nucleic acid sequences consisting of 19, 20, 21, 22 and 23 base pair nucleic acid sequences comprising the ZIF and GAC recognition sites, separated by 1 to 5 nucleotide stretches. A selection of results from these experiments is shown in FIGS. 21 and 22 and explained in further detail below in Example 17. Without seeming to be bound by any particular theory, we believe that the versatility of binding of ZIF-ZnF-GAC to such a wide range of sequences is probably due to the middle ZnF finger (structured linker) being capable of looping out of the protein-DNA complex.

Looping out of such unbound fingers may be a general phenomenon. Thus, zinc finger constructs consisting of 2 three finger domains linked by a linker (for example, the 2x3F ZIF-GAC construct described below) are capable of binding nucleic acid sequences consisting of the cognate 18 base pair ZIF-GAC site (i.e., bsC) but with the corresponding target subsite for finger 4 deleted and replaced by 0, 1, 2, or 3 residues, with similar affinity to the full-length site. It would appear that the reason for this is that looping out of one of the fingers in this construct leaves behind two domains still capable of binding nucleic acid (namely a two finger domain and a three finger domain). The strength of binding of these remaining domains is sufficient to allow the entire construct to be bound to the sub-optimal target even with one finger looped out. Reference is made to FIG. 22 and Example 21 below. This phenomenon allows the polydactyl peptides (based on tandemly arrayed three-finger domains) reported in previous studies to bind with relatively high affinity to related DNA sites containing various mutations-and deletions. This would effectively mean that these peptides would not exclusively target the desired sequences within complex genomes.

Figure 23:
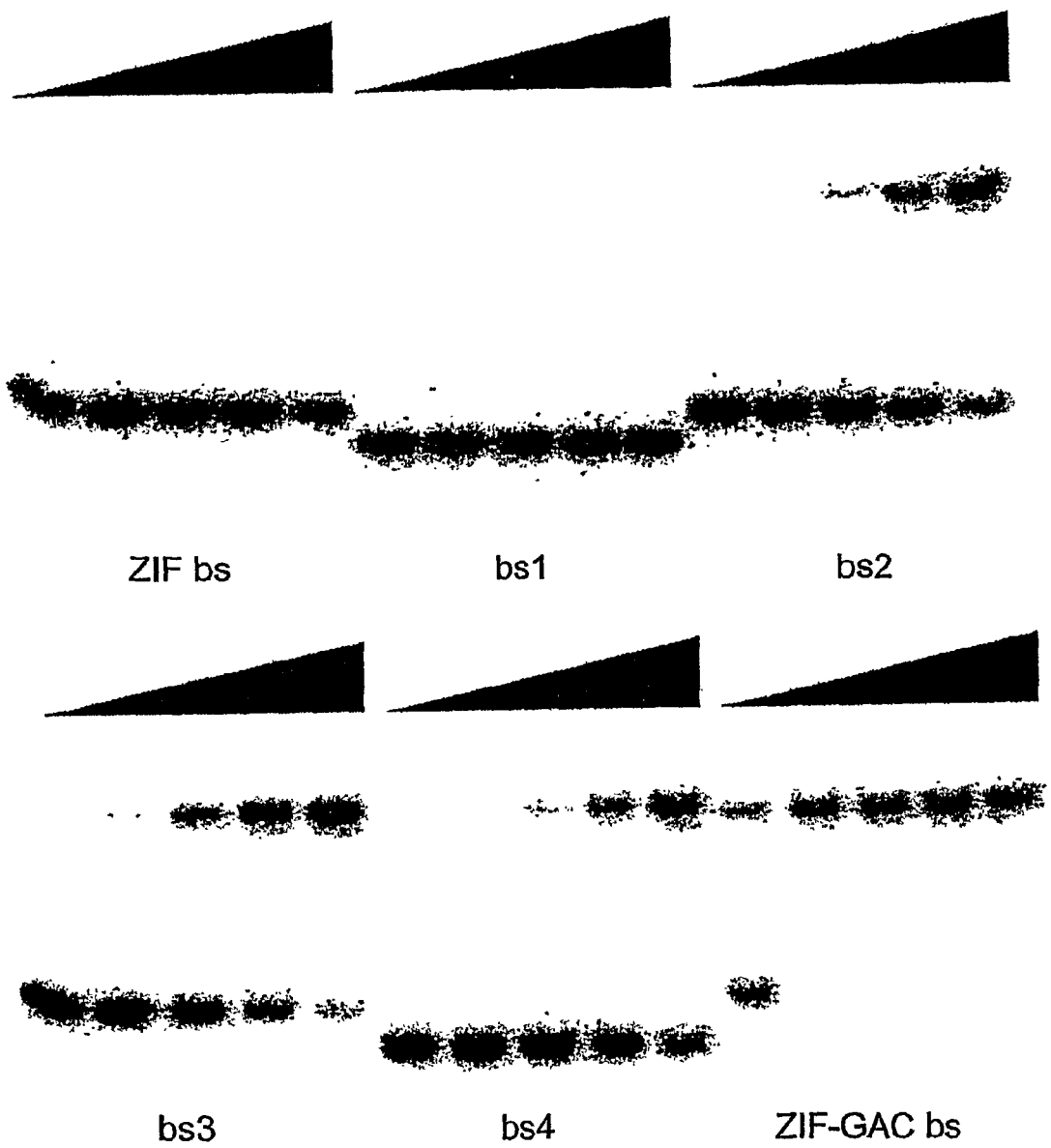
FIG. 23 shows results of gel-shift experiments in which the 3x2F ZGS peptide is tested for binding to the 9 base pair ZIF binding site (target bsA), the full length 18 base pair ZIF-GAC binding site, and sites bs1, bs2, bs3 and bs4 as indicated above for FIG. 22. Serial 5-fold dilutions of peptide are indicated by the black triangle (reactions corresponding to left-hand lanes have less peptide than right-hand lanes), and binding site concentration is 0.01 nM.
Figure 24:
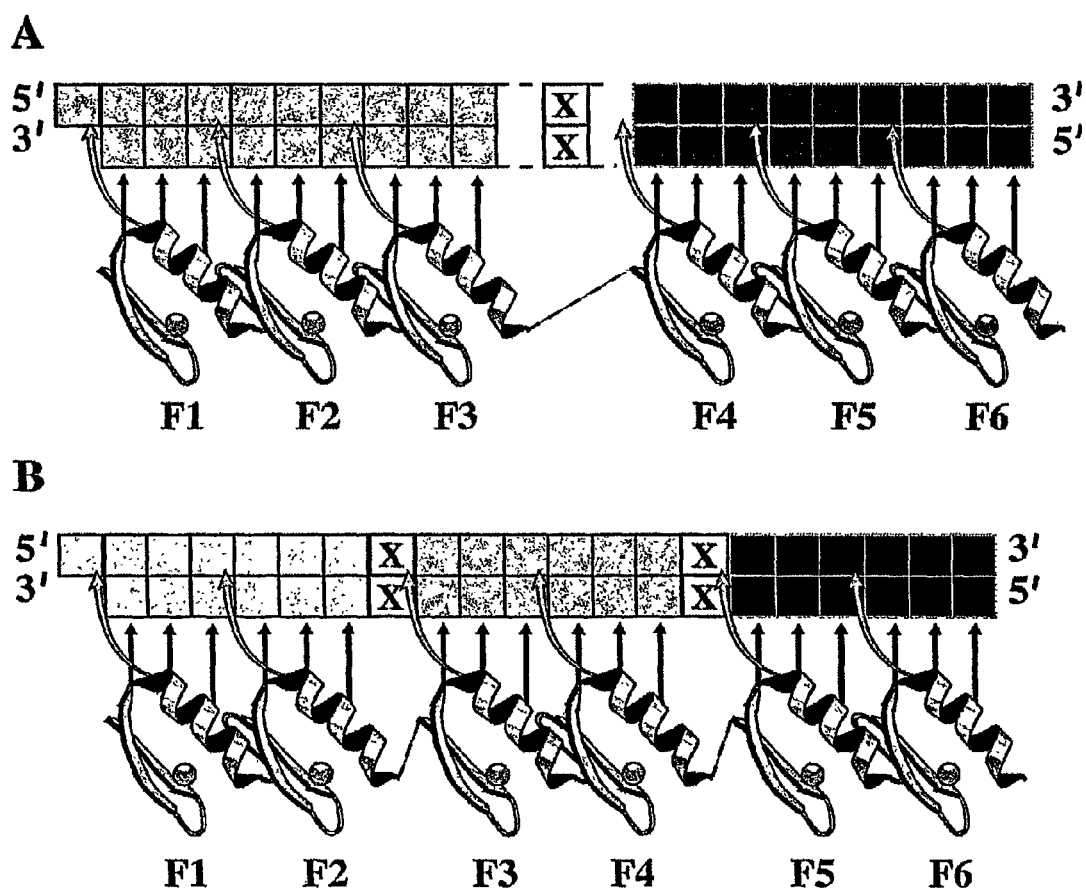
FIG. 24. The general structure of the six-finger arrays used in this study and potential regions of non-bound DNA marked with an 'X'. (A) 2x3F peptide with 9 bp subsites indicated, (B) 3x2F peptides with 6 bp subsites indicated.

On the other hand, the 3x2F nucleic acid binding polypeptides of our invention (in other words, three pairs of zinc fingers separated by flexible linkers) are only capable of binding these truncated binding sites with greatly reduced affinity, in comparison to their full-length targets. Thus, for example, a 3x2F ZGS construct binds extremely weakly to a nucleic acid sequence consisting of the cognate 18 base pair ZIF-GAC site (i.e., bsC) but with the corresponding target subsite for finger 4 deleted. The affinity of a 3x2F ZGS peptide for such a sequence is similar to the affinity to a 9 base pair ZIF site. Again without seeming to be bound by any particular theory, we believe that this is due to the fact that looping out of this finger leaves behind three separated domains for binding; the fact that these consist of two fingers, one finger and two fingers means that there is insufficient binding affinity for the entire construct to bind with high-affinity to the sub-optimal nucleic acid. The nucleic acid binding polypeptides of our invention therefore exhibit far greater selectivity through increased sensitivity to mutated or closely related sequences. Reference is made to FIG. 23 and Example 21 below.

The fact that the constructs according to this aspect of our invention, namely constructs in which pairs of zinc fingers are separated by flexible linkers, appear to be more particular in the targets they will detectably bind to is an additional factor contributing to their specificity.

In summary, within a three-finger unit the sub-optimal binding of an individual finger is better compensated for than within a two-finger unit. Therefore, by linking pairs of fingers together (with linkers slightly longer than canonical linkers), a more effective peptide for gene regulation is generated. In other words, the entire zinc finger pair would contribute minimal binding energy to the peptide-DNA complex if one of the fingers has a sub-optimal binding interaction. The design also improves six-finger peptide—DNA interactions by allowing the peptide to adjust more regularly to the register of the DNA double helix, reducing the strain within the complex, and enhancing the binding affinity. Creating six-finger constructs with two or more extended linker sequences also provides the opportunity to design extended zinc finger peptides that are capable of binding to composite targets with two regions of unbound DNA. The present invention therefore encompasses the use of two finger modules as a basic unit in the design of zinc finger polypeptides.

Target Site

A "target site" is the nucleic acid sequence recognised by a nucleic acid binding polypeptide such as a zinc finger protein. For a zinc finger protein, the length of a target site varies with the number of fingers present, and with the number of sequence specific bonds formed between the protein and the target site. Typically, a two-fingered zinc protein recognises a four to seven base pair target site, a three-fingered zinc finger protein recognises a six to ten base pair target site, and a six fingered zinc finger protein recognises two adjacent nine to ten base pair target sites. A "subsite" or a "target subsite" is a subsequence of the target site, and corresponds to a portion of the target site recognised by a subunit of the nucleic acid binding polypeptide, for example, a nucleic acid binding domain or module of the nucleic acid binding polypeptide.

Flexible and Structured Linkers

By "linker sequence" we mean an amino acid sequence that links together two nucleic acid binding modules. For example, in a "wild type" zinc finger protein, the linker sequence is the amino acid sequence lacking secondary structure which lies between the last residue of the α-helix in a zinc finger and the first residue of the β-sheet in the next zinc finger. The linker sequence therefore joins together two zinc fingers. Typically, the last amino acid in a zinc finger is a threonine residue, which caps the α-helix of the zinc finger, while a tyrosine/phenylalanine or another hydrophobic residue is the first amino acid of the following zinc finger. Accordingly, in a "wild type" zinc finger, glycine is the first residue in the linker, and proline is the last residue of the linker. Thus, for example, in the Zif268 construct, the linker sequence is G(E/Q)(K/R)P (SEQ ID NO:56, 57, 58 or 59).

A "flexible" linker is an amino acid sequence which does not have a fixed structure (secondary or tertiary structure) in solution. Such a flexible linker is therefore free to adopt a variety of conformations. An example of a flexible linker is the canonical linker sequence GERP/GEKP/GQRP/GQKP (SEQ ID NO:56, 57, 58 or 59). Flexible linkers are also disclosed in WO99/45132 (Kim and Pabo). By "structured linker" we mean an amino acid sequence which adopts a relatively well-defined conformation when in solution. Structured linkers are therefore those which have a particular secondary and/or tertiary structure in solution.

Determination of whether a particular sequence adopts a structure may be done in various ways, for example, by sequence analysis to identify residues likely to participate in protein folding, by comparison to amino acid sequences which are known to adopt certain conformations (e.g., known alpha-helix, beta-sheet or zinc finger sequences), by NMR spectroscopy, by X-ray diffraction of crystallised peptide containing the sequence, etc as known in the art.

The structured linkers of our invention preferably do not bind nucleic acid, but where they do, then such binding is not sequence specific. Binding specificity may be assayed for example by gel-shift as described below.

The linker may comprise any amino acid sequence that does not substantially hinder interaction of the nucleic acid binding modules with their respective target subsites. Preferred amino acid residues for flexible linker sequences include, but are not limited to, glycine, alanine, serine, threonine proline, lysine, arginine, glutamine and glutamic acid.

The linker sequences between the nucleic acid binding domains preferably comprise five or more amino acid residues. The flexible linker sequences according to our invention consist of 5 or more residues, preferably, 5, 6, 7, 8, 9, 10, 11, 12, 13, 14, 15, 16, 17, 18, 19 or 20 or more residues. In a highly preferred embodiment of the invention, the flexible linker sequences consist of 5, 7 or 10 residues.

Once the length of the amino acid sequence has been selected, the sequence of the linker may be selected, for example by phage display technology (see for example U.S. Pat. No. 5,260,203) or using naturally occurring or synthetic linker sequences as a scaffold (for example, GQKP (SEQ ID NO:58) and GEKP (SEQ ID NO:56), see Liu et al., 1997, *Proc. Nall. Acad. Sci. USA* 94, 5525-5530 and Whitlow et al., 1991, *Methods: A Companion to Methods in Enzymology* 2: 97-105). The linker sequence may be provided by insertion of one or more amino acid residues into an existing linker sequence of the nucleic acid binding polypeptide. The inserted residues may include glycine and/or serine residues. Preferably, the existing linker sequence is a canonical linker sequence selected from GEKP (SEQ ID NO:56), GERP (SEQ ID NO:57), GQKP (SEQ ID NO:58) and GQRP (SEQ ID NO:59). More preferably, each of the linker sequences comprises a sequence selected from GGEKP (SEQ ID NO:60), GGQKP (SEQ ID NO:61), GGSGEKP (SEQ ID NO:62), GGSGQKP (SEQ ID NO:63), GGSGGSGEKP (SEQ ID NO:64), and GGSGGSGQKP (SEQ ID NO:65).

Structured linker sequences are typically of a size sufficient to confer secondary or tertiary structure to the linker; such linkers may be up to 30, 40 or 50 amino acids long. In a preferred embodiment, the structured linkers are derived from known zinc fingers which do not bind nucleic acid, or are not capable of binding nucleic acid specifically. An example of a structured linker of the first type is TFIIIA finger IV; the crystal structure of TFIIIA has been solved, and this shows that finger IV does not contact the nucleic acid (Nolte et al., 1998, *Proc. Natl. Acad. Sci. USA* 95, 2938-2943.). An example of the latter type of structured linker is a zinc finger which has been mutagenised at one or more of its base contacting residues to abolish its specific nucleic acid binding capability. Thus, for example, a ZIF finger 2 which has residues −1, 2, 3 and 6 of the recognition helix mutated to serines so that it no longer specifically binds DNA may be used as a structured linker to link two nucleic acid binding domains.

The use of structured or rigid linkers to jump the minor groove of DNA is likely to be especially beneficial in (i) linking zinc fingers that bind to widely separated (>3 bp)

DNA sequences, and (ii) also in minimising the loss of binding energy due to entropic factors.

Typically, the linkers are made using recombinant nucleic acids encoding the linker and the nucleic acid binding modules, which are fused via the linker amino acid sequence. The linkers may also be made using peptide synthesis and then linked to the nucleic acid binding modules. Methods of manipulating nucleic acids and peptide synthesis methods are known in the art (see, for example, Maniatis, et al., 1991. *Molecular Cloning: A Laboratory Manual*. Cold Spring Harbor, N.Y., Cold Spring Harbor Laboratory Press).

Nucleic Acid Binding Polypeptides

This invention relates to nucleic acid binding polypeptides. The term 'polypeptide' (and the terms "peptide" and "protein") are used interchangeably to refer to a polymer of amino acid residues, preferably including naturally occurring amino acid residues. Artificial analogues of amino acids may also be used in the nucleic acid binding polypeptides, to impart the proteins with desired properties or for other reasons. The term "amino acid", particularly in the context where "any amino acid" is referred to, means any sort of natural or artificial amino acid or amino acid analogue that may be employed in protein construction according to methods known in the art. Moreover, any specific amino acid referred to herein may be replaced by a functional analogue thereof, particularly an artificial functional analogue. Polypeptides may be modified, for example by the addition of carbohydrate residues to form glycoproteins.

As used herein, "nucleic acid" includes both RNA and DNA, constructed from natural nucleic acid bases or synthetic bases, or mixtures thereof Preferably, however, the binding polypeptides of the invention are DNA binding polypeptides.

Particularly preferred examples of nucleic acid binding polypeptides are Cys2-His2 zinc finger binding proteins which, as is well known in the art, bind to target nucleic acid sequences via α-helical zinc metal atom coordinated binding motifs known as zinc fingers. Each zinc finger in a zinc finger nucleic acid binding protein is responsible for determining binding to a nucleic acid triplet, or an overlapping quadruplet, in a nucleic acid binding sequence. Preferably, there are 2 or more zinc fingers, for example 2, 3, 4, 5, 6, 7, 8, 9, 10, 11, 12, 13, 14, 15, 16, 17, 18 or more zinc fingers, in each binding protein. Advantageously, the number of zinc fingers in each zinc finger binding protein is a multiple of 2.

Thus, in one embodiment, the invention provides a method for preparing a nucleic acid binding polypeptide of the Cys2-His2 zinc finger class capable of binding to a target DNA sequence, in which zinc finger domains comprising one or two, preferably two, zinc finger modules are linked by flexible linkers or structured linkers.

All of the DNA binding residue positions of zinc fingers, as referred to herein, are numbered from the first residue in the α-helix of the finger, ranging from +1 to +9. "−1" refers to the residue in the framework structure immediately preceding the α-helix in a Cys2-His2 zinc finger polypeptide. Residues referred to as "++" are residues present in an adjacent (C-terminal) finger. Where there is no C-terminal adjacent finger, "++" interactions do not operate.

The present invention is in one aspect concerned with the production of what are essentially artificial DNA binding proteins. In these proteins, artificial analogues of amino acids may be used, to impart the proteins with desired properties or for other reasons. Thus, the term "amino acid", particularly in the context where "any amino acid" is referred to, means any sort of natural or artificial amino acid or amino acid analogue that may be employed in protein construction according to methods known in the art. Moreover, any specific amino acid referred to herein may be replaced by a functional analogue thereof, particularly an artificial functional analogue. The nomenclature used herein therefore specifically comprises within its scope functional analogues or mimetics of the defined amino acids.

The α-helix of a zinc finger binding protein aligns antiparallel to the nucleic acid strand, such that the primary nucleic acid sequence is arranged 3' to 5' in order to correspond with the N terminal to C-terminal sequence of the zinc finger. Since nucleic acid sequences are conventionally written 5' to 3', and amino acid sequences N-terminus to C-terminus, the result is that when a nucleic acid sequence and a zinc finger protein are aligned according to convention, the primary interaction of the zinc finger is with the—strand of the nucleic acid, since it is this strand which is aligned 3' to 5'. These conventions are followed in the nomenclature used herein. It should be noted, however, that in nature certain fingers, such as finger 4 of the protein GLI, bind to the +strand of nucleic acid: see Suzuki et al., (1994) NAR 22:3397-3405 and Pavietich and Pabo, (1993) Science 261:1701-1707. The incorporation of such fingers into DNA binding molecules according to the invention is envisaged.

The present invention may be integrated with the rules set forth for zinc finger polypeptide design in our copending European or PCT patent applications having publication numbers; WO 98/53057, WO 98/53060, WO 98/53058, WO 98/53059, describe improved techniques for designing zinc finger polypeptides capable of binding desired nucleic acid sequences. In combination with selection procedures, such as phage display, set forth for example in WO 96/06166, these techniques enable the production of zinc finger polypeptides capable of recognising practically any desired sequence.

Thus, in one embodiment, the invention provides a method for preparing a nucleic acid binding polypeptide of the Cys2-His2 zinc finger class capable of binding to a target DNA sequence, in which zinc finger domains comprising one or two, preferably two, zinc finger modules are linked by flexible linkers or structured linkers, and in which binding to each base of a DNA triplet by an α-helical zinc finger DNA binding module in the polypeptide is determined as follows: if the 5' base in the triplet is G, then position +6 in the α-helix is Arg and/or position ++2 is Asp; if the 5' base in the triplet is A, then position +6 in the α-helix is Gln or Glu and ++2 is not Asp; if the 5' base in the triplet is T, then position +6 in the α-helix is Ser or Thr and position ++2 is Asp; or position +6 is a hydrophobic amino acid other than Ala; if the 5' base in the triplet is C, then position +6 in the α-helix may be any amino acid, provided that position ++2 in the α-helix is not Asp; if the central base in the triplet is G, then position +3 in the α-helix is His; if the central base in the triplet is A, then position +3 in the α-helix is Asn; if the central base in the triplet is T, then position +3 in the α-helix is Ala, Ser, Ile, Leu, Thr or Val; provided that if it is Ala, then one of the residues at −1 or +6 is a small residue; if the central base in the triplet is 5-meC, then position +3 in the α-helix is Ala, Ser, Ile, Leu, Thr or Val; provided that if it is Ala, then one of the residues at −1 or +6 is a small residue; if the 3' base in the triplet is G, then position −1 in the α-helix is Arg; if the 3' base in the triplet is A, then position −1 in the α-helix is Gln and position +2 is Ala; if the 3' base in the triplet is T, then position −1 in the α-helix is Asn; or position −1 is Gln and position +2 is Ser; if the 3' base in the triplet is C, then position −1 in the α-helix is Asp and Position +1 is Arg; where the central residue of a target triplet is C, the use of Asp at position +3 of a zinc finger polypeptide allows preferential binding to C over 5-meC.

The foregoing represents a set of rules which permits the design of a zinc finger binding protein specific for any given target DNA sequence.

A zinc finger binding motif is a structure well known to those in the art and defined in, for example, Miller et al., (1985) EMBO J. 4:1609-1614; Berg (1988) PNAS (USA) 85:99-102; Lee et al., (1989) Science 245:635-637; see International patent applications WO 96/06166 and WO 96/32475, corresponding to U.S. Ser. No. 08/422,107, now abandoned incorporated herein by reference.

In general, a preferred zinc finger framework has the structure:

(A) $X_{0-2}$ C $X_{1-5}$ C $X_{9-14}$ H $X_{3-6}$ H/C (SEQ ID NO:75)

where X is any amino acid, and the numbers in subscript indicate the possible numbers of residues represented by X.

In a preferred aspect of the present invention, zinc finger nucleic acid binding motifs may be represented as motifs having the following primary structure (SEQ ID NO:76):

(B) $X^a$ C $X_{2-4}$ C $X_{2-3}$ F $X^c$ X X X X L X X H X X X$^b$ H-linker
      −1        1 2 3 4 5 6 7 8 9 wherein X (including $X^a$, $X^b$ and $X^c$) is any amino acid. $X_{2-4}$ and $X_{2-3}$ refer to the presence of 2 or 4, or 2 or 3, amino acids, respectively. The Cys and His residues, which together co-ordinate the zinc metal atom, are marked in bold text and are usually invariant, as is the Leu residue at position +4 in the α-helix. The linker, as noted elsewhere, may comprise a flexible or a structured linker.

Modifications to this representation may occur or be effected without necessarily abolishing zinc finger function, by insertion, mutation or deletion of amino acids. For example it is known that the second His residue may be replaced by Cys (Krizek et al., (1991) J. Am. Chem. Soc. 113:4518-4523) and that Leu at +4 can in some circumstances be replaced with Arg. The Phe residue before $X_c$ may be replaced by any aromatic other than Trp. Moreover, experiments have shown that departure from the preferred structure and residue assignments for the zinc finger are tolerated and may even prove beneficial in binding to certain nucleic acid sequences. Even taking this into account, however, the general structure involving an α-helix co-ordinated by a zinc atom which contacts four Cys or His residues, does not alter. As used herein, structures (A) and (B) above are taken as an exemplary structure representing all zinc finger structures of the Cys2-His2 type.

Preferably, $X^a$ is F/Y-X or P-F/Y-X. In this context, X is any amino acid. Preferably, in this context X is E, K, T or S. Less preferred but also envisaged are Q, V, A and P. The remaining amino acids remain possible.

Preferably, $X_{2-4}$ consists of two amino acids rather than four. The first of these amino acids may be any amino acid, but S, E, K, T, P and R are preferred. Advantageously, it is P or R. The second of these amino acids is preferably E, although any amino acid may be used.

Preferably, $X^b$ is T or I. Preferably, $X^c$ is S or T.

Preferably, $X_{2-3}$ is G-K-A, G-K-C, G-K-S or G-K-G. However, departures from the preferred residues are possible, for example in the form of M-R-N or M-R.

As set out above, the major binding interactions occur with amino acids −1, +3 and +6. Amino acids +4 and +7 are largely invariant. The remaining amino acids may be essentially any amino acids. Preferably, position +9 is occupied by Arg or Lys. Advantageously, positions +1, +5 and +8 are not hydrophobic amino acids, that is to say are not Phe, Trp or Tyr. Preferably, position ++2 is any amino acid, and preferably serine, save where its nature is dictated by its role as a ++2 amino acid for an N-terminal zinc finger in the same nucleic acid binding molecule.

In a most preferred aspect, therefore, bringing together the above, the invention allows the definition of every residue in a zinc finger DNA binding motif which will bind specifically to a given target DNA triplet.

The code provided by the present invention is not entirely rigid; certain choices are provided. For example, positions +1, +5 and +8 may have any amino acid allocation, whilst other positions may have certain options: for example, the present rules provide that, for binding to a central T residue, any one of Ala, Ser or Val may be used at +3. In its broadest sense, therefore, the present invention provides a very large number of proteins which are capable of binding to every defined target DNA triplet.

Preferably, however, the number of possibilities may be significantly reduced. For example, the non-critical residues +1, +5 and +8 may be occupied by the residues Lys, Thr and Gln respectively as a default option. In the case of the other choices, for example, the first-given option may be employed as a default. Thus, the code according to the present invention allows the design of a single, defined polypeptide (a "default" polypeptide) which will bind to its target triplet.

In a further aspect of the present invention, there is provided a method for preparing a DNA binding protein of the Cys2-His2 zinc finger class capable of binding to a target DNA sequence, comprising the steps of: a) selecting a model zinc finger from the group consisting of naturally occurring zinc fingers and consensus zinc fingers; b) mutating at least one of positions −1, +3, +6 (and ++2) of the finger; and c) inserting one or more flexible or structured linkers between zinc finger domains comprising one or two zinc finger modules.

In general, naturally occurring zinc fingers may be selected from those fingers for which the DNA binding specificity is known. For example, these may be the fingers for which a crystal structure has been resolved: namely Zif268 (Elrod-Erickson et al., (1996) Structure 4:1171-1180), GLI (Pavletich and Pabo, (1993) Science 261:1701-1707), Tramtrack (Fairall et al., (1993) Nature 366:483-487) and YY1 (Houbaviy et al., (1996) PNAS (ISA) 93:13577-13582). Preferably, the modified nucleic acid binding polypeptide is derived from Zif268, GAC, or a Zif-GAC fusion comprising three fingers from Zif linked to three fingers from GAC. By "GAC-clone", we mean a three-finger variant of ZIF268 which is capable of binding the sequence GCGGACGCG, as described in Choo & Klug (1994), Proc. Natl. Acad. Sci. USA, 91, 11163-11167.

The naturally occurring zinc finger 2 in Zif268 makes an excellent starting point from which to engineer a zinc finger and is preferred.

Consensus zinc finger structures may be prepared by comparing the sequences of known zinc fingers, irrespective of whether their binding domain is known. Preferably, the consensus structure is selected from the group consisting of the consensus structure P Y K C P E C G K S F S Q K S D L V K H Q R T H T (SEQ ID NO:77), and the consensus structure P Y K C S E C G K A F S Q K S N L T R H Q R I H T (SEQ ID NO:78).

The consensuses are derived from the consensus provided by Krizek et al., (1991) J. Am. Chem. Soc. 113: 4518-4523 and from Jacobs, (1993) PhD thesis, University of Cambridge, UK. In both cases, the linker sequences described above for joining two zinc finger domains together, namely structured or flexible linkers, can be formed on the ends of the consensus.

When the nucleic acid specificity of the model finger selected is known, the mutation of the finger in order to modify its specificity to bind to the target DNA may be directed to residues known to affect binding to bases at which the natural and desired targets differ. Otherwise, mutation of the model fingers should be concentrated upon residues −1, +3, +6 and ++2 as provided for in the foregoing rules.

In order to produce a binding protein having improved binding, moreover, the rules provided by the present invention may be supplemented by physical or virtual modelling of the protein/DNA interface in order to assist in residue selection.

In a further embodiment the invention provides a method for producing a zinc finger polypeptide capable of binding to a target DNA sequence, the method comprising: a) providing a nucleic acid library encoding a repertoire of zinc finger domains or modules, the nucleic acid members of the library being at least partially randomised at one or more of the positions encoding residues −1, 2, 3 and 6 of the α-helix of the zinc finger modules; b) displaying the library in a selection system and screening it against a target DNA sequence; c) isolating the nucleic acid members of the library encoding zinc finger modules or domains capable of binding to the target sequence; and d) linking zinc finger domains comprising one or two zinc finger modules with flexible or structured linkers.

Methods for the production of libraries encoding randomised polypeptides are known in the art and may be applied in the present invention. Randomisation may be total, or partial; in the case of partial randomisation, the selected codons preferably encode options for amino acids as set forth in the rules above.

Zinc finger polypeptides may be designed which specifically bind to nucleic acids incorporating the base U, in preference to the equivalent base T.

In a further preferred aspect, the invention comprises a method for producing a zinc finger polypeptide capable of binding to a target DNA sequence, the method comprising: a) providing a nucleic acid library encoding a repertoire of zinc finger polypeptides each possessing more than one zinc finger, the nucleic acid members of the library being at least partially randomised at one or more of the positions encoding residues −1, 2, 3 and 6 of the α-helix in a first zinc finger and at one or more of the positions encoding residues −1, 2, 3 and 6 of the α-helix in a further zinc finger of the zinc finger polypeptides; b) displaying the library in a selection system and screening it against a target DNA sequence; d) isolating the nucleic acid members of the library encoding zinc finger polypeptides capable of binding to the target sequence; and e) linking the isolated nucleic acid members with sequences encoding flexible or structured linkers.

In this aspect, the invention encompasses library technology described in our copending International patent application WO 98/53057, incorporated herein by reference in its entirety. WO 98/53057 describes the production of zinc finger polypeptide libraries in which each individual zinc finger polypeptide comprises more than one, for example two or three, zinc fingers; and wherein within each polypeptide partial randomisation occurs in at least two zinc fingers.

This allows for the selection of the "overlap" specificity, wherein, within each triplet, the choice of residue for binding to the third nucleotide (read 3' to 5' on the +strand) is influenced by the residue present at position +2 on the subsequent zinc finger, which displays cross-strand specificity in binding. The selection of zinc finger polypeptides incorporating cross-strand specificity of adjacent zinc fingers enables the selection of nucleic acid binding proteins more quickly, and/or with a higher degree of specificity than is otherwise possible.

Zinc finger binding motifs designed according to the invention may be combined into nucleic acid binding polypeptide molecules having a multiplicity of zinc fingers. Preferably, the proteins have at least two zinc fingers. The presence of at least three zinc fingers is preferred. Nucleic acid binding proteins may be constructed by joining the required fingers end to end, N-terminus to C-terminus, with flexible or structured linkers. Preferably, this is effected by joining together the relevant nucleic acid sequences which encode the zinc fingers to produce a composite nucleic acid coding sequence encoding the entire binding protein.

The invention therefore provides a method for producing a DNA binding protein as defined above, wherein the DNA binding protein is constructed by recombinant DNA technology, the method comprising the steps of: preparing a nucleic acid coding sequence encoding a plurality of zinc finger domains or modules defined above, inserting the nucleic acid sequence into a suitable expression vector; and expressing the nucleic acid sequence in a host organism in order to obtain the DNA binding protein. A "leader" peptide may be added to the N-terminal finger. Preferably, the leader peptide is MAEEKP (SEQ ID NO:79). This aspect of the invention is described in further detail below.

Transcriptional Regulation

According to a further aspect of our invention, we provide a nucleic acid binding polypeptide comprising a repressor domain and a plurality of nucleic acid binding domains, the nucleic acid binding domains being linked by at least one non-canonical linker. The repressor domain is preferably a transcriptional repressor domain selected from the group consisting of: a KRAB-A domain, an engrailed domain and a snag domain. Such a nucleic acid binding polypeptide may comprise nucleic acid binding domains linked by at least one flexible linker, one or more domains linked by at least one structured linker, or both.

The nucleic acid binding polypeptides according to our invention may be linked to one or more transcriptional effector domains, such as an activation domain or a repressor domain. Examples of transcriptional activation domains include the VP16 and VP64 transactivation domains of Herpes Simplex Virus. Alternative transactivation domains are various and include the maize C1 transactivation domain sequence (Sainz et al., 1997, Mol. Cell. Biol. 17: 115-22) and P1 (Goff et al., 1992, Genes Dev. 6: 864-75; Estruch et al., 1994, Nucleic Acids Res. 22: 3983-89) and a number of other domains that have been reported from plants (see Estruch et al., 1994, ibid).

Instead of incorporating a transactivator of gene expression, a repressor of gene expression can be fused to the nucleic acid binding polypeptide and used to down regulate the expression of a gene contiguous or incorporating the nucleic acid binding polypeptide target sequence. Such repressors are known in the art and include, for example, the KRAB-A domain Moosmann et al., Biol. Chem. 378: 669-677 (1997)) the engrailed domain (Han et al., Embo J. 12: 2723-2733 (1993)) and the snag domain (Grimes et al., Mol Cell. Biol. 16: 6263-6272 (1996)). These can be used alone or in combination to down-regulate gene expression.

It is known that zinc finger proteins may be fused to transcriptional repression domains such as the Kruppel-associated box (KRAB) domain to form powerful repressors. These fusions are known to repress expression of a reporter gene even when bound to sites a few kilobase pairs upstream from the promoter of the gene (Margolin et al., 1994, PNAS USA 91, 4509-4513). However, because of this, zinc finger-KRAB fusion proteins are likely to affect the expression of many genes other than the intended target gene. Thus, the feature of KRAB that it is capable of acting to repress transcription at a distance is likely to limit its usefulness in gene therapy. However, as zinc fingers of our invention are capable of spanning gaps and may therefore be engineered to bind specifically to promoter sequences, fusion proteins comprising KRAB together with zinc fingers of our invention are likely to be effective in repressing transcription in a specific manner. This could be achieved by designing zinc fingers to bind to specific promoter sequences, and making use of structured and/or flexible linkers to span non-optimal binding sequences where these are present. Fusion proteins comprising KRAB and these engineered finger proteins can then be made by methods known in the art and used to specifically repress transcription.

Nucleic Acids Encoding Nucleic Acid Binding Polypeptides

The nucleic acid binding polypeptides may be constructed using recombinant techniques as known in the art (Maniatis, et al., 1991. *Molecular Cloning: A Laboratory Manual*. Cold Spring Harbor, N.Y., Cold Spring Harbor Laboratory Press). Linker sequences may be introduced between the binding domains by restriction enzyme digestion and ligation. For example, zinc finger proteins may be constructed by joining together the relevant nucleic acid coding sequences encoding the zinc fingers to produce a composite coding sequence with the appropriate linkers. Alternatively and preferably, the nucleic acid binding polypeptides are modified by mutagenesis at the existing linker sequences, for example by PCR using mutagenic oligonucleotides. As described in further detail in the Examples, overlap PCR may be used to create chimeric zinc finger proteins having modified linker sequences.

The nucleic acid encoding the nucleic acid binding polypeptide according to the invention can be incorporated into vectors for further manipulation. As used herein, vector (or plasmid) refers to discrete elements that are used to introduce heterologous nucleic acid into cells for either expression or replication thereof. Selection and use of such vehicles are well within the skill of the person of ordinary skill in the art. Many vectors are available, and selection of appropriate vector will depend on the intended use of the vector, i.e. whether it is to be used for DNA amplification or for nucleic acid expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence. An example of an expression vector is pCITE-4b (Amersham International PLC).

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2μ plasmid origin is suitable for yeast, and various viral origins (e.g. SV40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in *E. coli* and then the same vector is transfected into yeast or mammalian cells even though it is not capable of replicating independently of the host cell chromosome. DNA may also be replicated by insertion into the host genome. However, the recovery of genomic DNA encoding the nucleic acid binding polypeptide is more complex than that of exogenously replicated vector because restriction enzyme digestion is required to excise nucleic acid binding polypeptide DNA. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media As to a selective gene marker appropriate for yeast any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript™ vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up nucleic acid binding polypeptide nucleic acid, such as dihydrofolate reductase DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes the nucleic acid binding polypeptide. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to nucleic acid binding polypeptide encoding nucleic acid. Such a promoter may be inducible or constitutive. The promoters are operably linked to DNA encoding the nucleic acid binding polypeptide by removing the promoter from the source DNA by restriction enzyme digestion and inserting the isolated promoter sequence into the vector. Both the native nucleic acid binding polypeptide promoter sequence and many heterologous promoters may be used to direct amplification and/or expression of nucleic acid binding polypeptide encoding DNA.

Promoters suitable for use with prokaryotic hosts include, for example, the β-lactamase and lactose promoter systems, alkaline phosphatase, the tryptophan (Trp) promoter system and hybrid promoters such as the tac promoter. Their nucleotide sequences have been published, thereby enabling the skilled worker operably to ligate them to DNA encoding nucleic acid binding polypeptide, using linkers or adapters to supply any required restriction sites. Promoters for use in bacterial systems will also generally contain a Shine-Delgarno sequence operably linked to the DNA encoding the nucleic acid binding polypeptide.

Preferred expression vectors are bacterial expression vectors which comprise a promoter of a bacteriophage such as phage λ or T7 which is capable of functioning in the bacteria In one of the most widely used expression systems, the nucleic acid encoding the fusion protein may be transcribed from the vector by T7 RNA polymerase (Studier et al, *Methods in Enzymol.* 185; 60-89, 1990). In the *E. coli* BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for over-production of many proteins. Alternatively the polymerase gene may be introduced on a lambda phage by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcH is XpressTm (Invitrogen) or pTrc99 (Pharmacia Biotech, SE) or vectors containing the tac promoter such as pKK223-3 (Pharmacia Biotech) or PMAL (New England Biolabs, MA, USA).

Moreover, the nucleic acid binding polypeptide gene according to the invention preferably includes a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, -phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (–173) promoter element starting at nucleotide –173 and ending at nucleotide –9 of the PH05 gene.

Nucleic acid binding polypeptide gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with nucleic acid binding polypeptide sequence, provided such promoters are compatible with the host cell systems.

Transcription of a DNA encoding nucleic acid binding polypeptide by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the vector at a position 5' or 3' to nucleic acid binding polypeptide DNA, but is preferably located at a site 5' from the promoter.

Advantageously, a eukaryotic expression vector encoding a nucleic acid binding polypeptide according to the invention may comprise a locus control region (LCR). LCRs are capable of directing high-level integration site independent expression of transgenes integrated into host cell chromatin, which is of importance especially where the nucleic acid binding polypeptide gene is to be expressed in the context of a permanently-transfected eukaryotic cell line in which chromosomal integration of the vector has occurred, or in transgenic animals.

Eukaryotic vectors may also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding nucleic acid binding polypeptide.

An expression vector includes any vector capable of expressing nucleic acid binding polypeptide nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding nucleic acid binding polypeptide may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding nucleic acid binding polypeptide in mammalian cells. Transient expression usually involves the use of an expression vector that is able to replicate efficiently in a host cell, such that the host cell accumulates many copies of the expression vector, and, in turn, synthesises high levels of nucleic acid binding polypeptide. For the purposes of the present invention, transient expression systems are useful e.g. for identifying nucleic acid binding polypeptide mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing nucleic acid binding polypeptide expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing the nucleic acid binding polypeptide. Suitable prokaryotes include eubacteria, such as Gram-negative or Gram-positive organisms, such as E. coli, e.g. E. coli K-12 strains, DH5a and HB101, or Bacilli. Further hosts suitable for the nucleic acid binding polypeptide encoding vectors include eukaryotic microbes such as filamentous fungi or yeast, e.g. Saccharomyces cerevisiae. Higher eukaryotic cells include insect and vertebrate cells, particularly mammalian cells including human cells or nucleated cells from other multicellular organisms. Propagation of vertebrate cells in culture (tissue culture) is a routine procedure and tissue culture techniques are known in the art. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency. To produce such stably or transiently transfected cells, the cells should be transfected with a sufficient amount of the nucleic acid binding polypeptide-encoding nucleic acid to form the nucleic acid binding polypeptide. The precise amounts of DNA encoding the nucleic acid binding polypeptide may be empirically determined and optimised for a particular cell and assay.

Host cells are transfected or, preferably, transformed with the expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al., 1989 Molecular Cloning: A Laboratory Manual, Second Edition, Cold Spring Harbor Laboratory Press).

Transfected or transformed cells are cultured using media and culturing methods known in the art, preferably under conditions, whereby the nucleic acid binding polypeptide encoded by the DNA is expressed The composition of suitable media is known to those in the art, so that they can be readily prepared. Suitable culturing media are also commercially available.

The binding affinity of the nucleic acid binding polypeptides according to our invention may be improved by randomising the polypeptides and selecting for improved binding. Methods for randomisation are disclosed in, for example, WO96/06166. Thus, zinc finger molecules designed according to the invention may be subjected to limited randomisation and subsequent selection, such as by phage display, in order to optimise the binding characteristics of the molecule.

The sequences of zinc finger binding motifs may be randomised at selected sites and the randomised molecules obtained may be screened and selected for molecules having the most advantageous properties. Generally, those molecules showing higher affinity and/or specificity of the target nucleic acid sequence are selected. Mutagenesis and screening of target nucleic acid molecules may be achieved by any suitable means. Preferably, the mutagenesis is performed at the nucleic acid level, for example by synthesising novel genes encoding mutant proteins and expressing these to obtain a variety of different proteins. Alternatively, existing genes can be themselves mutated, such by site-directed or random mutagenesis, in order to obtain the desired mutant genes.

Instead of, or in addition to, randomisation of the zinc finger sequence, a particular amino acid sequence may be chosen on the basis of rules which determine the optimal sequence for binding to any particular nucleic acid sequence. Such rules are disclosed, for example, in our International Application PCT/GB98/01516 (published as WO98/53060).

Mutations may be performed by any method known to those of skill in the art. Preferred, however, is site-directed mutagenesis of a nucleic acid sequence encoding the protein of interest. A number of methods for site-directed mutagenesis are known in the art, from methods employing single-stranded phage such as M13 to PCR-based techniques (see "PCR Protocols: A guide to methods and applications", M. A. Inis, D. H. Gelfand, J. J. Sninsky, T. J. White (eds.). Academic Press, New York, 1990). The commercially available Altered Site II Mutagenesis System (Promega) may be employed, according to the directions given by the manufacturer.

Screening of the proteins produced by mutant genes is preferably performed by expressing the genes and assaying the binding ability of the protein product A simple and advantageously rapid method by which this may be accomplished is by phage display, in which the mutant polypeptides are expressed as fusion proteins with the coat proteins of filamentous bacteriophage, such as the minor coat protein pII of bacteriophage M13 or gene III of bacteriophage Fd, and displayed on the capsid of bacteriophage transformed with the mutant genes. The target nucleic acid sequence is used as a probe to bind directly to the protein on the phage surface and select the phage possessing advantageous mutants, by affinity purification. The phage are then amplified by passage through a bacterial host, and subjected to further rounds of selection and amplification in order to enrich the mutant pool for the desired phage and eventually isolate the preferred clone(s). Detailed methodology for phage display is known in the art and set forth, for example, in U.S. Pat. No. 5,223,409; Choo and Klug, (1995) *Current Opinions in Biotechnology* 6:431-436; Smith, (1985) *Science* 228:1315-1317; and McCafferty et al., (1990) *Nature* 348:552-554; all incorporated herein by reference. Vector systems and kits for phage display are available commercially, for example from Pharmacia.

Binding affinity may also be assayed by means of a gel-shift assay, in which the mobility of a substrate in a gel is reduced in the presence of binding by a polypeptide. The nucleic acid substrate is labelled by, for example, $^{32}P$, for the band-shift to be easily visualised.

Uses

Nucleic acid binding polypeptides according to the invention may be employed in a wide variety of applications, including diagnostics and as research tools. Advantageously, they may be employed as diagnostic tools for identifying the presence of nucleic acid molecules in a complex mixture. Nucleic acid binding molecules according to the invention may be used to differentiate single base pair changes in target nucleic acid molecules. In a preferred embodiment, the nucleic acid binding molecules of the invention can be incorporated into an ELISA assay. For example, phage displaying the molecules of the invention can be used to detect the presence of the target nucleic acid, and visualised using enzyme-linked anti-phage antibodies.

Further improvements to the use of zinc finger phage for diagnosis can be made, for example, by co-expressing a marker protein fused to the minor coat protein (gVIII) of bacteriophage. Since detection with an anti-phage antibody would then be obsolete, the tine and cost of each diagnosis would be further reduced. Depending on the requirements, suitable markers for display might include the fluorescent proteins (A. B. Cubitt, et al., (1995) *Trends Biochem Sci.* 20, 448-455; T. T. Yang, et al., (1996) *Gene* 173, 19-23), or an enzyme such as alkaline phosphatase which has been previously displayed on gIII (J. McCafferty, R. H. Jackson, D. J. Chiswell, (1991) *Protein Engineering* 4, 955-961) Labelling different types of diagnostic phage with distinct markers would allow multiplex screening of a single nucleic acid sample. Nevertheless, even in the absence of such refinements, the basic ELISA technique is reliable, fast, simple and particularly inexpensive. Moreover it requires no specialised apparatus, nor does it employ hazardous reagents such as radioactive isotopes, making it amenable to routine use in the clinic. The major advantage of the protocol is that it obviates the requirement for gel electrophoresis, and so opens the way to automated nucleic acid diagnosis.

Polypeptides made according to the invention may be employed in the manufacture of chimeric restriction enzymes, in which a nucleic acid cleaving domain is fused to a nucleic acid binding polypeptide comprising for example a zinc finger as described herein. Moreover, the invention provides therapeutic agents and methods of therapy involving use of nucleic acid binding polypeptides as described herein.

In particular, the invention provides the use of polypeptide fusions comprising an integrase, such as a viral integrase, and a nucleic acid binding polypeptides according to the invention to target nucleic acid sequences in vivo (Bushman, 1994 *PNAS USA* 91:9233-9237). In gene therapy applications, the method may be applied to the delivery of functional genes into defective genes, or the delivery of nonsense nucleic acid in order to disrupt undesired nucleic acid. Alternatively, genes may be delivered to known, repetitive stretches of nucleic acid, such as centromeres, together with an activating sequence such as an LCR This represents a route to the safe and predictable incorporation of nucleic acid into the genome.

In conventional therapeutic applications, nucleic acid binding polypeptides according to the invention may be used to specifically knock out cell having mutant vital proteins. For example, if cells with mutant ras are targeted, they will be destroyed because ras is essential to cellular survival. Alternatively, the action of transcription factors may be modulated, preferably reduced, by administering to the cell agents which bind to the binding site specific for the transcription factor. For example, the activity of HIV tat may be reduced by binding proteins specific for HIV TAR. Moreover, binding proteins according to the invention may be coupled to toxic molecules, such as nucleases, which are capable of causing irreversible nucleic acid damage and cell death. Such agents are capable of selectively destroying cells which comprise a mutation in their endogenous nucleic acid. Nucleic acid binding polypeptides and derivatives thereof as set forth above may also be applied to the treatment of infections and the like in the form of organism-specific antibiotic or antiviral drugs. In such applications, the binding proteins may be coupled to a nuclease or other nuclear toxin and targeted specifically to the nucleic acids of microorganisms.

Poly-zinc finger peptides, with their ability to bind with high affinity to long ($\geq 18$ bp) DNA target sequences, are likely to be used more and more in the search for gene therapy treatments and applications such as transgenic plants/animals. However, for such applications to be effective and safe it is crucial that high affinity zinc finger peptides are also highly specific. This is of particular importance given the extremely slow off rates observed for extended zinc finger arrays (Kim, J-S. & Pabo, C. O. (1998) *Proc. Natl. Acad. Sci. USA* 95, 2812-2817). The zinc fingers disclosed in this document better satisfy both these requirements. We have achieved this by creating a design of six-finger peptides, which not only gives a slightly higher affinity than a comparable 2x3F peptide, but more importantly, with far greater specificity for its full-length target. The two-finger units employed also allow greater flexibility in the selection of target sites by allowing one or two gaps of non-bound DNA, and reduce the library size required to select specific binding domains by techniques such as phage display. 3x2F peptides will greatly enhance the application of zinc finger arrays for the in vivo control of gene expression.

Proteins and polypeptides suitable for treatment using the nucleic acid binding proteins of our invention include those involved in diseases such as cardiovascular, inflammatory, metabolic, infectious (viral, bacteria, fungul, etc), genetic, neurological, rheumatological, dermatological, and musculoskeletal diseases. In particular, the invention provides nucleic acid binding proteins suitable for the treatment of diseases, syndromes and conditions such as hypertrophic cardiomyopathy, bacterial endocarditis, agyria, amyotrophic lateral sclerosis, tetralogy of fallot, myocarditis, anemia, brachial plexus, neuropathies, hemorrhoids, congenital heart defects, alopecia areata, sickle cell anemia, mitral valve prolapse, autonomic nervous system diseases, alzheimer disease, angina pectoris, rectal diseases, arrhythmogenic right, ventricular dysplasia, acne rosacea, amblyopia, ankylosing spondylitis, atrial fibrillation, cardiac tamponade, acquired immunodeficiency syndrome, amyloidosis, autism, brain neoplasms, central nervous system diseases, color vision defects, arteriosclerosis, breast diseases, central nervous system infections, colorectal neoplasms, arthritis, behcet's syndrome, breast neoplasms, cerebral palsy, cornmon cold, asthma, bipolar disorder, burns, cervix neoplasms, communication disorders, atherosclerosis, candidiasis, charcot-marie disease, crohn disease, attention deficit disorder, brain injuries, cataract, ulcerative colitis, cumulative trauma disorders, cystic fibrosis, developmental disabilities, eating disorders, erysipelas, fibromyalgia, decubitus ulcer, diabetes, emphysema, *escherichia coli* infections, folliculitis, deglutition disorders, diabetic foot, encephalitis, esophageal diseases, food hypersensitivity, dementia, down syndrome, japanese encephalitis, eye neoplasms, dengue, dyslexia, endometriosis, fabry's disease, gastroenteritis, depression, dystonia, chronic fatigue syndrome, gastroesophageal reflux, gaucher's disease, hematologic diseases, hirschsprung disease, hydrocephalus, hyperthyroidism, gingivitis, hemophilia, histiocytosis, hyperhidrosis, hypoglycemia, glaucoma, hepatitis, hiv infections, hyperoxaluria, hypothyroidism, glycogen storage disease, hepatolenticular degeneration, hodgkin disease, hypersensitivity, immunologic deficiency syndromes, hernia, holt-oram syndrome, hypertension, impotence, congestive heart failure, herpes genitalis, huntington's disease, pulmonary hypertension, incontinence, infertility, leukemia, systemic lupus erythematosus, maduromycosis, mental retardation, inflammation, liver neoplasms, lyme disease, malaria, inborn errors of metabolism, inflammatory bowel diseases, long qt syndrome, lymphangiomyomatosis, measles, migraine, influenza, low back pain, lymphedema, melanoma, mouth abnormalities, obstructive lung diseases, lymphoma, meningitis, mucopolysaccharidoses, leprosy, lung neoplasms, macular degeneration, menopause, multiple sclerosis, muscular dystrophy, myofascial pain syndromes, osteoarthritis, pancreatic neoplasms, peptic ulcer, myasthenia gravis, nausea, osteoporosis, panic disorder, myeloma, acoustic neuroma, otitis media, paraplegia, phenylketonuria, myeloproliferative disorders, nystagmus, ovarian neoplasms, parkinson disease, pheochromocytoma, myocardial diseases, opportunistic infections, pain, pars planitis, phobic disorders, myocardial infarction, hereditary optic atrophy, pancreatic diseases, pediculosis, plague, poison ivy dermatitis, prion diseases, reflex sympathetic dystrophy, schizophrenia, shyness, poliomyelitis, prostatic diseases, respiratory tract diseases, scieroderma, sjogren's syndrome, polymyalgia rheumatica, prostatic neoplasms, restless legs, scoliosis, skin diseases, postpoliomyelitis syndrome, psoriasis, retinal diseases, scurvy, skin neoplasms, precancerous conditions, rabies, retinoblastoma, sex disorders, sleep disorders, pregnancy, sarcoidosis, sexually transmitted diseases, spasmodic torticollis, spinal cord injuries, testicular neoplasms, trichotillomania, urinary tract, infections, spinal dystaphism, substance-related disorders, thalassemia, trigeniinal neuralgia, urogenital diseases, spinocerebellar degeneration, sudden infant death, thrombosis, tuberculosis, vascular diseases, strabismus, tinnitus, tuberous sclerosis, post-traumatic stress disorders, syringomyelia, tourette syndrome, turner's syndrome, vision disorders, psychological stress, temporomandibular joint dysfunction syndrome, trachoma, urinary incontinence, von willebrand's disease, renal osteodystrophy, bacterial infections, digestive system neoplasms, bone neoplasms, vulvar diseases, ectopic pregnancy, tick-borne diseases, marfan syndrome, aging, williams syndrome, angiogenesis factor, urticaria, sepsis, malabsorption syndromes, wounds and injuries, cerebrovascular accident, multiple chemical sensitivity, dizziness, hydronephrosis, yellow fever, neurogenic arthropathy, hepatocellular carcinoma, pleomorphic adenoma, vater's ampulla, meckel's diverticulum, keratoconus skin, warts, sick building syndrome, urologic diseases, ischemic optic neuropathy, common bile duct calculi, otorhinolaryngologic diseases, superior vena cava syndrome, sinusitis, radius fractures, osteitis deformans, trophoblastic neoplasms, chondrosarcoma, carotid stenosis, varicose veins, creutzfeldt-jakob syndrome, gallbladder diseases, replacement of joint, vitiligo, nose diseases, environmental illness, megacolon, pneumonia, vestibular diseases, cryptococcosis, herpes zoster, fallopian tube neoplasms, infection, arrhythmia, glucose intolerance, neuroendocrine tumors, scabies, alcoholic hepatitis, parasitic diseases, salpingitis, cryptococcal meningitis, intracranial aneurysm, calculi, pigmented nevus, rectal neoplasms, mycoses, hemangioma, colonic neoplasms, hypervitaminosis a, nephrocalcinosis, kidney neoplasms, vitamins, carcinoid tumor, celiac disease, pituitary diseases, brain death, biliary tract diseases, prostatitis, iatrogenic disease, gastrointestinal hemorrhage, adenocarcinoma, toxic megacolon, amputees, seborrheic keratosis, osteomyelitis, barrett esophagus, hemorrhage, stomach neoplasms, chickenpox, cholecystitis, chondroma, bacterial infections and mycoses, parathyroid neoplasms, spermatic cord torsion, adenoma, lichen planus, anal gland neoplasms, lipoma, tinea pedis, alcoholic liver diseases, neurofibromatoses, lymphatic diseases, elder abuse, eczema, diverticulitis, carcinoma, pancreatitis, amebiasis, pyelonephritis, and infectious mononucleosis, etc.

Pharmaceutical Compositions

The invention likewise relates to pharmaceutical preparations which contain the compounds according to the invention or pharmaceutically acceptable salts thereof as active ingredients, and to processes for their preparation. The pharmaceutical preparations according to the invention which contain the compound according to the invention or pharmaceutically acceptable salts thereof are those for enteral, such as oral, furthermore rectal, and parenteral administration to for example warm-blooded animal(s), the pharmacological active ingredient being present on its own or together with a pharmaceutically acceptable carrier. The dose of the active ingredient depends on the species, age and the individual condition and also on the manner of administration. For example, in the normal case, an approximate daily dose of about 10 mg to about 250 mg is to be estimated in the case of oral administration for a human patient weighing approximately 75 kg.

The novel pharmaceutical preparations contain, for example, from about 10% to about 80%, preferably from about 20% to about 60%, of the active ingredient. Pharmaceutical preparations according to the invention for enteral or parenteral administration are, for example, those in unit dose forms, such as sugar-coated tablets, tablets, capsules or suppositories, and ampoules. These are prepared in a manner known in the art, for example by means of conventional mixing, granulating, sugar-coating, dissolving or lyophilising processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

Suitable carriers are, in particular, fillers, such as sugars, for example lactose, sucrose, mannitol or sorbitol, cellulose preparations and/or calcium phosphates, for example tricalcium phosphate or calcium hydrogen phosphate, furthermore binders, such as starch paste, using, for example, corn, wheat, rice or potato starch, gelatin, tragacanth, methylcellulose and/or polyvinylpyrrolidone, if desired disintegrants, such as the abovementioned starches, furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate, and/or polyethylene glycol. Sugar-coated tablet cores are provided with suitable coatings which, if desired, are resistant to gastric juice, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropyl-methylcellulose phthalate. Colorants or pigments, for example to identify or to indicate different doses of active ingredient, may be added to the tablets or sugar-coated tablet coatings.

Other orally utilisable pharmaceutical preparations are hard gelatin capsules, and also soft closed capsules made of gelatin and a plasticiser, such as glycerol or sorbitol. The hard gelatin capsules may contain the active ingredient in the form of granules, for example in a mixture with fillers, such as lactose, binders, such as starches, and/or lubricants, such as talc or magnesium stearate, and, if desired, stabilisers. In soft capsules, the active ingredient is preferably dissolved or suspended in suitable liquids, such as fatty oils, paraffin oil or liquid polyethylene glycols, it also being possible to add stabilisers.

Suitable rectally utilisable pharmaceutical preparations are, for example, suppositories, which consist of a combination of the active ingredient with a suppository base. Suitable suppository bases are, for example, natural or synthetic triglycerides, paraffin hydrocarbons, polyethylene glycols or higher alkanols. Furthermore, gelatin rectal capsules which contain a combination of the active ingredient with a base substance may also be used. Suitable base substances are, for example, liquid triglycerides, polyethylene glycols or paraffin hydrocarbons.

Suitable preparations for parenteral administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, if necessary, also stabilisers.

Two Finger Module Libraries

The present invention includes a method of constructing multi-finger zinc finger proteins which are based on a construction unit of two fingers. The use of combinatorial libraries for generating two-zinc finger DNA binding domains is disclosed. We further describe a number of linkers that are suitable in constructing multifinger proteins and that are especially suitable for use with construction units of two fingers.

According to this aspect of the invention, combinatorial library systems may be used to generate two-finger construction units. Such libraries take advantage on a number of features of the libraries described in published patent applications WO 98/53057, WO 98/53058, WO 98/53059, and WO 98/53060 which are hereby incorporated by reference. In particular, the libraries are constructed in such a way as to enable the synergistic interaction between the two fingers which comprise the selected two-finger construction unit to be utilised.

We have determined that DNA-binding subunits comprising two-zinc finger domains may be engineered through the variety of approaches described herein, each of which has distinct advantages for creating DNA-binding proteins. In each of the libraries detailed here, amino acid randomizations are made at various positions in the two zinc finger structures. Preferred randomizations are described here as well as in patent applications WO 96/06166, WO 98/53057, WO 98/53058, WO 98/53059, and WO 98/53060. However, a more restricted number of randomizations may be utilized in library construction to facilitate the process of construction. The library construction methods described herein can be used in conjunction with a variety of selection methods including phage display and ribosome display as detailed in patent applications WO 97/53057 and WO 00/27878, both of which are incorporated herein by reference.

In one approach, an isolated two finger library is constructed, which comprises amino acids known to contribute to DNA-binding affinity and specificity. Since the library does not contain a DNA-binding "anchor", the register of the interaction is not strictly fixed, so this library may suitably be used for applications where either (i) the precise register of interaction is not critical for subsequent applications, or (ii) very short DNA targets [6-7 bp] are used in the selection procedure, thereby fixing the interaction more precisely.

It is highly desirable to engineer 2-finger domains whose register of interaction is precisely fixed, and which can be targeted to any DNA sequence. We have shown that this can be achieved by employing "GCG" anchors (although any other anchor sequence can be employed) and two extensively-randomised zinc fingers. The libraries are designed to take into account synergistic effects between zinc fingers, by modifying cross-strand contacts from position 2. Consequently, position 2 of F2 in is modified to Ser or Ala so as to interact universally with either the $^7$C. in the "GCG" anchor, or any base ($^7$N) in the final target site sequence. Similarly, position 2 of F3 is modified to Ser or Ala so as not to interfere with the selection of bases $^4$X or $^4$X. As before, after selecting against particular DNA target sites, the genes for the appropriate 2-finger domains may be easily recovered by PCR.

In a further approach, two previously constructed libraries (Lib12 and Lib23, as described in WO 98/53057) are readily adapted to provide a resource of 2-finger subunits. These two libraries have been extensively characterised and used for the selection of zinc finger modules of 1.5 fingers, each of which is then recombined to generate a 3-finger module (see WO98/50357). We now show that these libraries can be used to select two finger units that bind DNA sites of the form 5'-GXX XXX-3' or 5'-XXX XXG-3' (where X is any base). After selecting against particular DNA target sites, the genes for the appropriate 2-finger domains may be easily recovered by PCR. Because of the design of the libraries, the "GCGG" or "GGCG" anchors serve to fix the register of DNA-protein interaction very precisely. Despite the fact that one base must be fixed as "G" in each target site, this still allows 2048 of all the 4096 ($=4^6$) possible 6-base 2-finger recognition sites to be targeted.

The general principle is demonstrated below.

|         | Binding Site (5'-3') |     |     |
| Library | F3  | F2  | F1  |
| ------- | --- | --- | --- |
| LIB12   | GCG | GXX | XXX |
| LIB23   | XXX | XXG | GCG |

Therefore, LIB12 may be used to select a novel 2-finger unit that binds a 6 bp site with a 5' guanine. Similarly, LIB23 can be used to select a novel 2-finger unit that binds a 6 bp site with a 3' guanine.

Accordingly, we have recognized that the concept of selection of two-finger construction units need not require full randomization of both zinc fingers as libraries can be generated which providing for the fixing of one (or more) of the base contacting positions and selection against a DNA sequence that incorporates the corresponding nucleotide at the pre-determined base contacting position. Libraries may, for example, be constructed from zinc finger proteins in which two of the nucleotides of either target triplet are fixed. Using Zif268 as the backbone this would, for example, allow selection of two finger modules which target the sequence 5'-GGNNNN-3' or 5'-NNNNGG-3'. Using other backbone zinc fingers, the fixed nucleotides may be other nucleotides.

In an extension of this concept, it will be appreciated that Lib12 and Lib23 can be used to select 2-finger domains which bind the sequences GCGGXX or XXGGCG respectively.

Further advantages offered by 2-finger domains include the following: (a) the 2-finger domains are independent so no problems are encountered when fusing separately selected units; (b) no further rounds of selection are required after selecting individual 2-finger domains; (c) 3x2F peptides are more specific Man 2x3F peptides; (d) 3x2F peptides allow two 1 bp gaps to be accommodated within the target sequence; (e) with minor modifications to the libraries any 6 bp sequence can be targeted in one go; (f) complete binding site signatures may be possible for entire 2-finger units by DNA micro-array ELISA. Thus, as indicated in (d) above, 3x2F peptides allow two 1 bp gaps to be accommodated within the target sequence, indeed 2-finger units bind with optimal efficiency when within 1 bp of each other.

The invention is further described, for the purposes of illustration only, in the following examples.

EXAMPLES

Example 1

Constructs, Targets and Nomenclature

In order to combine the benefits of tight binding to an extended DNA sequence, coupled with the flexibility to skip bases in the DNA target site, we designed a series of six fingered chimeric zinc finger proteins derived from wild type ZIF fused to a GAC-clone. Each construct comprises three pairs of zinc fingers separated by extended, flexible linker peptides. These are termed "3x2F peptides".

One such flexible linker construct comprises the fingers of the wt ZIF and GAC with zinc finger pairs separated by -GG$^E$/$_Q$KP- (SEQ ID NO:60 or 61) and is termed 3x2F ZGS (FIG. 3). This peptide targets the contiguous DNA binding sequence, bsC (Table 1), which comprises the wt ZIF and GAC-clone binding sites. To allow some variation in the binding sites targeted by the 3x2F protein, finger pairs are also separated by -GGSG$^E$/$_Q$KP- (SEQ ID NO:62 or 63), or -GGSGGSG$^E$/$_Q$KP- (SEQ ID NO:64 or 65) linker sequences to create the 3x2F ZGL and 3x2F ZGXL constructs respectively (FIGS. 4 and 5). These peptides are targeted against the contiguous ZIF-GAC binding site (bsC), and against the binding sites bsD and bsE (Table 1), which contain 1 or 2 bps, respectively, between the recognition sequences for the zinc finger pairs. Similar constructs are also synthesised in which two-finger units are separated by linkers containing either glycine or Gly-Gly-Ser insertions. These constructs are termed 3x2F ZGSL and 3x2F ZGLS (FIGS. 6 and 7) and are targeted against the appropriate binding sites, bsF and bsG (Table 1).

Constructs are also made comprising structured linkers. One such construct comprises the first four fingers of TFIIIA (including the F4-F5 linker peptide) joined to the N-terminus of the three-finger ZIF peptide. The resultant seven-finger peptide is denoted TF(F1-4)-ZIF (Example 15 and FIGS. 13 and 15), and is targeted to non-contiguous binding sites containing the TFIIIA F1-3 and wt ZIF sites separated by 5 to 10 bps of DNA (Table 2). The second construct is created by substituting the first three fingers of TFIIIA in the above fusion peptide with the three-finger GAC-clone, and is denoted GAC-F4-ZIF (Example 16 and FIGS. 14 and 16). This peptide is targeted against the non-contiguous binding sites (Table 3), which comprise the GAC-clone and wt ZIF recognition sites separated by 6 to 11 bps of DNA. A third structured linker construct is ZIF-ZnF-GAC which consists of the three finger peptide of ZIF linked to a three fingered GAC-clone using a "neutral" finger linker, i.e., a wild type ZIF268 finger 2 with the amino acids at positions −1, 2, 3 and 6 replaced with serine residues.

Further constructs are also made. ZIF-F4-GAC comprises finger 4 of TFIIIA inserted between Zif268 and the mutant Zif268 clone GAC (which is a phage selected variant of Zif268 capable of binding GCG GAC GCG). The linkers found naturally in TFIIIA between finger 3 and finger 4 (-NIKICV-) (SEQ ID NO:80) and between finger 4 and finger 5 (-TQQLP-) (SEQ ID NO:81) are retained in both the above peptides. ZIF-F4mut-GAC is identical to ZIF-F4-GAC, except that the linkers flanking finger 4 of TFIIIA are replaced by canonical linkers having the sequence GERP (SEQ ID NO:57). ZIF-mutZnF-GAC is identical to ZIF-ZnF-GAC, except that the TFIIIA finger 4 flanking sequences comprise -NIKICV- (SEQ ID NO:80) and -TQQLP- (SEQ ID NO:81). TF (1-3)-flex-ZIF and ZIF-flex-GAC contain the 20 amino acid sequence: -TG (GSG)$_5$ERP-(SEQ ID NO:82) between their respective three-finger domains.

Example 2

Construction of 3x2F ZGS Zinc Finger Construct

The 3x2F ZGS zinc finger construct is created by linking the third finger of wild-type ZIF to the first finger of the GAC-clone using the peptide sequence GERP. To divide the new peptides into three pairs of fingers, one glycine residue is inserted into the peptide linker between fingers 2 and 3 of wild type ZIF and between fingers 1 and 2 of the GAC-clone. The amino acid and nucleotide sequences of the 3x2F ZGS construct are shown in FIG. 3.

The construction of 3x2F ZGS is described with reference to FIGS. 1 and 3. As shown in FIG. 1, the 3x2F ZGS construct is made by mutagenic PCR of wild type ZIF and GAC-clone templates. ZIF and GAC-clone templates are as described in Choo &Klug (1994), *Proc. Natl. Acad. Sci USA* 91, 11163-11167. Four pairs of oligonucleotide primers, A+a, B+b, C+c and D+d are used. As indicated in FIG. 1, primers A, a, B and b are used to amplify and mutagenise wild type ZIF sequence, while primers C, c, D and d are used to amplify the GAC-clone. The sequences of primers A and d comprise restriction sites for NdeI and NotI respectively, while primers C and b comprise EagI recognition sites. Primers B and D are mutagenic oligonucleotides, whose sequences comprise linker sequences from wild type ZIF (primer B) and GAC (primer D) but with additional nucleotide sequence coding for additional amino acid residues. These linker sequences are chosen from the linker between finger 2 and finger 3 of wild type ZIF (primers a and B) and the linker between finger 1 and finger 2 of the GAC clone (primers c and D). For example, in the case of 3x2F ZGS, primers B and D each include an additional GGC triplet to code for glycine.

To construct the 3x2F ZGS clone, wild type ZIF sequence is amplified by means of primers A, a, B and b, while GAC-clone sequence is amplified by means of primers C, c, D and d. The respective amplification products are then subjected to overlap PCR, with a template fill-in step. Finally, each of the products is amplified with end primers A+b and C+d. The amplification products are then digested with EagI, and ligated at that site. The full length product comprising sequence encoding the 6 finger protein is-then digested with NotI and NdeI, and ligated into NotI/NdeI digested pCITE4b vector (Amersham International Plc). pCITE4b is a eukaryotic expression vector containing a T7 transcription promoter and an internal eukaryotic ribosome translation entry site for protein expression Plasmids containing the zinc-finger constructs are propagated in *E. coli* XL1-Blue (Stratagene) cells.

The sequences of oligonucleotide primer sequences A, a, B, b, C, c, D and d for construction of 3x2F ZGS are shown below, in which restriction sites used in cloning and inserted glycine codons are shown in bold, while annealing sequences for PCR are underlined:

```
Primer A:
                Nde I                      START
5' CAG CCG GCC CAT ATG CGT CTA GAC GCC GCC ATG GCA GAA CGC CCG TAT GCT TG 3'         (SEQ ID NO:1)

Primer a-:
5' CTG TGT GGG TGC GGA TGT GGG T 3'                                                   (SEQ ID NO:2)

Primer B:
                                        Gly
5' ACC CAC ATC CGC ACC CAC ACA GGT GGC GAG AAG CCT TTT GCC 3'                         (SEQ ID NO:3)

Primer b:
                Eag I
5' GCA AGC ATA CGG CCG TTC ACC GGT ATG GAT TTT GGT ATG CCT CTT GCG T 3'               (SEQ ID NO:4)

Primer C:
                Eag I
5' ATG GCA GAA CGG CCG TAT GCT TGC CC 3'                                              (SEQ ID NO:5)

Primer c:
5' GTG TGG ATG CGG ATA TGG CGG GT 3'                                                  (SEQ ID NO:6)

Primer D:
                                        Gly
5' CCC GCC ATA TCC GCA TCC ACA CAG GTG GCC AGA AGC CCT TCC AG 3'                      (SEQ ID NO:7)

Primer d:
                Not I     STOP
5' TCA TTC AAG TGC GGC CGC TTA GGA ATT CCG GGC CGC GTC CTT CTG TCT TAA ATG GAT TTT GG 3'  (SEQ ID NO:8)
```

Example 3

Construction of the ZIF-GAC Fusion Construct

The control construct ZIF-GAC is created by joining the third finger of ZIF to the first finger of the GAC-clone using the peptide sequence described by Kim and Pabo (1998, *Proc. Natl. Acad. Sci. USA* 95, 2812-2817), -LRQKDGERP- (SEQ ID NO:66). This linker is designed to have compatible ends with the adjacent zinc finger sequences. A modification of the method as described above for Example 2 is used. Thus, primers A and b (primer b having the sequence shown below) is used to amplify wild type ZIF, while primers C and d are used to amplify the GAC clone, and the two amplified sequences joined together. The amino acid and nucleotide sequence of the ZIF-GAC fusion construct is shown in FIG. 2. The oligonucleotide primer sequences A, C and d as shown in Example 2 are used for constructing ZIF-GAC, except that primer b has the following sequence:

```
Primer b:
                Eag I     Gly
5' GCA AGC ATA CGG CCG TTC GCC GTC CTT CTG TCT TAA ATG GAT TTT GG 3'     (SEQ ID NO:9)
```

Example 4

Construction of 3x2F ZGL Zinc Finger Construct

The 3x2F ZGXL construct is created using the same method as described above for Example 2, except that amino acid residues GGS are inserted into the linker sequence between fingers 2 and 3 of wild type ZIF and into the linker sequence between fingers 1 and 2 of the GAC-clone. The amino acid and nucleotide sequence of 3x2F ZGL is shown in FIG. 4. The oligonucleotide primer sequences used for constructing 3x2F ZGL are the same as for 3x2F ZGS (Example 2), except for the following:

```
Primer B:
                                Gly Gly Ser
5' ACC CAC ATC CGC ACC CAC ACA GGC GGT TCT GGC GAG AAG CCT TTT GCC 3'    (SEQ ID NO:10)

Primer D:
                                Gly Gly Ser
5' CCC GCC ATA TCC GCA TCC ACA CAG GCG GTT CTG GCC AGA AGC CCT TCC AG 3'    (SEQ ID NO:11)
```

Example 5

Construction of 3x2F ZGXL Zinc Finger Construct

The 3x2F ZGXL construct is created using the same method as described above for Example 2, except that amino acid residues GGSGGS (SEQ ID NO:83) are inserted into the linker sequence between fingers 2 and 3 of wild type ZIF and into the linker sequence between fingers 1 and 2 of the GAC-clone. The amino acid and nucleotide sequence of 3x2F ZGXL is shown in FIG. 5. The oligonucleotide primer sequences used for constructing 3x2F ZGXL are the same as for 3x2F ZGS (Example 2), except for the following:

```
Primer B:
                                Gly Gly Ser Gly Gly Ser
5' ACC CAC ATC CGC ACC CAC ACA GGC GGT TCT GGC GGT TCT GGC GAG AAG CCT TTT GCC 3'    (SEQ ID NO:12)

Primer D:
                                Gly Gly Ser Gly Gly Ser
5' CCC GCC ATA TCC GCA TCC ACA CAG GCG GTT GTG GCG GTT CTG GCC AGA AGC CCT TCC AG 3'    (SEQ ID NO:13)
```

Example 6

Construction of 3x2ZF ZGSL Zinc Finger Construct

The 3x2F ZGSL construct is created using the same method as described above for Example 2, except that a single glycine residue is inserted into the linker sequence between fingers 2 and 3 of wild type ZIF, and amino acid residues GGS are inserted into the linker sequence between fingers 1 and 2 of the GAC-clone. The amino acid and nucleotide sequence of 3x2F ZGSL is shown in FIG. 6. The oligonucleotide primer sequences used for constructing 3x2F ZGSL are the same as for 3x2F ZGS (Example 2), except for the following:

```
Primer D:
                                Gly Gly Ser
5' CCC GCC ATA TCC GCA TCC ACA CAG GCG GTT CTG GCC AGA AGC CCT TCC AG 3'    (SEQ ID NO:11)
```

Example 7

Construction of 3x2F ZGLS Zinc Finger Construct

The 3x2F ZGLS construct is created using the same method as described above for Example 2, except that amino acid residues GGS are inserted into the linker sequence between fingers 2 and 3 of wild type ZIF, and a single glycine residue is inserted into the linker sequence between fingers 1 and 2 of the GAC-clone. The amino acid and nucleotide sequence of 3x2F ZGLS is shown in FIG. 7. The oligonucleotide primer sequences used for constructing 3x2F ZGLS are the same as for 3x2F ZGS (Example 2), except for the following:

```
Primer B:
                                          Gly Gly Ser
5' ACC CAC ATC CGC ACC CAC ACA GGC GGT TCT GGC GAG AAG CCT TTT GCC 3'   (SEQ ID NO:10)
```

Example 8

Protein Expression

The zinc-finger constructs are expressed in vitro by coupled transcription and translation in the TNT Quick Coupled Transcription/Translation System (Promega) using the manufacturer's instructions, except that the medium is supplemented with $ZnCl_2$ to 500 μM. To judge relative protein expression levels, translation products are labelled with $^{35}$S-met and visualised by autoradiography, following SDS-PAGE.

Example 9

Gel Shift Assays

All constructs are assayed using $^{32}$P end-labelled synthetic oligonucleotide duplexes containing the required binding site sequences. The coding strand sequences of the binding sites used in gel shift experiments with peptides containing flexible linkers are shown below in Table 1. Table 2 shows the coding strand sequences of the binding sites used in gel shift experiments with peptides containing structured linkers.

DNA binding reactions contain the appropriate zinc-finger peptide, binding site and 1 μg competitor DNA (poly dI-dC) in a total volume of 10 μl, which contains: 20 mM Bis-tris propane (pH 7.0), 100 mM NaCl, 5 mM $MgCl_2$, 50 μM $ZnCl_2$, 5 mM DTT, 0.1 mg/ml BSA, 0.1% Nonidet P40. Incubations are performed at room temperature for 1 hour.

TABLE 1

The binding site sequences contained within the oligonucleotides used in gel shift experiments with peptides containing flexible linkers.

| Name | Sequence | Putative target for construct | SEQ ID: |
|---|---|---|---|
| bsA | GCG TGG GCG | Wild type ZIF/3x1F Zif | 14 |
| bsB | GCG GAG GCG | GAC-clone (wild-type binding site sequences for fingers 1 and 3, middle finger binds GAC) | 15 |
| bsC | GCG GAC GCG GCG TGG GCG | ZIF-GAC and 3x2F ZGS (contiguous 18 bp site comprising wt ZIF and GAC-clone sites) | 16 |
| bsD | GCG GAG T GCG GCG T TGG GCG | 3x2F ZGL (2-finger/6 bp sites separated by 1 bp) | 17 |

TABLE 1-continued

The binding site sequences contained within the oligonucleotides used in gel shift experiments with peptides containing flexible linkers.

| Name | Sequence | Putative target for construct | SEQ ID: |
|------|----------|-------------------------------|---------|
| bsE | GCG GAG TC GCG GCG TC TGG GCG | 3x2F ZGXL (2-finger/6 bp sites separated by 2 bps) | 18 |
| bsF | GCG GAC T GCG GCG TGG GCG | 3x2F ZGSL (1 bp gap between the binding sites for the first and second fingers of the GAC-clone) | 19 |
| bsG | GCG GAC GCG GCG T TGG GCG | 3x2F ZGLS (1 bp gap between the binding sites for the second and third fingers of wtZIF) | 20 |

TABLE 2

The binding site sequences contained within the oligonucleotides used in gel shift experiments with the TFIIIA (F1-4)-ZIF peptide. The binding site sequences of TFIIIA F1-3 and wild-type ZIF (bold) are separated by between 5 and 10 bps of DNA. The DNA sequence used to separate the binding sites is based on the sequence spanned by TFIIIA-finger 4 in the Internal Control Region of the 5S rRNA gene-TFIIIA's natural binding site. To investigate any possible sequence preference for the region spanned by TFIIIA-finger 4, oligonucleotides containing an altered sequence (bsG1), or 6 adenine residues (bsH1) are designed and tested in bandshifts.

| Name | Sequence | Notes | SEQ ID: |
|------|----------|-------|---------|
| bsA1 | GCGTGGGCGTACCTGGATGGGAGAC | ZIF and TFIIIA (F1-3) binding sites separated by 5 nucleotides | 39 |
| bsB1 | GCGTGGGCGGTACCTGGATGGGAGAC | ZIF and TFIIIA (F1-3) binding sites separated by 6 nucleotides | 40 |
| bsC1 | GCGTGGGCGAGTACCTGGATGGGAGAC | ZIF and TFIIIA (F1-3) binding sites separated by 7 nucleotides | 41 |
| bsD1 | GCGTGGGCGTAGTACCTGGATGGGAGAC | ZIP and TFIIIA (F1-3) binding sites separated by 8 nucleotides | 42 |
| bsE1 | GCGTGGGCGTTAGTACCTGGATGGGAGAC | ZIP and TFIIIA (F1-3) binding sites separated by 9 nucleotides | 43 |
| bsF1 | GCGTGGGCGGTTAGTACCTGGATGGGAGAC | ZIP and TFIIIA (F1-3) binding sites separated by 10 nucleotides | 44 |
| bsG1 | GCGTGGGCGCTTGACGGATGGGAGAC | ZIP and TFIIIA (F1-3) binding sites separated by 6 nucleotides | 45 |
| bsH1 | GCGTGGGCGAAAAAAGGATGGGAGAC | ZIP and TFIIIA (F1-3) binding sites separated by 6 nucleotides | 46 |

TABLE 3

The binding site sequences contained within the oligonucleotides used in gel shift experiments with the GAC-F4-ZIF peptide. The binding site sequences of the GAC-clone and wild-type ZIF (bold) are separated by between 6 and 11 bps of DNA. The DNA sequence spanned in each case is based on the sequence spanned by TFIIIA-finger 4 in the ICR of the 5S rRNA gene, as described above in FIG. 2.

| Name | Sequence | Notes | SEQ ID |
|---|---|---|---|
| bsA2 | GCGTGGGCGTACCTGGCGGACGCG | ZIF and GAC-clone binding sites separated 6 nucleotides | 47 |
| bsB2 | GCGTGGGCGGTACCTGGCGGACGCG | ZIP and GAC-clone binding sites separated by 7 nucleotides | 48 |
| bsC2 | GCGTGGGCGAGTACCTGGCGGACGCG | ZIF and GAC-clone binding sites separated by 8 nucleotides | 49 |
| bsD2 | GCGTGGGCGTAGTACCTGGCGGACGCG | ZIF and GAC-clone binding sites separated by 9 nucleotides | 50 |
| bsE2 | GCGTGGGCGTTAGTACCTGGCGGACGCG | ZIF and GAC-clone binding sites separated by 10 nucleotides | 51 |
| bsF2 | GCGTGGGCGGTTAGTACCTGGCGGACGCG | ZIF and GAC-clone binding sites separated by 11 nucleotides | 52 |

Relative dissociation constants are determined by creating 5-fold serial dilutions of the required peptide and incubating with the appropriate binding site at a constant concentration, which is in general between 0.1 and 0.2 nM. The concentration of protein at which 50% of the binding site is bound is compared for each peptide, with either the full length or part-binding site sequences, to assess the difference in binding affinity. In cases where a non-total bandshift appears only in lanes containing the lowest concentration of peptide, it is likely that the amount of shift is limited by protein concentration rather than by affinity. Therefore, the relative difference in affinity is likely to be greater than that observed and shown.

Example 9A

Active Peptide Concentration

To determine the concentration of zinc finger peptide produced in the in vitro expression system, crude protein samples are used in gel-shift assays against a dilution series of the appropriate binding site. Binding site concentration is always well above the Kd of the peptide, but ranged from a higher concentration than the peptide (80 mM), at which all available peptide binds DNA, to a lower concentration (3-5 mM), at which all DNA is bound. Controls are carried out to ensure that binding sites are not shifted by the in vitro extract in the absence of zinc finger peptide. The reaction mixtures are then separated on a 7% native polyacrylamide gel. Radioactive signals are quantitated by PhosphorImager analysis to determine the amount of shifted binding site, and hence, the concentration of active zinc finger peptide.

Example 9B

Binding Affinity and Specificity

Dissociation constants are determined in parallel to the calculation of active peptide concentration. Serial 3, 4 or 5-fold dilutions of crude peptide are made and incubated with radiolabelled binding site (0.1 pM-500 pM depending on the peptide), as above. Samples are run on 7% native polyacrylamide gels and the radioactive signals quantitated by PhosphorImager analysis. The data is then analysed according to linear transformation of the binding equation and plotted in CA-Cricket Graph III (Computer Associates Inc. NY) to generate the apparent dissociation constants. The Kd values reported are the average of at least two separate studies.

Example 10

Binding Affinity of the Control Construct ZIF-GAC

Figure 9:
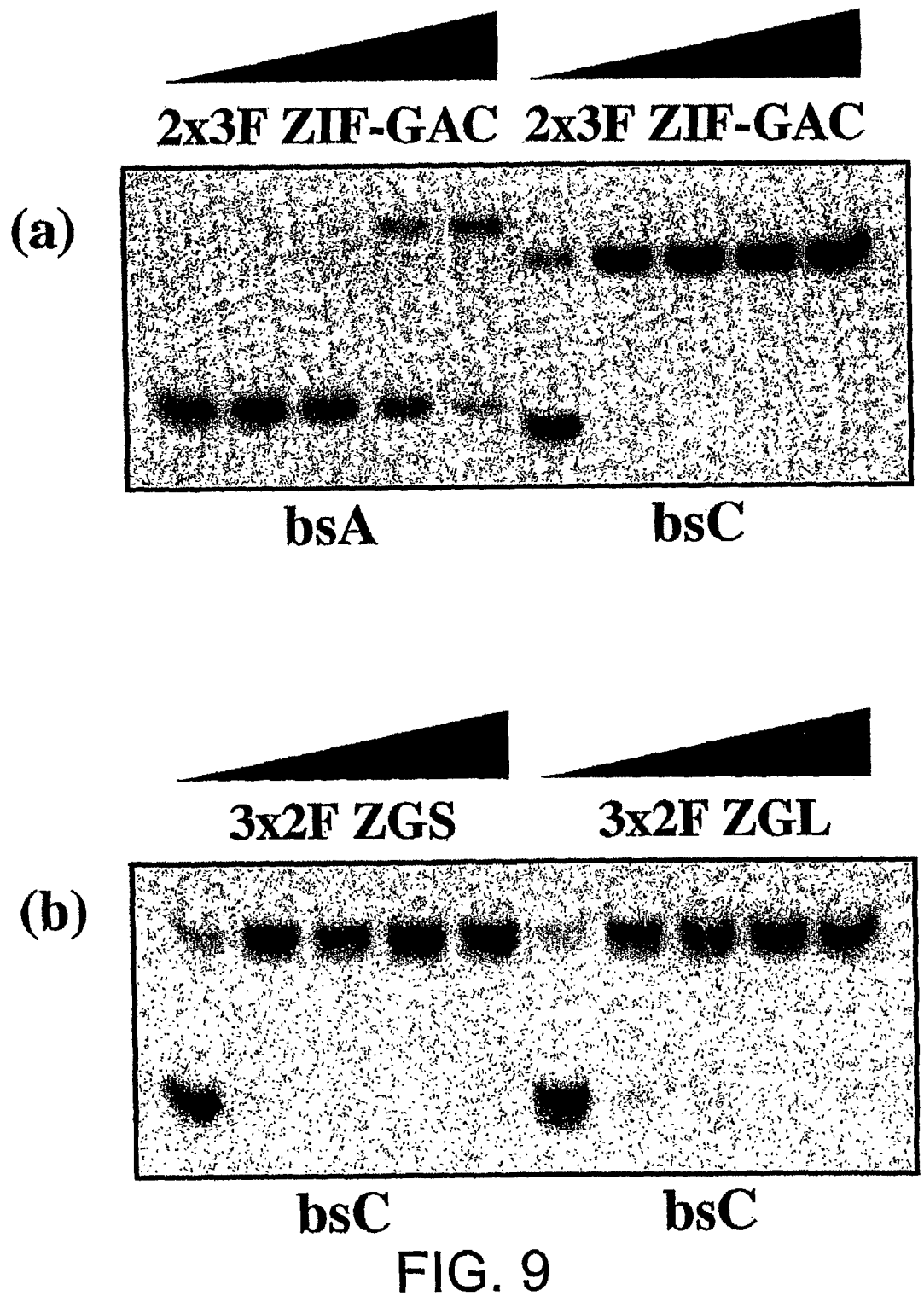
FIG. 9A shows results of gel-shift experiments in which the 2x3F ZIF-GAC peptide is tested for binding to either the 9 bp ZIF site alone (target bsA) or the contiguous 18 bp ZIF-GAC site (target bsC).
FIG. 9B shows results of gel-shift experiments in which the 3x2F ZGS and 3x2F ZGL peptides are tested for binding to target bsC. Serial 5-fold dilutions of peptide are indicated by the black triangle (reactions corresponding to left-hand lanes have less peptide than right-hand lanes), and binding site concentration is 0.13 nM.

In order to compare the binding affinities of the various constructs described here, the ZIF-GAC peptide is used as a control. This peptide may be thought of as a pair of three-finger peptides, and accordingly may be designated as 2x3F. The ZIF-GAC construct is tested for binding to the binding site bsC and to the ZIF binding site alone (bsA). The results are shown in FIG. 9A. FIG. 9A show that the composite site bsC is bound 125-500 fold more tightly than the 9 bp bsA site. This result is comparable to that observed when the experiment of Kim and Pabo (1998, Proc. Natl. Acad. Sci. USA 95, 2812-2817) is repeated using our methods of protein production and bandshift, ie testing the ZIF-NRE peptide for binding to its composite site versus the ZIF wt site.

Example 11

Binding Affinities of Constructs 3x2F ZGS and 3x2F ZGL

The binding affinities of ZIF-GAC, 3x2F ZGS and 3x2F ZGL peptides for a contiguous 18 bp site (bsC) and the 9 bp ZIF binding site (bsA) alone are determined. Serial five-fold dilutions of peptide are made and incubated with 0.13 nM binding site. Significantly, the results show that the 3x2F peptides bind the contiguous 18 bp site at least as tightly as the 2x3F ZIF-GAC peptide (FIGS. 9A and 9B). Moreover, the 3x2F peptides display greater selectivity for the 18 bp site over the 9 bp site, than does the 2x3F peptide. The affinity of the 3x2F peptides for the 9 bp half-site is reduced due to the extended linker sequence between fingers 2 and 3 of ZIF. The expression level of the 3x2F ZGL peptide is approximately half that of the ZIF-GAC and 3x2F ZGS peptides in this study, which accounts for its slightly weaker apparent affinity (expression data not shown).

Example 12

Binding Affinities of Constructs 3x2ZGS, 3x2F ZGL and 3x2F ZGXL

The next experiment is designed to determine whether 3x2F peptides can be used to bind non-contiguous sites with two separate regions of unbound DNA. The constructs used in this study are 3x2F ZGS, 3x2F ZGL and 3x2F ZGXL, and are targeted to the sequences of bsC, bsD and bsE. These sequences can be described as comprising three sets of 6 bp sub-sites, which are either contiguous, separated by 1 bp or separated by 2 bps of unbound DNA.

Figure 10:
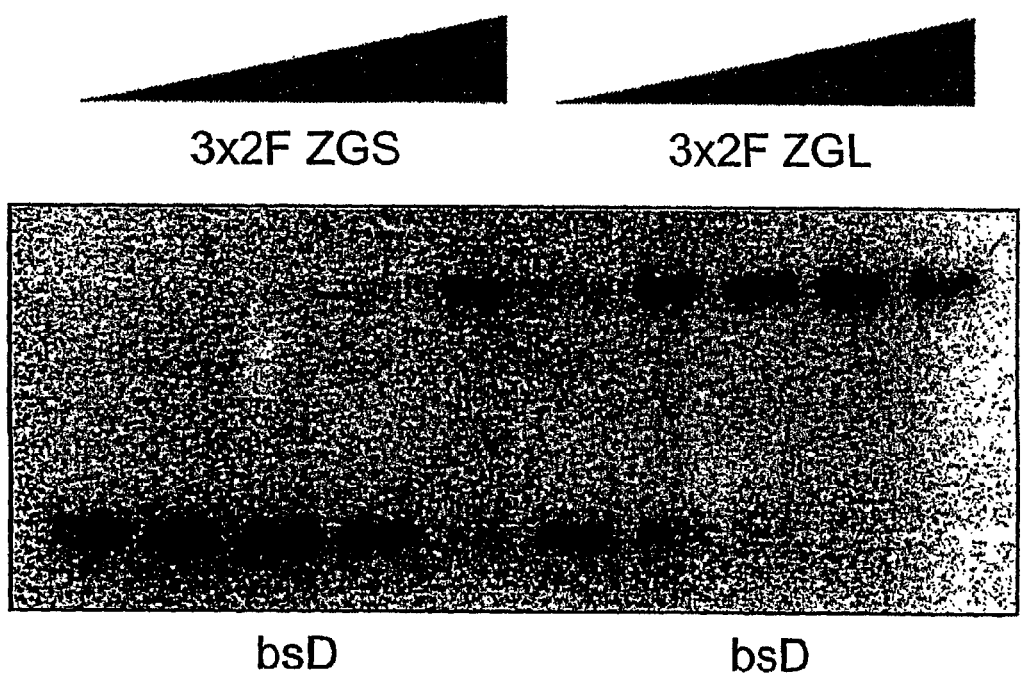
FIG. 10 shows results of gel-shift experiments in which 3x2F ZGS and 3x2F ZGL peptides are tested for binding to the non-contiguous target sequence, bsD. Serial 5-fold dilutions of peptide are indicated by the black triangle (reactions corresponding to left-hand lanes have less peptide than right-hand lanes), and binding site concentration is 0.13 nM.

As shown in FIG. 9B, the results demonstrate that the 3x2F ZGS and 3x2F ZGL peptides bind the contiguous 18 bp site (bsC) equally tightly (taking into account the different protein expression levels). We also find that the 3x2F ZGL peptide can bind the non-contiguous site (bsD) as tightly as it does the contiguous 18 bp site bsC (see FIGS. 9B and 10). However, the 3x2F ZGS peptide binds bsD over 125-fold more weakly than it does bsC (compare left hand panels of FIG. 9B and FIG. 10). This is in accordance with the fact that the short, five amino acid synthetic linkers within 3x2F ZGS are unable to span 1 bp of DNA, and therefore the 3x2F ZGS peptide binds the bsD site through only one pair of fingers.

Figure 11:
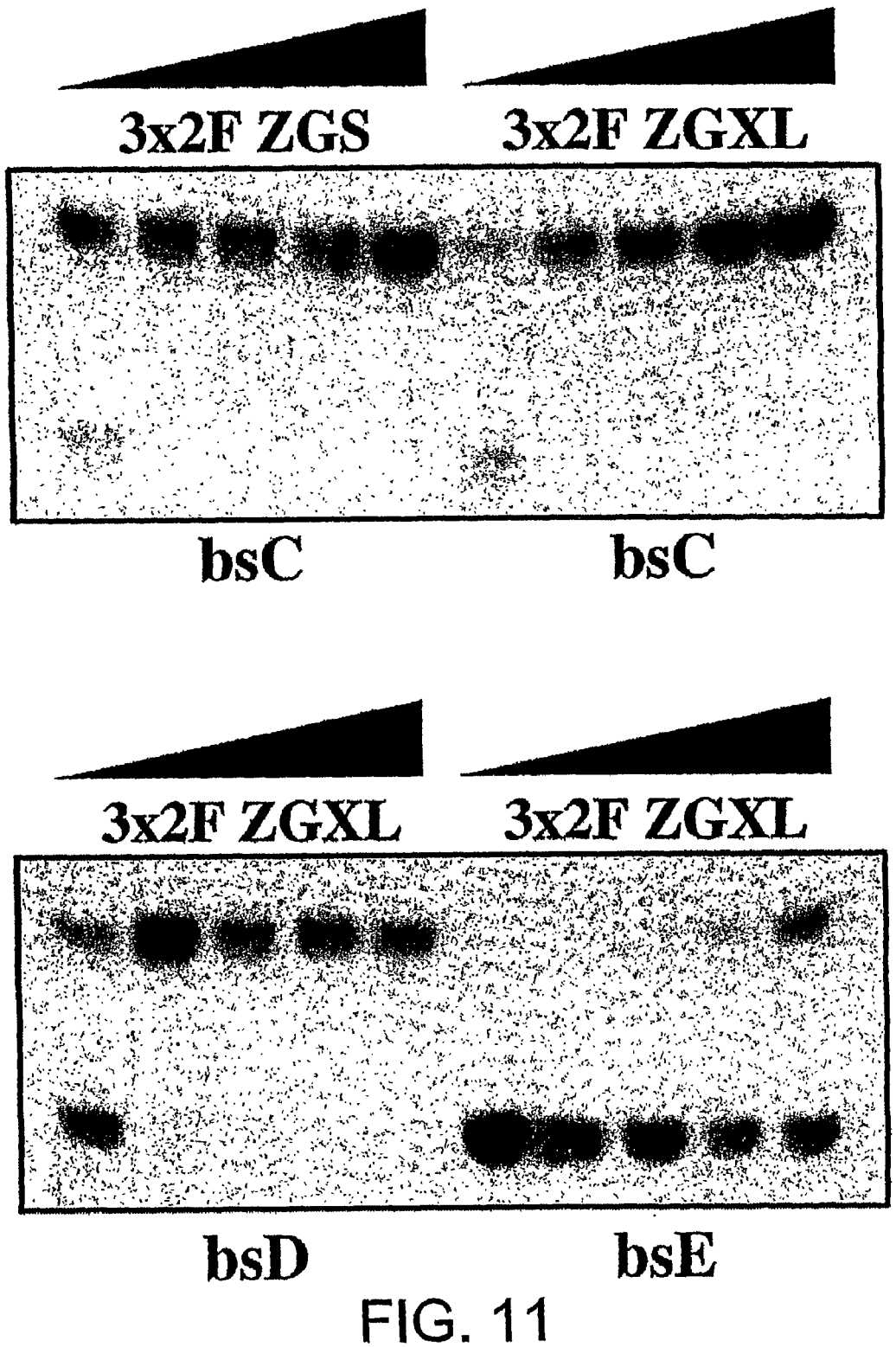
FIG. 11 shows results of gel-shift experiments in which 3x2F ZGXL peptide is tested for binding to the contiguous and non-contiguous target sequences bsC, bsD and bsE. Binding of 3x2F ZGS peptide to bsC is also shown for comparison. Serial 5-fold dilutions of peptide are indicated by the black triangle (reactions corresponding to left-hand lanes have less peptide than right-hand lanes), and binding site concentration is 0.13 nM.

FIG. 11 shows that the 3x2F ZGXL peptide can bind the non-contiguous site (bsD) as tightly as it does the contiguous 18 bp site bsC. 3x2F ZGXL binds the non-contiguous site bsD approximately as tightly as the 3x2F ZGS peptide binds the contiguous 18 bp site, bsC. However, the 3x2F ZGXL peptide binds bsE (containing 2 base pair gaps between target subsites) approximately 500-fold less tightly than it does bsC and bsD, as shown in FIG. 11. This is presumably because it can only bind bsE through 2 fingers.

Example 13

Binding Affinities of Constructs 3x2F ZGSL and 3x2F ZGLS

As a continuation of the above experiment, 3x2F peptides are constructed with different combinations of engineered linkers within a ZIF-GAC fusion peptide. In the construct 3x2F ZGSL the first two pairs of fingers are separated by a short (-GG$^E$/$_Q$KP-) (SEQ ID NO:60 or 61) linker and the second two pairs are separated by a longer (-GGSG$^E$/$_Q$KP-) (SEQ ID NO:62 or 63) linker (see FIG. 6). In the construct 3x2F ZGLS the first two pairs of fingers are separated by a long (-GGSG$^E$/$_Q$KP-) (SEQ ID NO:62 or 63) linker and the second two pairs are separated by a shorter (-GG$^E$/$_Q$KP-) (SEQ ID NO:60 or 61) linker (see FIG. 7).

Figure 12:
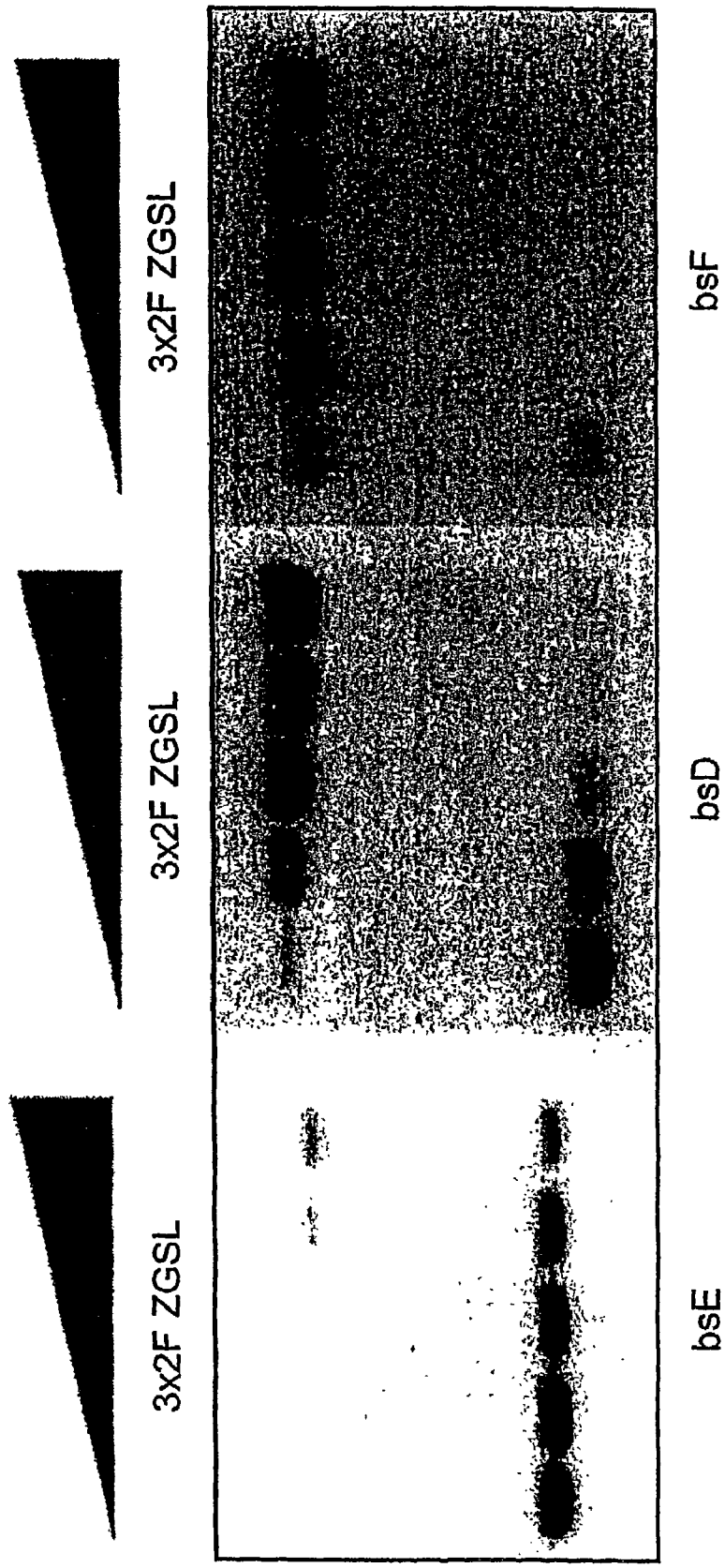
FIG. 12 shows results of gel-shift experiments in which 3x2F ZGSL peptide is tested for binding to the 3x2F ZGXL binding site bsE, the 3x2F ZGL binding site bsD and the 3x2F ZGSL binding site bsF. Serial 5-fold dilutions of peptide are indicated by the black triangle (reactions corresponding to left-hand lanes have less peptide than right-hand lanes), and binding site concentration is 0.10 nM.

These two peptides are tested for binding to binding sites bsF, which has a 1 bp gap between the first two 6 bp subsites, and bsG which has a 1 bp gap between the second two 6 bp subsites (see Table 1). As expected, given the previous observations, the results demonstrate that the binding of arrays of zinc finger pairs can be tailored to suit the length of gap between 6 bp binding subsites. FIG. 12 shows the results of a gel shift experiment testing the binding of 3x2F ZGSL peptide to bsD, bsE and bsF, which is through 4, 2 and 6 fingers respectively. From the binding patterns it can be seen that the affinity of the 6-finger bound complex (3x2F ZGSL on bsF, right hand panel) is approximately 10-fold higher that the 4-finger bound complex (3x2F ZGSL on bsD, middle panel) and 125-500 fold stronger than the 2-finger bound complex (3x2F ZGSL on bsE, left hand panel).

Similarly, 3x2F ZGLS peptide is tested for binding to bsD, bsE and bsG, which is through 4, 2 and 6 fingers respectively. It is found that the affinity of binding of 3x2F ZGLS is strongest for bsG, followed by bsD and lastly bsE, with relative affinities similar to those obtained from 3x2F ZGSL above.

Example 13A

Binding Affinity of 3x2F ZGS and Zif-GAC

A preliminary-experiment is conducted using the three-finger Zif268 peptide against its 9 bp binding site as a form of 'protocol calibration'. This gives a value for the Kd of Zif268 of 0.45 nM, which is within the range expected for this peptide.

To determine the binding specificity of different styles of six-finger peptides, the 3x2F ZGS and Zif-GAC peptides re first used in gel-shift experiments with the 9 bp Zif268 half-site, and a full 18 bp binding site (bsC, also termed "123456"). These results show that the 3x2F ZGS and 2x3F Zif-GAC peptides bind their full-length target site with similar affinities, of 0.6 and 1.4 pM respectively (Table 4 below). However, their affinities for the Zif268 half-site are dramatically different. The 2x3F Zif-GAC peptide binds with an affinity of approximately 2.2 nM (which is within the range expected), but the 3x2F ZGS peptide binds with an affinity of about 110 nM. This affinity is so weak that it is difficult to quantify using this system. From these data it can be seen that the 3x2F peptide discriminates between the two sites over 100-fold more strongly than the 2x3F peptide.

Figure 25:
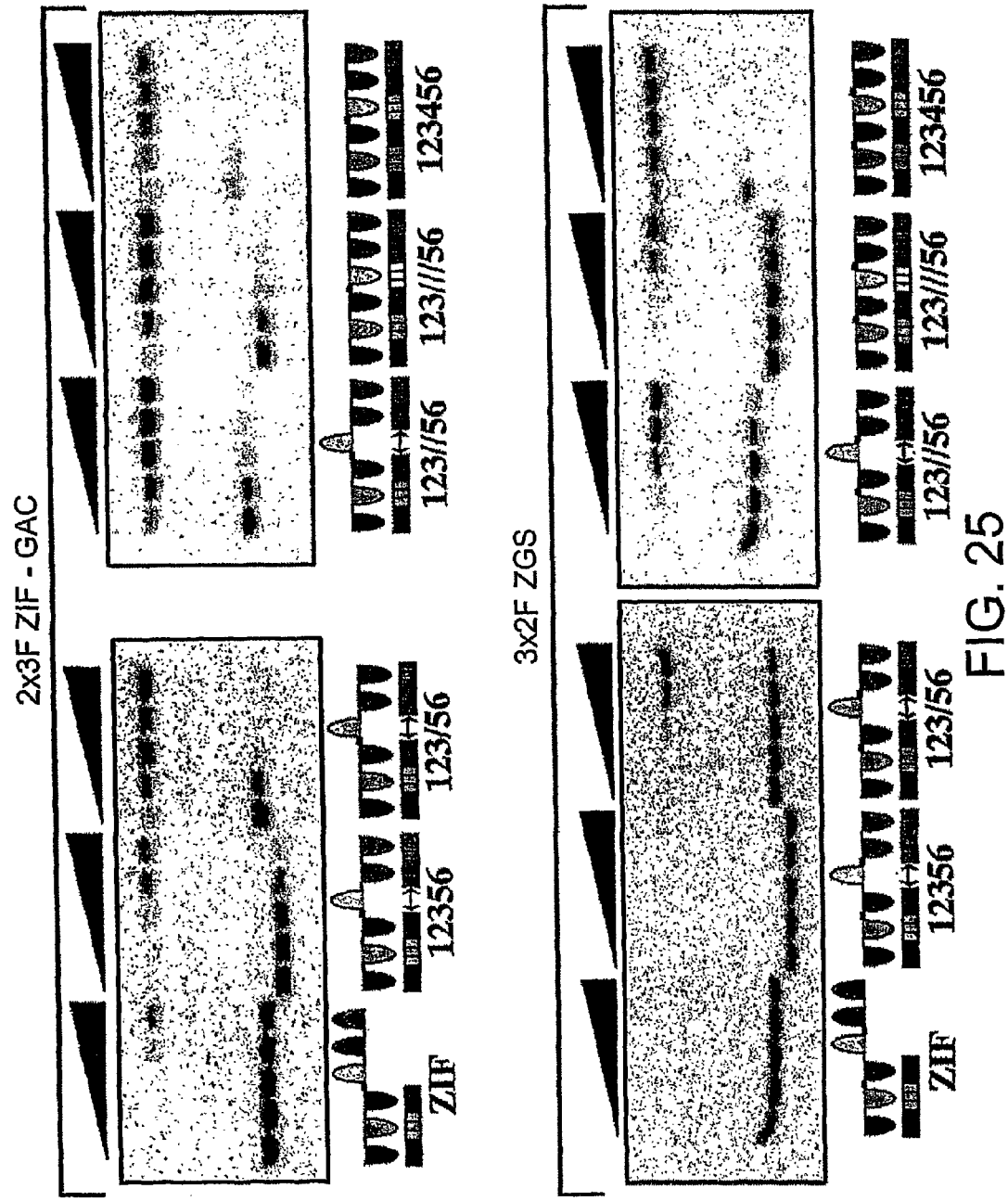
FIG. 25. A selection of DNA binding studies by gel-shift assay. The gels are designed to give a comparison between the binding affinities of the 2x3F Zif-GAC and 3x2F ZGS peptides, and are not necessarily the gels used to quantify binding affinity. For example, the amount of 123456 binding site shifted by each peptide is limited by protein concentration, rather than Kd. Top: 5-fold dilutions of 2x3F Zif-GAC (from 800 pM-1.3 pM), against 2 pM binding sites. Bottom: 5-fold dilutions of 3x2F ZGS (from 700 pM-1.1 pM), against 2 pM binding sites. The proposed binding modes of the zinc finger peptides for each binding site is illustrated under each gel image.

To further study the specificity of the two constructs the 3x2F and 2x3F peptides are targeted against binding sites that have been mutated in the region normally bound by finger 4. These results show that the 3x2F ZGS peptide binds to the site with a 3 bp region mutated, 123///56, with an affinity of 890 pM. Meanwhile, it binds to a site with this 3 bp region deleted, 12356, with an affinity of 22 nM (see Table 5 below). Its affinities for sites with 1 or 2 bp deletions are 270 pM and 630 pM respectively. Hence, the affinities of 3x2F ZGS for these mutant sequences are between 450 and 37,000-fold weaker than for the correct binding sequence. In contrast, the 2x3F Zif-GAC peptide binds 123///156, 123//56, and 123/56 with affinities of 15, 14 and 14 pM respectively. This is just 10-fold weaker than that for its correct binding site. The 2x3F Zif-GAC peptide shows a further reduction in affinity for the 12356 binding site, but this sequence is still bound more than 60 times stronger than it is bound by 3x2F ZGS. The gel-shift data in FIG. 25 demonstrates the relative binding affinities of the 2x3F Zif-GAC and 3x2F ZGS peptides for these binding sites. All this data serves to emphasise the enhanced specificity of the 3x2F construct for sequences that resemble its correct target site. The gel-shift data of FIG. 25 demonstrates the relative affinities of the 3x2F ZGS and 2x3F Zif-GAC peptides for the target sites.

TABLE 4

The binding site sequences used in gel-shift experiments with the 3 × 2F ZGS and 2 × 3F Zif-GAC peptides and the binding affinities obtained.

| Binding Site Name | Binding Site Sequence* | Apparent Kd (pM) 3 × 2F ZGS | Apparent Kd (pM) 2 × 3F Zif-GAG |
|---|---|---|---|
| bsA (ZIF) | GCG TGG GCG | $1.1 \times 10^5$ | 2200 |
| 123456 (bsG) | GCG GAC GCG GCG TGG GCG | 0.6 | 1.4 |
| 123///56 (bs4) | GCG GAC ATC GCG TGG GCG | 890 | 15 |
| 123//56 (bs3) | GCG GAC TC GCG TGG GCG | 270 | 14 |
| 123/56 (bs2) | GCG GAC T GCG TGG GCG | 630 | 14 |
| 12356 | GCG GAC GCG TGG GCG | $2.2 \times 10^4$ | 360 |

*Binding site residues which are mutated (and subsequently deleted) are underlined.

Example 13B

Binding of Non-Contiguous Sequences

A second set of binding studies is conducted to demonstrate the ability of the 3x2F peptides to accommodate one or more regions of unbound DNA within their recognition sequence. First the 3x2F ZGS and ZGL peptides are titrated against 12/34/56 (three 6 bp subsites separated by 1 bp, which is represented by a single '/' in the binding site name) and 12//34//56 (three 6 bp subsites separated by 2 bps) binding sites. The results in Table 5 show that the 3x2F ZGS peptide—which is designed to target only the contiguous 123456 site—is unable to accommodate either 1 bp or 2 bp gaps between the two-finger subsites. The 3x2F ZGL peptide, however, binds the 12/34/56 site with an affinity of approximately 5 pM, but is also unable to bind tightly to the site with 2 bp gaps. Next, the 3x2F ZGSL and 3x2F ZGLS peptides are targeted against the three non-contiguous sequences: 1234/56, 12/3456 and 12//34//56. These sites are bound by the 3x2F ZGSL peptide with affinities of approximately 3 pM, 73 pM and 12 nM, which is in accordance with the binding of 6, 4 and 2 fingers respectively. 3x2F ZGLS show a similar trend in binding affinities. These experiments demonstrate that 3x2F peptides can bind contiguous 18 bp sites, but are also unique amongst the six finger peptides reported to date, in being able to bind sequences with two regions of unbound DNA with high affinity.

TABLE 5

The binding site sequences used in gel-shift experiments with the 3 × 2F peptides and the binding affinities determined.

| Binding Site Name | Binding Site Sequence* | Apparent Kd† (pM) 3 × 2F ZGS | Apparent Kd† (pM) 3 × 2F ZGL | Apparent Kd† (pM) 3 × 2F ZGSL | Apparent Kd† (pM) 3 × 2F ZGLS |
|---|---|---|---|---|---|
| 123456 (bsC) | GCG GAC GCG GCG TGG GCG | 0.6 | 0.9 | ND | ND |
| 12/34/56 (bsD) | GCG GAC T GCG GCG T TGG GCG | $1.8 \times 10^4$ | 5 | 110 | 120 |
| 12//34//56 (bsE) | GCG GAG TC GCG GCG TC TGG GCG | ND | $1.1 \times 10^4$ | $1.2 \times 10^4$ | $1.2 \times 10^4$ |

TABLE 5-continued

The binding site sequences used in gel-shift experiments with the 3 × 2F peptides and the binding affinities determined.

| Binding Site Name | Binding Site Sequence* | Apparent Kd† (pM) | | | |
|---|---|---|---|---|---|
| | | 3 × 2F ZGS | 3 × 2F ZGL | 3 × 2F ZGSL | 3 × 2F ZGLS |
| 1234/56 (bsF) | GCG GAC T GCG GCG TGG GCG | 54 | ND | 3 | 89 |
| 12/3456 (bsG) | GCG GAC GCG GCG T TGG GCG | 77 | ND | 73 | 5 |

*Designed gaps in the target sequence are shown in bold.
†ND (not done) represents experiments for which Kds are not calculated.

It appears that the more rigid nature of the 2x3F Zif-GAC peptide means that a mutation in the binding site of one finger is 'felt' only by that finger, so that the 123///56 site is bound with the extremely high affinity of 15 pM. In contrast, the results above show that the more sensitive design of the 3x2F peptides mean that a mutation in the binding sequence of a single finger weakens the entire two-finger unit. Thus, the 3x2F ZGS peptide binds the same site with an affinity of 890 pM. The large reduction in affinity of the 3x2F ZGS peptide for the Zif268 half-site must be attributed to the extended linker sequence between fingers 2 and 3. Presumably this linker reduces the co-operative binding effect of the adjacent fingers, such that finger 3 of the peptide adds nothing to the binding of the half-site. Meanwhile, the unbound fingers probably 'drag' on the complex to help pull the peptide off the DNA. The higher affinity of the 3x2F peptides for other sites that are bound by only two fingers (such as the 3x2F ZGS peptide against the 12/34/56 site) presumably arises because there are three separate two-finger binding sites present in the sequence.

Example 14

Binding Affinities of Construct 3x1F ZIF

A peptide denoted 3x1F ZIF (FIG. 8) is constructed by inserting a single glycine residue within each of the natural linkers in the wt ZIF gene. A further extension of this design is also used to create 6x1F ZG, which is a six-finger ZIF-GAC clone containing a glycine insertion within every linker peptide. The binding affinity of the 3x1F peptide for the 9 bp ZIF site (bsA) is tested, and the construct is shown to bind the substrate.

Example 15

Structured Linkers

The experiments described in the following Examples seek to increase the utility of poly-zinc finger peptides by creating fusion peptides that are able to bind with high affinity to target sequences in which their binding subsites are separated by long (up to 10 bp) stretches of DNA. The Examples utilise structured linkers which are believed to show a preference for a particular length of DNA span, so that they maintain a high degree of specificity. The crystal structure of the first six fingers of TFIIIA bound to DNA (Nolte, R. T., Conlin, R. M., Harrison, S. C. & Brown, R. S. (1998) *Proc. Natl. Acad. Sci. USA* 95,2938-2943), indicate that that TFIIIA finger 4 may be a suitable candidate for a structured linker to span long (>5 bp) stretches of DNA.

A fusion peptide comprising the first four fingers of TFIIIA and the three fingers of Zif268, called TF(1-4)-ZIF, is first created. This is shown to bind DNA with high affinity and showed a preference for sites containing 7 or 8 bps of non-bound DNA. In contrast, a similar construct that contains a 20 residue flexible linker, TF(1-3)-flex-ZIF, is seen to bind its full-length target sites somewhat weaker. The data in these Examples suggests that TFIIIA finger 4 is a suitable 'structured' linker for spanning long stretches of DNA, and furthermore, that TF(1-4)-ZIF would make a good scaffold for 'designer' transcription factors that bind DNA with 7 or 8 bps of non-bound DNA.

The Examples also test the ability of a zinc finger module from Zif268 to act as a structured linker. A zinc finger from Zif268 is mutated to make it non sequence—specific, and then used to link the three wild-type fingers of Zif268 to a three-finger mutant of Zif268 (GAC). This 'serine-finger' is expected to sit in the major groove, spanning 3 or 4 bps of DNA. Surprisingly, this new peptide is found to be able to bind with similar affinity to the continuous 18 bp sequence comprising the Zif268 and GAC sites, and to all the non-contiguous sites with 1-10 bp gaps. The fact that this peptide can bind tightly to the contiguous binding site and the sites with just 1 or 2 bp gaps suggests that the 'serine-finger' is able to flip out of the major groove to make space for the binding of its neighbouring fingers. This data indicates that within a zinc finger array redundant fingers can make way for stronger DNA-binding domains. When the binding subsites are separated by 7-10 bps of DNA it is likely that the redundant finger lies across the surface of the DNA, in a manner analogous to TFIIIA finger 4 (15).

The Examples also describe a fusion construct, ZIF-F4-GAC, which uses TFIIIA finger 4 as a linker between two Zif-type domains. This peptide displays little discrimination for the length of DNA span separating the binding subsites, although a trend in the binding affinities of the peptide is apparent. All peptides connected by zinc finger modules show a preference for sequences containing 3 bp or over 6 bp gaps.

These probably correspond to binding modes when the zinc finger-linker is sat 'normally' in the major groove, or able to bridge the minor groove.

It has been proposed that the relatively hydrophobic linkers flanking TFIIIA finger 4 may constrain finger 4 into its orientation across the minor groove, as observed in the crystal structure of Nolte et al. (1998). Hence, the Examples also describe investigations into the conformational freedom of zinc fingers by swapping the linker sequences flanking wild-type TFIIIA finger 4 and the 'serine-finger'. It is found that the linker sequences flanking TFIIIA finger 4 only confer a small degree of structural rigidity, which is most apparent when the finger is forced to take up unfavourable conformations.

A predicted benefit of using structured linkers is that of increased binding affinity over peptides containing long, flexible linkers. This is confirmed by the Examples which disclose binding results from the two peptides containing 20 residue flexible linkers, which are found to bind their full-length targets between 3 and 10-fold weaker than peptides with structured linkers.

Poly-zinc finger peptides are likely to become increasingly important in gene therapy and the creation of transgenic organisms. Given the difficulty of engineering zinc finger peptides to bind to all possible DNA sequences (Choo, Y. & Klug, A. (1994) *Proc. Natl. Acad, Sci. USA* 91, 11168-11172; Segal, D. T., Dreier, B., Beerli, R. R & Barbas, C. F. III (1999) *Proc. Natl. Acad. Sci. USA* 96, 2758-2763.), it is advantageous to synthesise peptides capable of spanning long regions of DNA, while still binding with high affinity. This will allow the selection of favourable DNA target sites that may be several nucleotides apart. The Examples show that 'structured' linkers may be incorporated into zinc finger fusion peptides. These allow the separate DNA-binding domains to bind with high affinity to sites separated by 1 to 10 bps of non-bound DNA. The ability of these structured-linker fusion peptides to span such long stretches of DNA is particularly advantageous for the targeting of natural promoter sequences. For example, the zinc finger protein, Sp1, binds GC box DNA, which can appear in multiple copies in the promoter sequences upstream of a variety of cellular and viral genes (Kadonaga, J. T., Jones, K. A. & Tjian, R. (1986) *Trends Biochem. Sci.* 11, 20-23; Bucher, P. (1990) *J. Mol. Biol.* 212, 563-578). Similarly, the promoter for the HSV40 early genes contains three 21 bp repeats which include GC boxes. Linking zinc finger peptides that recognise such regions could create powerful 'designer' transcription factors. TFIIIA finger 4 may be a particularly useful 'structured' linker as it shows a marked preference for 7 or 8 bp DNA spans.

The Examples also indicate that weakly binding zinc fingers are able to 'flip' in or out of the DNA major groove to accommodate neighbouring fingers within the DNA-binding domain. This means that certain zinc finger arrays will bind reasonably tightly to truncated or mutated binding sites. This feature of zinc-finger arrays may be taken advantage of, for instance to engineer zinc fingers which bind to a series of related, but different binding sites. Nature almost certainly takes advantage of this phenomenon to evolve zinc finger transcription factors that regulate multiple genes from non-identical promoters. Furthermore, many natural polydactyl proteins that have been isolated contain zinc fingers whose roles are not yet understood. For example, GL1 contains five tandem zinc fingers, but in the crystal structure of this protein only two of these bind to DNA in the classical-base specific-manner (Pavletich, N. P. & Pabo, C, O. (1991) *Science* 261, 1701-1707). The results presented in the Examples also suggest that there may be a broad repertoire of roles for zinc finger domains within the cell. The Examples also show that polydactyl peptides comprising flexible linkers may be created that bind with far greater specificity than previously designed six-finger peptides.

Example 15A

Construction of TFIIIA(F1-4)-ZIF Zinc Finger Construct

The TFIIIA(F1-4) construct is made by fusing the first four fingers of TFIIIA N-terminally to the three fingers of wt ZIF. The natural linker between fingers 4 and 5 of TFIIIA is used as the linker between TFIIIA finger 4 and ZIF finger 1. However, the construct is designed such that the entire TFIIIA finger 4 region acts as a structured linker between TFIIIA fingers 1-3 (which bind DNA) and wt ZIF fingers 1-3 (which also bind DNA).

Figure 13:
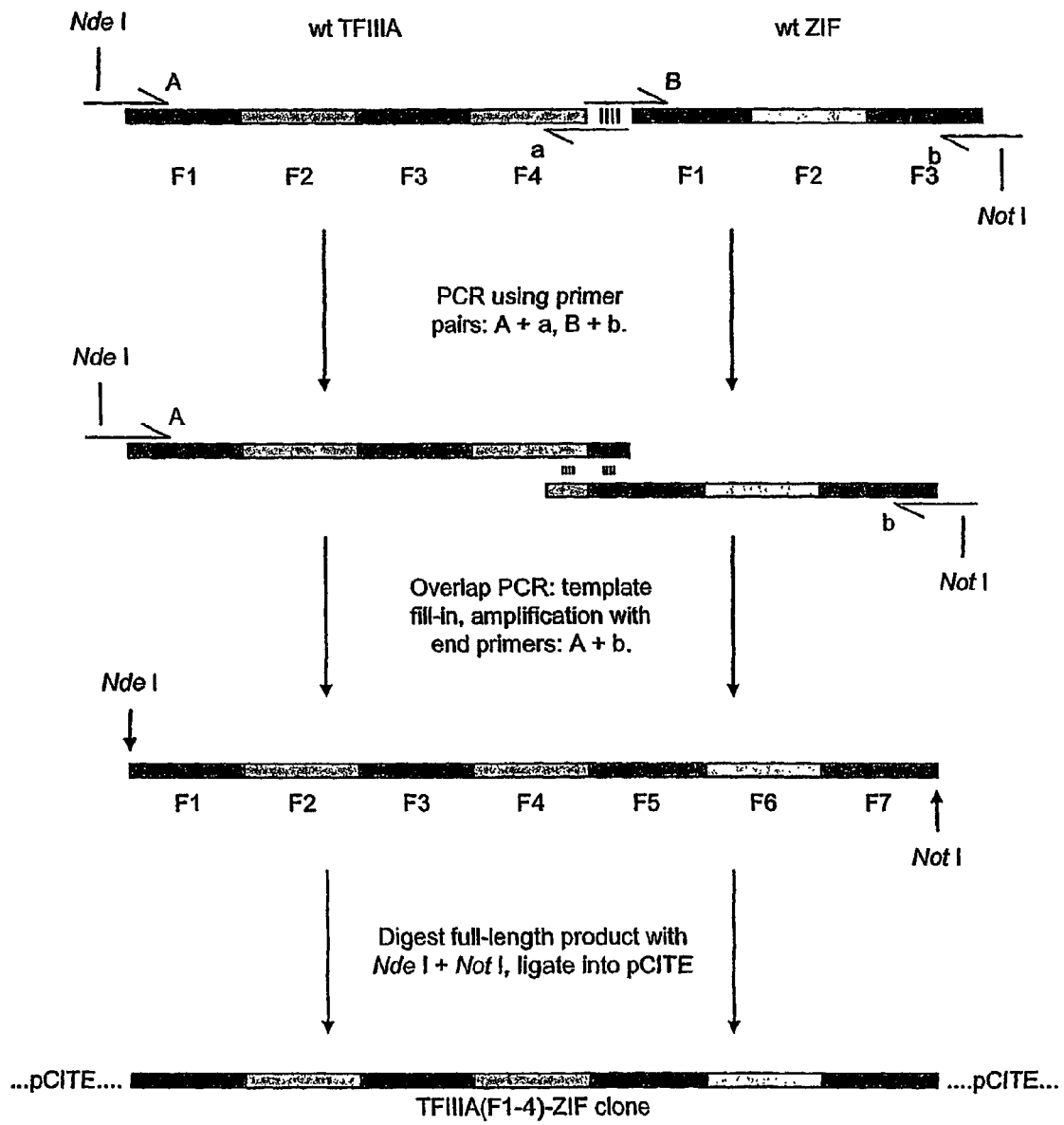
FIG. 13 is a schematic diagram showing the construction of the TFIIIA(F1-4)-ZIF zinc finger construct described here. Step 1: PCR using primer pairs A+a and B+b on wild type TFIIIA and wild type ZIF templates respectively. Step 2: Overlap PCR; template fill-in and amplification with end primers A+b. Step 3: Digestion with EagI, ligation of resulting products; digestion of full-length product with NdeI+NotI, ligation into pCITE vector.

The construction of TFIIIA(F1-14) is described with reference to FIGS. 13 and 15. As shown in FIG. 13, the TFIIIA (F1-4) construct is made by PCR using two pairs of primers A+a and B+b to amplify wild type TFIIIA and wild type ZIF templates respectively. Primers A and b comprise restriction sites for NdeI and NotI respectively. The respective amplification products are then subjected to overlap PCR, with a template fill-in step. Finally, the products are amplified with end primers A+b, digested with NotI and NdeI, and ligated into NotI/NdeI digested pCITE-4b vector (Amersham International Plc).

```
Primer A:                                                    (SEQ ID NO:29)
                                              Nde I
5' ACT TCG GAA TTC GCG GCC CAG CCG GCC CAT
ATG GGA GAG AAG GCG CTG CCG GTG 3'

Primer a:                                                    (SEQ ID NO:30)
5' GCA AGC ATA CGG CAG CTG CTG TGT GTG ACT G 3'

Primer B:                                                    (SEQ ID NO:31)
5' ACA CAG CAG CTG CCG TAT GCT TGC CCT GTC GAG TCC 3'

Primer b:                                                    (SEQ ID NO:32)
                                       Not I   STOP
5' GAG TCA TTC AAG CTT TGC GGC CGC TTA GTC CTT CTG TCT TAA ATG GAT TTT GG 3'
```

Example 16

Construction of GAC-F4-ZIF Zinc Finger Construct

The GAC-F4-ZIF construct is made by joining the GAC-clone to the N-terminus of wt ZIF, using the entire TFIIIA finger 4 peptide (including its natural flanking linker sequences) as a structured linker.

Figure 14:
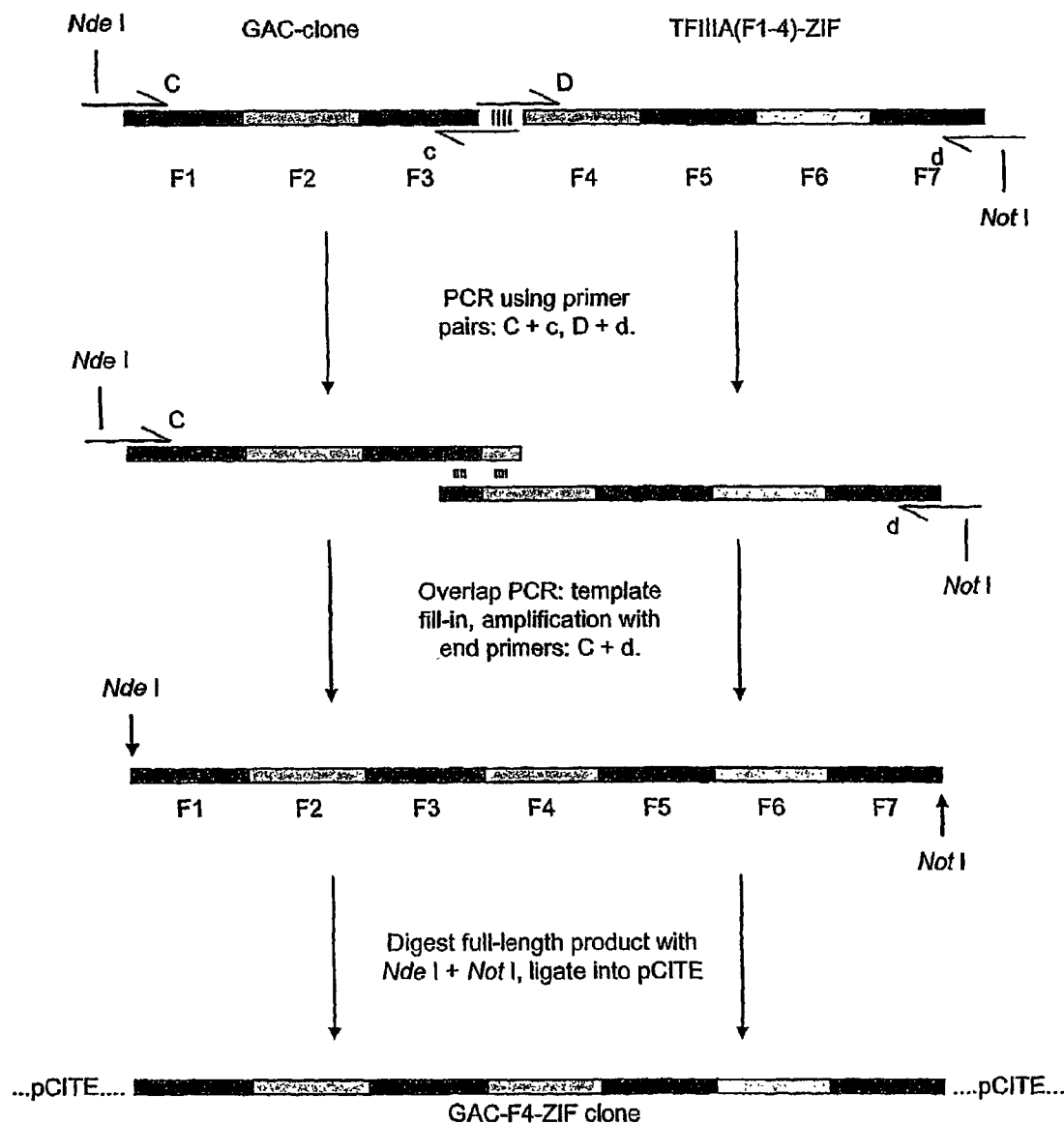
FIG. 14 is a schematic diagram showing the construction of the GAC-F4-ZIF zinc finger construct described here. Step 1: PCR using primer pairs C+c and D+d on GAC clone and TFIIIA(F1-4)-ZIF templates respectively. Step 2: Overlap PCR; template fill-in and amplification with end primers C+d. Step 3: Digestion with EagI, ligation of resulting products; digestion of full-length product with NdeI+NotI, ligation into pCITE vector.

The construction of GAC-F4-ZIF is described with reference to FIGS. 14 and 16. As shown in FIG. 14, the GAC-F4-ZIF construct is made by PCR using two pairs of primers C+c and D+d to amplify the GAC clone and TFIIIA(F1-4) templates respectively. Primers C and d comprise restriction sites for NdeI and NotI respectively. The respective amplification products are then subjected to overlap PCR, with a template fill-in step. Finally, the products are amplified with end primers C+d, digested with NotI and NdeI, and ligated into NotI/NdeI digested pCITE4b vector (Amersham International Plc).

```
Primer C:                                                              (SEQ ID NO:33)
                                        Nde I
5' ACT TCG GAA TTC GCG GCC CAG CCG GCC CAT ATG GCA GAA CGC CCG TAT GCT TG 3'

Primer c:                                                              (SEQ ID NO:34)
5' CAC ATA GAC GCA GAT CTT GAT GTT ATG GAT TTT GGT ATG CCT CTT GCG 3'

Primer D:                                                              (SEQ ID NO:35)
5' CAT AAC ATC AAG ATC TGC GTC TAT GTG 3'

Primer d:                                                              (SEQ ID NO:36)
                                        Not I       STOP
5' GAG TCA TTC AAG CTT TGC GGC CGC TTA GTC CTT CTG TCT TAA ATG GAT TTT GG 3'
```

Example 17

Construction of ZIF-ZnF-GAC Zinc Finger Construct

To create the ZIF-ZnF-GAC construct, primers A+b and C+d are used to amplify the wild type ZIF and GAC clone sequences, respectively. These are then digested with Eag I to create sticky ends. Next, the "neutral" zinc finger (ZnF) is produced by annealing the following complementary oligonucleotides: 5' GG CCG TTC CAG TGT CGA ATC TGC ATG CGT AAC TTC AGT TCT AGT AGC TCT CTT ACC AGC CAC ATC CGC ACC CAC ACA GGT GAG C 3' (SEQ ID NO: 37) and 5' GG CCG CTC ACC TGT GTG GGT GCG GAT GTG GCT GGT AAG AGA GCT ACT AGA ACT GAA GTT ACG CAT GCA GAT TCG ACA CTG GAA C 3' (SEQ ID NO:38), which create EagI sites at each end. The complete ZIF-ZnF-GAC construct is finally generated by joining the "neutral" finger to the EagI cut ZIF and GAC sequences. This construct is then digested with NdeI and NotI and ligated into similarly digested pCITE-4b vector (Amersham International Plc).

Example 17A

Construction of ZIF-F4-GAC, ZIF-F4mut-GAC, ZIF-mutZnF-GAC, TF(1-3)-flex-ZIF and ZIF-flex-GAC

ZIF-F4-GAC and ZIF-F4mut-GAC

The ZIF-F4-GAC and ZIF-F4mut-GAC constructs are made by three separate PCR amplifications of the three fingers of Zif268, the three fingers of a Zif268 mutant peptide (GAC), and the fourth finger of TFIIIA. Two sequential overlap PCR reactions are then used to fuse the separate units together, creating seven-finger constructs.

ZIF-mutZnF-GAC

The ZIF-mutZnF-GAC construct is made by PCR amplification of the three-fingers of wt Zif268 and the Zif268 mutant (GAC), creating Eag I sites at their C- and N-termini respectively. The structured linker, ZnF, described above in Example 17, is inserted between the Eag I cut ZIF and GAC three-finger units to create the complete seven-finger construct. The ZIF-mutZnF-GAC clone IS made by PCR amplification of the ZIF, GAC, and ZnF structured linker fragments to create mutant ends. These three fragments are joined by two sequential rounds of overlap PCR as above.

TF(1-3)-flex-ZIF and ZIF-flex-GAC

The TF(1-3)-flex-ZIF and ZIF-flex-GAC constructs are created by PCR amplification of the first three fingers of TFIIIA, the three fingers of Zif268 or the three fingers of the GAC-clone—using appropriate oligonucleotides—which are designed to generate the flexible 20 amino acid linker peptide, -TG(GSG)$_5$ERP- (SEQ ID NO:82), and EagI sites at the position to be joined. The required six-finger constructs are synthesised by digesting the PCR products with EagI and ligating at that site. All zinc-finger constructs are digested with XbaI and EcoRI restriction enzymes and inserted into the similarly digested, eukaryotic expression vector pcDNA 3.1(−) (Invitrogen). The sequences of all constructs are confirmed by dideoxy sequencing.

Example 18

Binding Affinities of Construct TFIIIA(F1-4)-ZIF

The initial study on a structured-linker containing fusion peptide is conducted on the TF(F1-4)-ZIF construct. This experiment is designed to investigate a couple of issues. First, can TFIIIA finger 4 be used, successfully, outside its natural protein context, to bridge a region of DNA within a non-contiguous binding site? Second, to determine the optimal DNA span of TFIIIA finger 4 within a synthetic fusion peptide.

Figure 18:
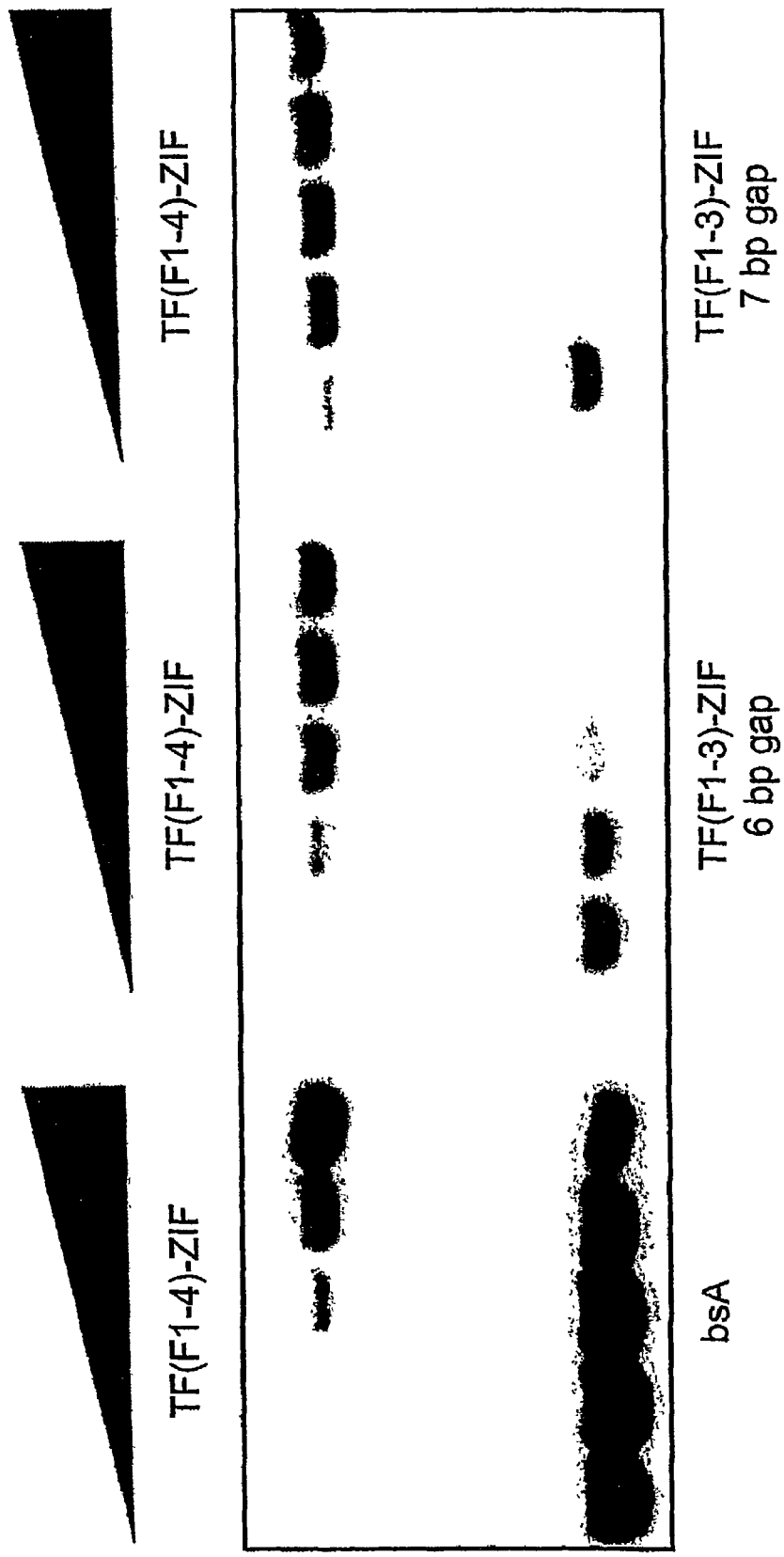
FIG. 18 shows results of gel-shift experiments in which the TFIIIA(F1-4)-ZIF peptide is tested for binding to the ZIF binding site (target bsA), the full length TFIIIA(F1-3)-ZIF site with 6 base pairs of intervening DNA, and the TF(F1-3)-ZIF site with 7 base pairs of intervening DNA. Serial 5-fold dilutions of peptide are indicated by the black triangle (reactions corresponding to left-hand lanes have less peptide than right-hand lanes), and binding site concentration is 0.16 nM.

The TF(F1-4)-ZIF peptide is targeted against non-contiguous binding sites comprising the TFIIIA fingers 1-3 recognition site and the three-finger ZIF site, separated by between 5 and 10 bps of unbound DNA (Table 2). The relative affinity of the peptide for these sites is then compared with its affinity for the ZIF subsite bsA alone. A selection of the gel shift results are shown in FIG. 18, which shows that the TFIIIA(F1-4)-ZIF construct can bind nucleic acid substrates consisting of TFIIIA and ZIF subsites separated by 6 or 7-base pairs. From such gels it is clear that the DNA span of TFIIIA finger 4 in this construct is as much as 10 bp. Non-contiguous binding sites with 6-9 bps of intervening DNA can be bound, although the optimal spacing is found to be 7 or 8 bp. These optimal sites are bound at least 125-fold tighter than the ZIF site alone.

The results of this experiment accord with the fact that the fourth finger of TFIIIA is known not to bind DNA in a sequence-specific manner, and that this finger jumps, spans or bridges the minor groove of DNA in the crystal structure of the first 6 fingers of TFIIIA (Nolte et al., 1998, *Proc. Natl. Acad. Sci. USA* 95, 2938-2943.).

Example 19

Binding Affinities of Construct GAC-F4-ZIF

Figure 19:
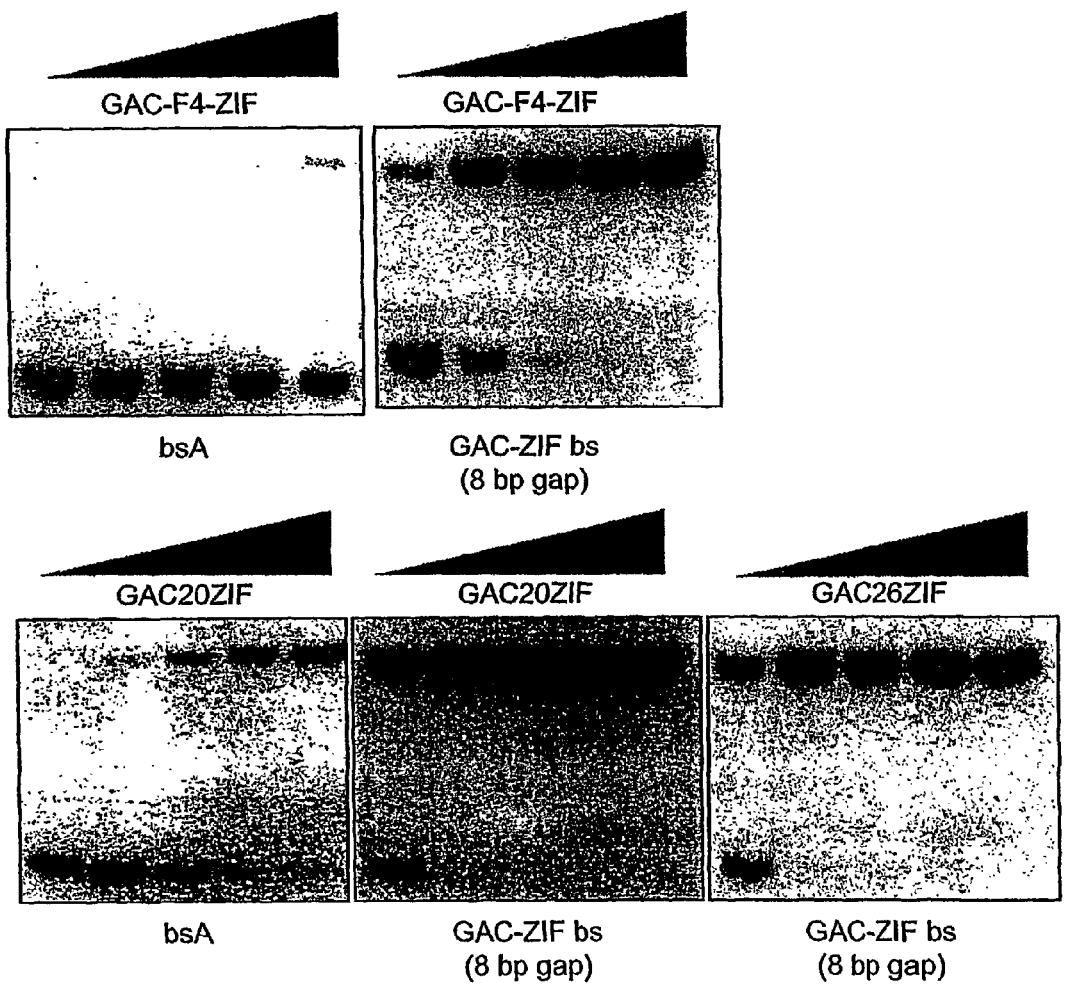
FIG. 19 shows results of gel-shift experiments in which the GAC-F4-ZIF peptide is tested for binding to the ZIF binding site (target bsA), and the full-length GAC-ZIF site with 8 base pairs of intervening DNA (top panels). The bottom panels show results of gel-shift experiments in which GAC20ZIF (bottom left-hand and middle panels) is tested for binding to the ZIF binding site (target bsA) and the full-length GAC20ZIF binding site with 8 base pairs of intervening DNA; and GAC26ZIF (bottom right-hand panel) is tested for binding to the full-length GAC-ZIF binding site with 8 base pairs of intervening DNA. Serial 5-fold dilutions of peptide are indicated by the black triangle (reactions corresponding to left-hand lanes have less peptide than right-hand lanes), and binding site concentration is 0.10 nM.
Figure 20:
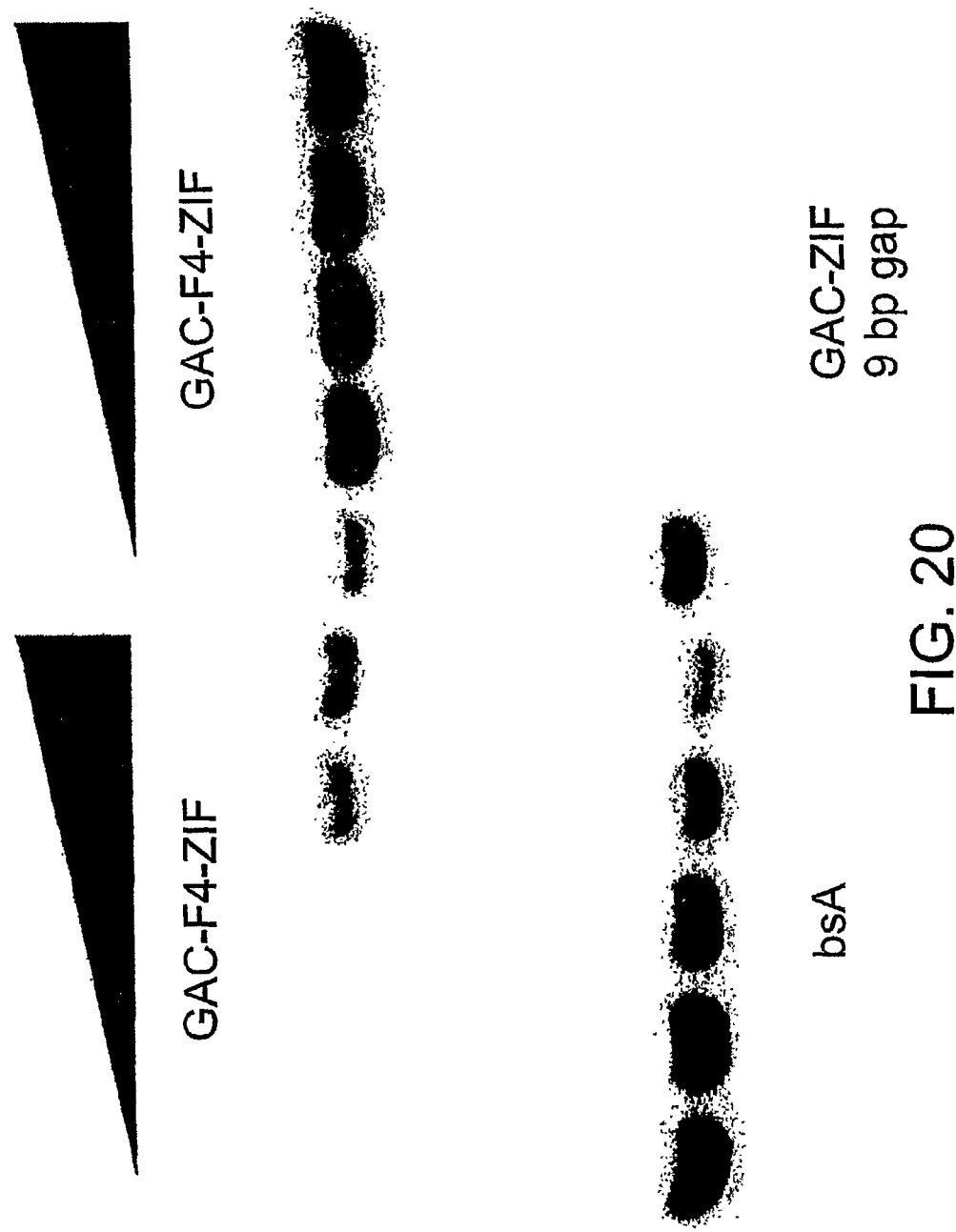
FIG. 20 shows results of gel-shift experiments in which the GAC-F4-ZIF peptide is tested for binding to the ZIF binding site (target bsA), and the GAC-ZIF site with 9 base pairs of intervening DNA. Serial 5-fold dilutions of peptide are indicated by the black triangle (reactions corresponding to left-hand lanes have less peptide than right-hand lanes), and binding site concentration is 0.16 nM.

To determine whether TFIIIA F4 would still function as a linker when taken out of the context of neighbouring TFIIIA fingers, the GAC-F4-ZIF construct is made (FIGS. 14 and 16). This construct can be thought of simply as two ZIF-based DNA binding domains joined by a structured linker (in this case TFIIIA F4). As above, this construct is tested for affinity against a range of sequences, comprising the appropriate binding subsites separated by 6 to 11 bps of DNA (Table 3). In these studies TFIIIA finger 4 is again demonstrated to be an effective linker. Results of gel-shift experiments are shown in FIGS. 19 and 20. As before the new peptide is shown to bind its optimal, full-length target sites at least 125-fold stronger than the 9 bp ZIF site. In this case, however, the optimal DNA span is found to be 8 or 9 bps, although 7-11 bp stretches could be spanned without a significant loss in binding affinity.

Example 20

Binding Affinities of Construct ZIF-ZnF-GAC

We next tested the possibility that a natural zinc finger, of the type found in the ZIF peptide, may function as a stable unit that spans 3 bps (or occasionally 4 bps) of DNA while occupying the major groove. If so, a 'neutral' zinc finger module, i.e. one that does not recognise a specific DNA sequence, might be used as a structured linker to span 3 or 4 bps.

For this purpose a 'neutral' finger is created by replacing the DNA binding residues (those at positions—1, 2, 3, and 6) of wild type ZIF268 finger 2, with serine residues. Serine can act as either an H-bond acceptor or donator, and can therefore interact with all four bases in DNA. This new finger, denoted "ZnF" and flanked by two GERP linkers, is used to join the three-finger peptides of ZIF and the GAC-clone, creating the seven-finger array ZIF-ZnF-GAC (FIG. 17). This peptide is targeted against non-contiguous sites comprising the 9 bp ZIF and GAC-clone recognition sequences separated by 2, 3, 4 or 5 bps of DNA, and also sites bsA and bsC for comparison (FIG. 21). The results demonstrate that the peptide binds all full-length target sites comprising the ZIF and GAC subsites either adjacent or separated by up to 5 base pairs of unbound DNA at least 500-fold tighter than it does the ZIF site alone. These results suggest that the peptide may bind the contiguous ZIF-GAC site fractionally weaker than it does the non-contiguous sites, but the difference (if any) is slight. Hence, it appears that the "neutral" zinc finger linker is able to function as an effective linker, either in or out of the DNA major groove.

Example 20A

Binding Affinity of TFIIIA/ZIF Fusion Peptides

The TF(1-4)-ZIF and TF(1-3)-flex-ZIF peptides are tested against the non-contiguous TF-5,6,7,8,9-Z sites. In these first experiments the DNA composition of the non-bound region is based on the endogenous TFIIIA target site. The results clearly show that the TF(1-4)-ZIF peptide has a preference for non-contiguous sites separated by 7 or 8 bp gaps, which are bound with a Kd of approx. 3 pM (Table 6). The target sites with 5, 6 or 9 bp gaps are bound at least 5-fold weaker (FIG. 27A). In contrast, the TF(1-3)-flex-ZIF peptide shows no preference for a particular DNA span, binding all non-contiguous sites with affinities of around 60 pM (FIG. 27B). Further studies are conducted on binding sites with various sequences in the non-bound region of the DNA target site. These demonstrate that the peptides have no preference for particular sequence compositions within this non-bound region (data not shown). Both constructs bind the Zif268 half-site with similar affinity, as expected.

Example 20B

Binding Affinity of ZIF/GAC Fusion Peptides

The first binding study is conducted on ZIF-F4-GAC to determine the optimal span of TFIIIA finger 4 in this construct. This peptide is titrated against the continuous 18 bp ZM binding site, and non-continuous binding sites with 1-10 bps of non-bound DNA. Our results demonstrate that this peptide has little preference for a particular span of DNA, although the highest affinity binding is observed for sites containing 3 bp or >7 bp insertions (Table 7). The fact that this peptide is able to bind with such high affinity to sites with less that 3 bp gaps is highly unexpected. The slight reduction in binding affinity observed in these examples is presumably because the 1-2 bp gaps are too small to accommodate a zinc finger in the DNA major groove. In these circumstances it seems likely that the non-binding finger actually flips out of the DNA leaving the remaining fingers to bind the target site. The slight reduction in affinity for sites with 5 or 6 bp gaps is probably because TFIIIA finger 4 has to stretch half a helical turn around the DNA. For longer gaps the finger is likely to span tie minor groove as is seen in wild-type TFIIIA.

A further set of binding studies is then carried out on the construct containing the non-specific zinc finger linker, ZIF-ZnF-GAC. Although this construct is expected to target (primarily) non-contiguous sequences containing three or four base pairs of non-bound DNA, it is tested against all of the binding sites from ZM to Z10M. Our gel-shift data again demonstrates that this peptide is able to bind its optimal targets with very high affinity (3-4 pM), and shows a similar trend in binding affinity to the ZIF-F4-GAC peptide (FIG. 27C). However, this peptide is able to bind its least favourable sites with slightly greater affinity than observed for the previous peptide (Table 7).

It was thought that the -NIKICV-(SEQ ID NO:80) and -TQQLP-(SEQ ID NO:81) linkers found either side of wild-type TFIIIA finger 4 would be more structured than the flexible -TGERP-(SEQ ID NO:84) linkers which flanked the serine-mutated finger of ZIF-ZnF-GAC. Therefore, the ZIF-mutF4-GAC and ZIF-mutZnF-GAC peptides are synthesised and tested to determine whether these linker sequences are responsible for the less selective binding of the ZIF-ZnF-GAC peptide. These new peptides are targeted against all eleven binding sequences, as above. The ZIF-mutZnF-GAC peptide is found to bind the Z5M and Z6M binding sites with Kd's of 18 pM and 11 pM respectively. All other binding sites are bound with very similar affinities to the ZIF-ZnF-GAC peptide (data not shown). By comparison, the ZIF-mutF4-GAC peptide binds both the Z5M and Z6M sites with apparent Kd's of 13 pM. From these data is appears that the -NI- KICV-(SEQ ID NO:80) and -TQQLP-(SEQ ID NO:81) linkers slightly weaken the binding of the peptides to DNA sequences with 5 or 6 by gaps. This may be because they are less flexible than the -TGERP- (SEQ ID NO:84) linkers, and are less able to bend around the DNA helix. No differences in DNA-binding characteristics for the different linker combinations are observed when the binding subsites are located on approximately the same face of the DNA.

Finally, the ZIF-flex-GAC peptide is examined in the same way as the structured-linker peptides above. This peptide, as with the TF(1-3)-flex-ZIF peptide, displays no preference for a particular length of DNA span, and bound all sites with affinities of approximately 50 pM. This 3-10 fold reduction in afinity—compared to peptides connected by structured linkers—is probably due to the increased conformational freedom of this peptide, which makes DNA binding less entropically favourable.

TABLE 6

The binding site sequences used in gel-shift experiments with the TFIIIA-ZIF fusion peptides and the binding affinities obtained.

| Binding Site Name | Binding Site Sequence* | Apparent Kd (pM) | |
|---|---|---|---|
| | | TF(1-4)-ZIF | TF-flex-ZIF |
| ZIF | GCGTGGGCG | 2000 | 1800 |
| TF5Z | GCGTGGGCGX$_5$GGATGGGAGAC | 21 | 63 |
| TF6Z | GCGTGGGCGX$_6$GGATGGGAGAC | 17 | 68 |
| TF7Z | GCGTGGGCGX$_7$GGATGGGAGAC | 3 | 57 |
| TF8Z | GCGTGGGCGX$_8$GGATGGGAGAC | 3 | 61 |
| TF9Z | GCGTGGGCGX$_9$GGATGGGAGAC | 15 | 58 |

*Non-bound DNA bases in the target sequence are shown by a bold 'X'. The exact base composition of these gaps is found to have no significant effect on peptide affinity.

TABLE 7

The binding site sequences used in gel-shift experiments with the ZIF-GAC fusion peptides and the binding affinities obtained.

| Binding Site Name | Binding Site Sequence* | Apparent Kd (pM) | |
|---|---|---|---|
| | | ZIF-F4-GAC | ZIF-ZnF-GAC |
| ZIF | GCGTGGGCG | 2200 | 2000 |
| ZM | GCGGACGCGGCGTGGGCG | 11 | 7 |
| Z1M | GCGGACGCGXGCGTGGGCG | 6 | 4 |
| Z2M | GCGGACGCGX$_2$GCGTGGGCG | 7 | 6 |
| Z3M | GCGGACGCGX$_3$GCGTGGGCG | 5 | 4 |
| Z4M | GCGGACGCGX$_4$GCGTGGGCG | 13 | 3 |
| Z5M | GCGGACGCGX$_5$GCGTGGGCG | 16 | 8 |
| Z6M | GCGGACGCGX$_6$GCGTGGGCG | 17 | 7 |
| Z7M | GCGGACGCGX$_7$GCGTGGGCG | 5 | 3 |
| Z8M | GCGGACGCGX$_8$GCGTGGGCG | 5 | 6 |
| Z9M | GCGGACGCGX$_9$GCGTGGGCG | 5 | 4 |
| Z10M | GCGGACGCGX$_{10}$GCGTGGGCG | 4 | 3 |

*Non-bound DNA bases in the target sequence are shown by a bold 'X'. The exact base composition of these gaps is found to have no significant effect on peptide affinity.

Example 21

Binding Affinities of ZIF-GAC and 3x2F ZGS Peptides to Targets with Deleted Subsequence This example shows the differential effects of looping out of a single finger from a zinc finger protein/DNA complex.

To investigate the effect of finger-flipping or looping in 2x3F and 3x2F zinc-finger peptides, gel-shift experiments are conducted with the 2x3F ZIF-GAC peptide and the 3x2F ZGS peptide, against a selection of modified binding sites; bs1, bs2, bs3, bs4 (FIGS. 22 and 23), as well as bsA and bsC, as control sites. FIG. 22 shows results of gel-shift experiments in which the 2x3F ZIF-GAC peptide is tested for binding to the 9 base pair ZIF binding site (target bsA), the 18 base pair ZIF-GAC binding site (bsC) as well as bs1, bs2, bs3 and bs4, which comprise the ZIF-GAC bsC sequence, but with the three base subsequence recognised by finger 4 of 2x3F ZIF-GAC removed, and 0, 1, 2 or 3 base pairs respectively inserted in its place, while FIG. 23 shows corresponding experiments using 3x2F ZGS peptide.

By comparing the relative affinities of each peptide for the sites bs1-4 against the designed, full-length binding site, bsC; the ability of zinc-finger peptides to accommodate finger "flipping" can be demonstrated. The sequence of bs1 is similar to that of bsC, but with the three bases recognised by finger 4 of the 3x2F ZGS or 2x3F ZIF-GAC peptides completely removed. The sites bs2, bs3 and bs4 are identical to bs1, except for the insertion of 1, 2 or 3 base pairs (respectively), in the region normally bound by zinc-finger 4 of the fusion peptides. The inserted residues are selected so that they would not be the same as the sequence recognised by finger 4. It should be noted that the binding site of bs4 is the same length as bsC, but zinc-finger 4 will not contribute binding energy to the complex with this site. The other sites, bs1, bs2 and bs3 are shorter by 3, 2 and 1 bps respectively.

The gel-shift results with the 2x3F ZIF-GAC and 3x2F ZGS peptides are shown in FIGS. 22 and 23 respectively. Serial 5-fold dilutions of peptide are made and incubated with 0.01 nM binding site. Significantly, the results demonstrate that the 3x2F ZGS peptide is far more selective for the correct, full length binding site (bsC) than is the 2x3F ZIF-GAC peptide. The gel-shift results of FIG. 23 show that the 3x2F ZGS peptide binds the incorrect, full length binding site (bs4) approximately 125-fold weaker than it does bsC; its binding is therefore relatively specific. It also binds the site bs3 and bs2 with almost identical affinity to bs4. (These sites are truncated in the region normally bound by finger 4). The shortest site, bs1, is bound at least 625-fold less tightly than the correct binding sequence, bsC. The 3x2F ZGS peptide clearly binds bs1 slightly more tightly than it does the ZIF site alone, but the concentrations of protein and binding site used in these experiments are such that binding to the ZIF site alone is barely detectable. In contrast, the 2x3F ZIF-GAC peptide binds the sequence of bs4 only 5-fold more weakly than it does bsC, and as above, its affinity for the sites bs3 and bs2 are very similar to that of bs4, demonstrating that it is relatively non-specific. The peptide shows reasonable discrimination when targeted to the bs1 site, which it binds approximately 125-fold weaker than bsC. These data clearly demonstrate than the individual zinc-fingers within a zinc-finger array (such as the 2x3F ZIF-GAC and the 3x2F ZGS peptides) are able to "flip" out of the DNA major groove—when they do not recognise the DNA sequence presented to them—in order to allow the remaining zinc-fingers to bind in the most optimal conformation. The ability of the zinc-finger peptide to accommodate this conformational change is dependant on the construction of the peptide. These results show that the detrimental effects of finger "flipping" are far more pronounced in the 3x2F ZGS peptide than in the 2x3F ZIF-GAC peptide, demonstrating that 3x2F peptides are far more specific than 2x3F peptides.

Example 22

Use of Two Finger Library for Selection of Zinc Fingers

The simplest approach is to construct an isolated two finger library, comprising amino acids known to contribute to DNA-binding affinity and specificity. Such a library is constructed using suitable randomizations. A phage display library is constructed using methods known in the art, and a number of 6-7 bp DNA targets are used in selections that are carried out essentially as detailed in patent applications WO 96/06166 and WO 98/53057. After the selection process is complete, a number of tightly binding zinc finger proteins are isolated.

Example 23

Use of Combinatorial Library for Selection of Zinc Fingers

We further demonstrate the construction of libraries for 2-finger domains whose register of interaction is precisely fixed. This is achieved by employing "GCG" anchors and two extensively-randomised zinc fingers. The libraries are designed to take into account synergistic effects between zinc fingers, by modifying cross-strand contacts from position 2. Consequently, position 2 of F2 is modified to Ser or Ala so as to interact universally with either the $^7C$ in the "GCG" anchor, or any base ($^7N$) in the final target site sequence. Similarly, position 2 of F3 is modified to Ser or Ala so as not to interfere with the selection of bases $^4'X$ or $^4'X$. Phage display libraries are constructed using methods known in the art and a number of DNA targets are used in selections that are carried out essentially as detailed in patent applications WO 96/06166 and WO 98/53057. After the selection process is complete, a number of tightly binding zinc finger proteins are isolated. After selecting against particular DNA target sites, the genes for the appropriate 2-finger domains are easily recovered by PCR.

Example 24

Use of Combinatorial Library for Selection of Zinc Fingers

Phage Display libraries Lib1/2 and Lib 2/3 are used to select 2-Finger construction units. More specifically, the libraries are used to select two finger units that bind DNA sites of the form 5'-GXX XXX-3' or 5'-XXX XXG-3' (where X is any base). Despite the fact that one base must be fixed as "G" in each target site, this still allows 2048 of all the 4096 (=$4^6$) possible 6-base 2-finger recognition sites to be targeted. Phage display libraries are constructed using methods known in the art, and a number of DNA targets are used in selections that are carried out essentially as detailed in patent applications WO 96/06166 and WO 98/53057. After the selection process is complete, a number of tightly binding zinc finger proteins are isolated.

The genes for the appropriate 2-finger domains are easily recovered by PCR. Because of the design of the libraries, the "GCGG" or "GGCG" anchors serve to fix the register of DNA-protein interaction very precisely. Hence, the required 2-finger domains may be specifically amplified from the respective libraries constructs by selective PCR using primers which bind only to the DNA sequence of finger 1 or finger 2 or finger 3. The first finger of the eventual 3x2F construct is preceded by an Xba I site and a MET codon. The second finger is joined to the third finger using an engineered Eag I site. The fourth finger is joined to the fifth finger through a BamHI site (at the end of finger 4) and a Bgl II site (at the start of finger 5). The sixth finger is followed by an EcoRI site.

The sequences are designed such that: If finger 2 joins to itself via the Eag I site, a Not I site is generated so this incorrect product can be recycled by digestion. When finger 4 joins correctly to finger 5 both BamHI and Bgl II sites are destroyed, however incorrectly fused units can be redigested with the appropriate enzyme. Hence, only the full-length 3x2F construct will be amplified with terminal primers following ligation of the three 2-finger units.

Using these construction techniques, the three 2-finger units selected as described above are fused to form a 3x2 protein.

Example 24

Library Selection of 2-Finger Units for Construction of 3x2F Peptides

As described above, 3x2F peptides may be made by linking 2 finger modules with suitable linkers. The above examples describe the isolation of such 2 finger modules by ligation of synthetic oligonucleotides. However, and as described here, 2 finger modules may be selected by phage display using libraries (LIB12 and LIB23 libraries) comprising approximately one and a half fingers (see above and WO 98/53057).

Thus, the required 2-finger domains may be specifically amplified from the library constructs by selective PCR— using primers which bind only to the DNA sequence of finger 1 or finger 2 or finger 3. The sequences of these primers are as shown in the Examples above.

The first finger of the eventual 3x2F construct is preceded by an Xba I site and a MET codon. The second finger is joined to the third finger using an engineered Eag I site. The fourth finger is joined to the fifth finger through a BamHI site (at the end of finger 4) and a Bgl II site (at the start of finger 5). The sixth finger is followed by an EcoRI site.

The sequences are designed such that: If finger 2 joins to itself via the Eag I site, a Not I site is generated so this incorrect product can be recycled by digestion. When finger 4 joins correctly to finger 5 both BamHI and Bgl II sites are destroyed, however incorrectly fused units can be redigested with the appropriate enzyme. Hence, only the full-length 3x2F construct will be amplified with terminal primers following ligation of the three 2-finger units.

Example 25

Primer Sequences

Primers are named by the following method: A, B, C (in position 1) shows which of the three 2-finger units is to be amplified, A is the first two fingers of the 3x2F construct, B implies fingers 3 and 4 and C fingers 5 and 6. N, C (in position 2) shows whether the oligo primes from the N- or C-terminus. F1, F2, F3 shows which finger of the 3-finger library the primer binds to. L12, L23, L123 shows whether the primer binds specifically to LIB12, Lib23 or binds to both libraries.

The final two primers are specific for the extreme N- and C-termini of the 3x2F constructs and are used to amplify the full length ligation product from any intermediate species.

```
ANF1L12
        Xba I
CAG TTG CGT CTA GAC GCC GCC ATG GCG GAG AGG CCC TAC GCA
TGC

ANF2L123
        Xba I
CAG TTG CGT CTA GAC GCC GCC ATG GCT GAG AGG CCC TTC CAG
TGT CGA ATC TGC AT

ANF1L23
        Xba I
CAG TTG CGT CTA GAC GCC GCC ATG GCA GAA CGC CCA TAT GCT
TGC

ACF3L12
          Eag I
GC GGC CGC CGG CCG CTG GCC TCC TGT ATG GAT TTT GGT A

ACF2L123
          Eag I
CAT GGC ATT CGG CCG CTC GCC TCC TGT GTG GGT GCG GAT G

ACF3L23
          Eag I
GC GGC CGC CGG CCG TTG TCC GCC CGT GTG TAT CTT GGT A

BNF1L12
         Eag I
TCA AGC TGC CGG CCG TAC GCA TGC CCT GTC GAG TC

BNF2L123
         Eag I
AGC TCT CAG CGG CCG TTC CAG TGT CGA ATC TGC AT

BNF1L23
         Eag I
TCA AGC TGA CGG CCG TAT GCT TGC CCT GTC GAG TC

BCF3L12
           BamH I
CGC GTC CTT CTG GGA TCC TGT ATG GAT TTT GGT A

BCF2L123
           BamH I
ACC CTT CTC GGA TCC TGT GTG GGT GCG GAT G

BCF3L23
            BamH I
C CGC ATC TTT TTG GGA TCC CGT GTG TAT CTT GGT A

CNF1L12
          Bgl II
TCA AGC TGC AGA TCT GAG AGG CCC TAC GCA TGC CCT GTC
```

```
                    -continued
CNF2L123
         Bgl II
ACG TCT ACG AGA TCT CAG AAG CCC TTC CAG TGT CGA ATC TGC AT CNF1L23
         Bgl II
TCA AGC TGA AGA TCT GAA CGC CCA TAT GCT TGC CCT GTC CCF3L12
         EcoR I
CAT TTA GGA ATT CCG GGC CGC GTC CTT CTG TCT CAG ATG GAT
TTT CCF2L123
         EcoR I
CAT TTA GGA ATT CCG GGC CGC ATC CTT CTG GCG CAG GTG GGT
GCG GAT G CCF3L23
         EcoR I
CAT TTA GGA ATT CCG GGC CGC ATC TTT TTG GCG CAG GTG TAT C NXbaAMP
         Xba I
CAG TTG CGT CTA GAC GCC GCC CEcoAMP
         EcoR I
CAT TTA GGA ATT CCG GGC CGC
```

Example 26

Selection of Sites and Construction of 3x2F Znf to Bind the GC Box/NRF-1 Site in Promoter Region of the CXCR4 Gene Promoter Sequence (top) (SEQ ID NO:120) with potential 6 by sites marked below.

```
5' T C C C C G C C C C A G C G G C G C A T G C G C C G C G C 3'

A   T C C C C G C C C C A G     G G C G C A     G C G C C G

B         G C C C C A G C G G C G C A T G C G

C                 C A G C G G C G C A T G
```

N.B. 6 bp sites are chosen which are either adjacent or within 1 bp of each other as 2-finger units bind optimally when within 1 bp of each other.

Protocol i) Select Sites on Row B.

Perform selections in usual manner. GCCCCA: target with LIB 12 and take fingers 1 and 2—F5+F6 of the 3x2 construct. GCGGCG: may be targeted by LIB12 and take fingers 1 and 2, or fingers 2 and 3; or may be targeted by LIB23 and take fingers 2 and 3 or fingers 1 and 2. Generates F3+F4 of the 3x2 construct. CATGCG: can be targeted by LIB23 and take fingers 2 and 3. Gives F1+F2 of the 3x2 construct.

ii) Join 2-Finger Units to Create 3x2F Peptide.

PCR amplify fingers binding appropriate sequences. Purify 2-finger products. Combine products, digest with EagI, BamHI and Bgl II. Heat inactivate EagI. Ligate fragments together in the presence of Not I, BamHI and BglII to destroy incorrectly ligated fragments. PCR amplify 6-finger construct with N- and C-terminal specific primers. Digest with XbaI and EcoRI, ligate into similarly digested vector—pTracer.

Example 27

Comparison of a 2x3F Peptide and a Similar 3x2F Peptide

A. Creation of a 2x3F Peptide 3-finger units are selected to bind the 9-bp target sequences, 11 and 9 (below), essentially as described above and also in WO 98/53057.

```
        11:   GCA GGG GTT

9:   GGC CAG GCG 11-9:   GGC CAG GCG GCA GGG GTT
```

The 3 finger peptide which binds site 11 is referred to as pep11, and the 3 finger peptide which binds site 9 is referred to as pep9. To create a 2x3F peptide pep11 is joined to the N-terminus of pep9, using the procedure below, and the new 6-finger construct is called 2x3F pep11-9. This new peptide targets the contiguous sequence 11-9, shown above.

All primer sequences in this Example are the same as the corresponding sequences in Example 25 having the same name. Primer CWT2 is identical to Primer a (SEQ ID NO: 2); Primer NWT3S is identical to Primer B (SEQ ID NO: 3); Primer CGAC1 is identical to Primer c (SEQ ID NO: 6); Primer NGAC2F is identical to Primer D (SEQ ID NO: 7). Primer 3x2CF3L23 has the following sequence: GC GGC CGC CGG CCG CTG GCC CGT GTG TAT CTT GGT A (SEQ ID NO:123).

Figure 27:
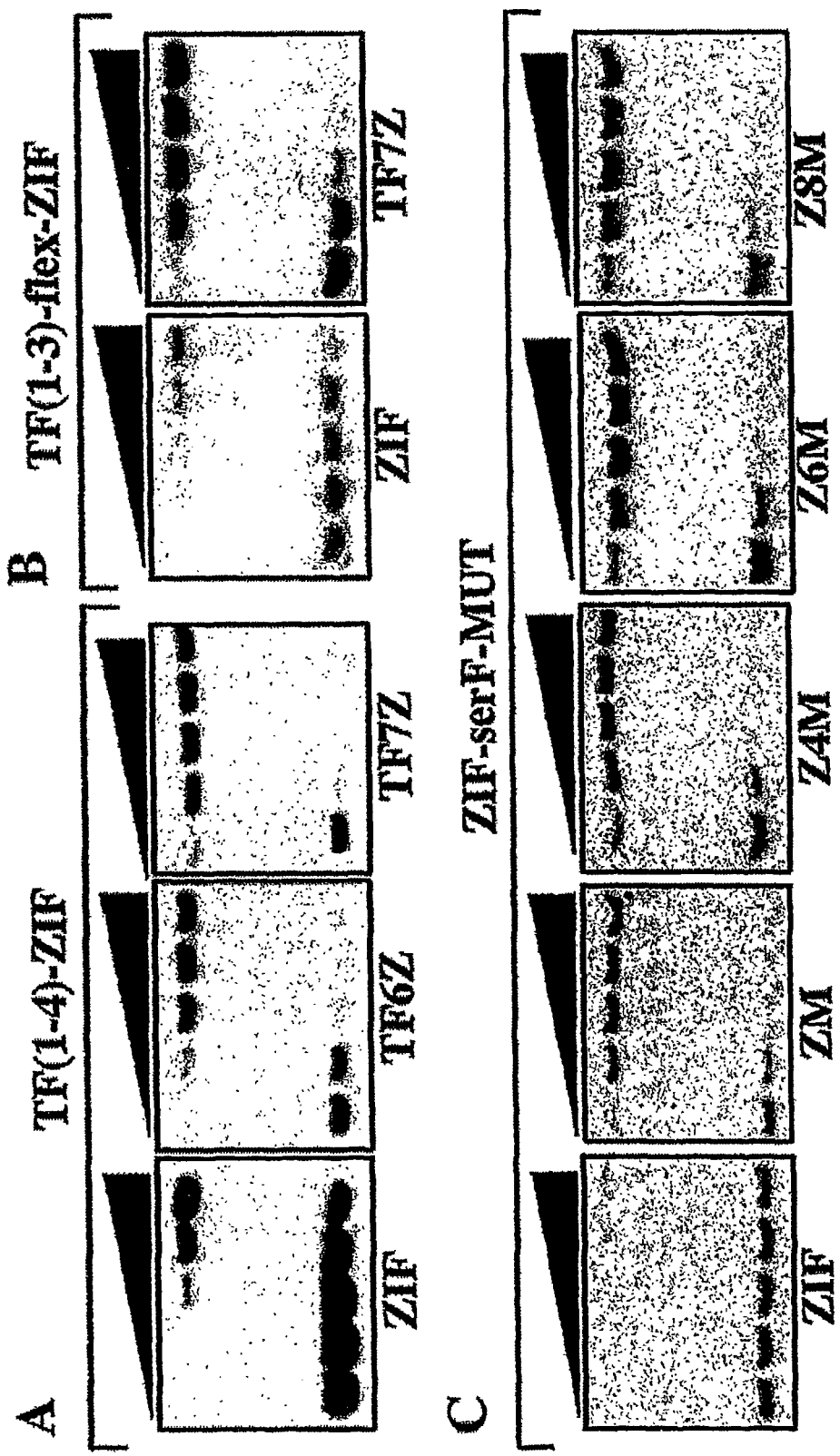
FIG. 27. A selection of DNA binding studies by gel-shift assay. (A) 5-fold dilutions of TF(1-4)-ZIF (from 5.5 nM-9 pM), against 20 pM ZIF binding site; 2 pM TF6Z and 2 pM TF7Z. (B) 5-fold dilutions of TF(1-3)-flex-ZIF (from 5 nM-8 pM), against 20 pM ZIF and 2 pM TF7Z. (C) 5-fold dilutions of ZIF-serF-MUT (from 1 nM-1.6 pM), against 10 pM ZIF; 0.4 pM ZM; 0.4 pM Z4M; 0.4 pM Z6M and 0.4 pM Z8M.

The sequence of 2x3F pep11-9 is shown in FIG. 27, and the sequence of 3x2Fpep11-9 is shown in FIG. 28.

Construction Procedure

Primer pairs: ANF1L12 and BCF3L23; and CNF1L23 and CCF2L23, are used to amplify the DNA encoding pep11 and pep9, respectively. This created a BamHI site at the 3' end of the pep11 gene and a BglII site at the 5' end of the pep9 gene. Hence, digestion of the PCT fragments with these enzymes, followed by ligation created the 6-finger construct 2x3 pep11-9, in which both original enzyme sites are destroyed and the peptide linker sequence -TGSERP-(SEQ ID NO:141) is created. The full-length fragment is then digested with XbaI and EcoRI and ligated into similarly digested pTracer (Invitrogen).

B. Creation of the 3x2F Peptide

To give a direct comparison between a selected 2x3F peptide and a 3x2F peptide targeted against the same DNA sequences, the zinc fingers of pep11 and pep9 are fused together in the style of a 3x2F peptide, using the procedure outlined below. This peptide, called 3x2F pep11-9, targets the contiguous DNA sequence 11-9, above. Again, primer and peptide sequences are as shown above and in the Figures.

Construction Procedure

Fingers 1 and 2 of pep11 are amplified by PCR using primers ANF1L12 and CWT2. Separately, finger 3 of pep11 is amplified using primers NWT3S and 3x2CF3L23. The 3-finger fragment pep11(3x2) is then created by overlap PCR using the above fragments. Similarly, finger 1 of pep9 is amplified using primers BNF1L23 and CGAC1, and fingers 2 and 3 of pep9 are amplified using primers NGAC2S and CCF3L23. The 3-finger fragment pep9(3x2) is then created by overlap PCR. The primers 3x2CF3L23 and BNF1L23 produce Eag I restriction sites at the 3' and 5' ends of Pep11 (3x2) and pep9(3x2) respectively. Hence, digestion of the two 3-finger fragments with EagI, followed by ligation created the 6-finger construct 3x2F pep11-9. In this peptide the linker sequences -TGGEKP-(SEQ ID NO:124) and -TGGQKP-(SEQ ID NO:125) are inserted between fingers 2 and 3 and fingers 4 and 5 respectively, and the sequence -TGQRP-(SEQ ID NO:126) separates fingers 3 and 4. The full-length fragment is then digested with XbaI and EcoRI and ligated into similarly digested pTracer (Invitrogen), as above.

C. Methods

The 2x3F pep11-9 and 3x2F pep11-9 peptides are compared by assessing their binding affinities for the 11-9 binding site and for binding site sequences mutated in the region bound by finger 1 (11-9mut1), finger 3 (11-9mut3), or with the bases bound by finger 3 deleted (11-9del3). These sequences are shown below, with mutated regions underlined.

```
11-9:       GGC CAG GCG GCA GGG GTT 11-9mut1:   GGC CAG GCG GCA GGG ACC 11-9mut3:   GGC CAG GCG ATG GGG GTT 11-9del3:   GGC CAG GCG GGG GTT
```

In vitro fluorescence ELISA is used to estimate the binding specificity of each peptide for the various target sites, as described below.

Protocol for In Vitro Fluorescence ELISA

Preparation of Template

Zinc finger constructs are inserted into the protein expression vector pTracer (Invitrogen), downstream of the T7 RNA transcription promoter. Suitable templates for in vitro ELISA are created by PCR using the 5' primer (GCA-GAGCTCTCTGGCTAACTAGAG) (SEQ ID NO:130), which binds upstream of the T7 promoter and a 3' primer, which binds to the 3' end of the zinc finger construct and adds a sequence encoding for the HA-antibody epitope tag (YPY-DVPDYA) (SEQ ID NO:28).

Zinc Finger Expression

In vitro transcription and translation are performed using the T7 TNT Quick Coupled Transcription/Translation System for PCR templates (Promega), according to the manufacturers instructions, except that the medium is supplemented with 500 µM $ZnCl_2$.

Fluorescence ELISA

DNA binding reactions contained the appropriate zinc finger peptide, biotinylated binding site (10 nM) and 5 µg competitor DNA (sonicated salmon sperm DNA), in a total volume of 50 µl, which contained: 1×PBS (pH 7.0), $1.25 \times 10^{-3}$ U high affinity anti-HA-Peroxidase antibody (Boehringer Mannheim), 50 µM $ZnCl_2$, 0.01 mg/ml BSA, and 0.5% Tween 20. Incubations are performed at room temperature for 40 minutes. Black streptavidin-coated wells are blocked with 4% marvel for 1 hour. Binding reactions are added to the streptavidin-coated wells and incubated for a further 40 minutes at room temperature. Wells are washed 5 times in 100 µl wash buffer (1×PBS (pH 7.0), 50 µM $ZnCl_2$, 0.01 mg/ml BSA, and 0.5% Tween 20), and finally 50 µl QuantaBlu peroxidase substrate solution (Pierce) is added to detect bound HA-tagged zinc finger peptide. ELISA signals are read in a SPECTRAmax GeminiXS spectrophotometer (Molecular Devices) and analysed using SOFTmax Pro 3.1.2 (Molecular Devices).

D. Results

In Vitro Fluorescence ELISA Assay

Figure 26:
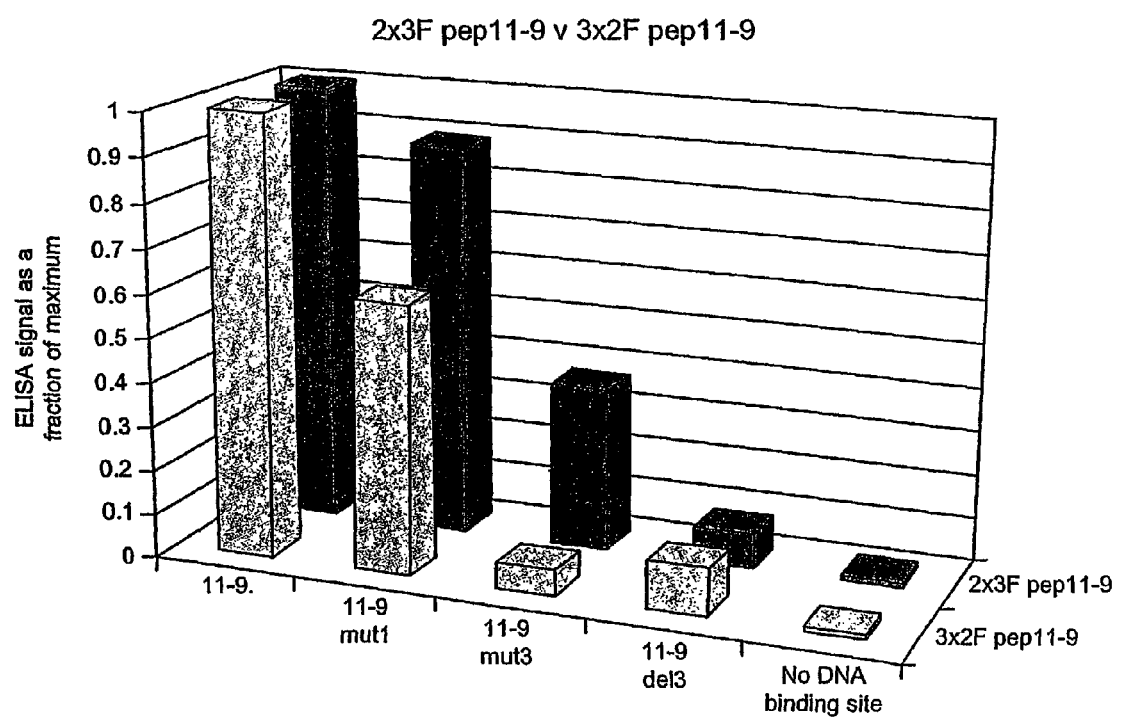
FIG. 26 is a plot depicting the binding of a 2X3 peptide (2X3F pep11-9) and a 3X2 peptide (3X2F pep11-9), expressed as ELISA signal as a fraction of maximum, to the following binding sites: 11-9; 11-9mut1; 11-9mut3; 11-9del3. No binding site is shown as a control.

To compare the specificity of the 2x3F pep11-9 and 3x2F pep11-9 peptides, samples from the same translation reaction are assayed against each of the binding sites above. The ELISA signals obtained from each assay are then normalised relative to the maximum signal obtained for that peptide. (In this way the absolute amount of either peptide produced by the in vitro transcription/translation system is insignificant). These data are then plotted on a graph, shown as FIG. 26.

As can be seen, the data demonstrates that the 3x2F peptide shows greater selectivity/specificity for its correct target sequence, over mutant sequences, than does the 2x3F peptide.

Each of the applications and patents mentioned above, and each document cited or referenced in each of the foregoing applications and patents, including during the prosecution of each of the foregoing applications and patents ("application cited documents") and any manufacturer's instructions or catalogues for any products cited or mentioned in each of the foregoing applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Each of the applications and patents mentioned above, and each document cited or referenced in each of the foregoing applications and patents, including during the prosecution of each of the foregoing applications and patents ("application cited documents") and any manufacturer's instructions or catalogues for any products cited or mentioned in each of the foregoing applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference. In particular, we hereby incorporate by reference International Patent Application Numbers PCT/GB00/02080, PCT/GB00/02071, PCT/GB00/03765, United Kingdom Patent Application Numbers GB0001582.6, GB0001578.4, and GB9912635.1 as well as U.S. Ser. No. 09/478,513.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

```
                              SEQUENCE LISTING

<160> NUMBER OF SEQ ID NOS: 144

<210> SEQ ID NO 1
<211> LENGTH: 53
<212> TYPE: DNA
<213> ORGANISM: Artificial Sequence
<220> FEATURE:
<223> OTHER INFORMATION: Description of Artificial Sequence: Primer A

<400> SEQUENCE: 1
cagccggccc atatgcgtct agacgccgcc atggcagaac gcccgtatgc ttg          53

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer a

<400> SEQUENCE: 2
ctgtgtgggt gcggatgtgg gt                                             22

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Primer B

<400> SEQUENCE: 3
acccacatcc gcacccacac aggtggcgag aagccttttg cc                       42

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Primer b

<400> SEQUENCE: 4
gcaagcatac ggccgttcac cggtatggat tttggtatgc ctcttgcgt                49

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Primer C
```

-continued

```
<400> SEQUENCE: 5
atggcagaac ggccgtatgc ttgccc                                          26

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer c

<400> SEQUENCE: 6
gtgtggatgc ggatatggcg ggt                                             23

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Primer D

<400> SEQUENCE: 7
cccgccatat ccgcatccac acaggtggcc agaagcccdtt ccag                      44

<210> SEQ ID NO 8
<211> LENGTH: 62
<212> TYPE: DNA
<213> ORGANISM: Artificial Sequence
<220> FEATURE:
<223> OTHER INFORMATION: Description of Artificial Sequence: Primer d

<400> SEQUENCE: 8
tcattcaagt gcggccgctt aggaattccg ggccgcgtcc ttctgtctta aatggatttt     60
gg                                                                    62

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: modified
      primer b

<400> SEQUENCE: 9
gcaagcatac ggccgttcgc cgtccttctg tcttaaatgg attttgg                   47

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: modified
      primer B

<400> SEQUENCE: 10
acccacatcc gcacccacac aggcggttct ggcgagaagc cttttgcc                  48

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: modified
      primer D
```

```
<400> SEQUENCE: 11
cccgccatat ccgcatccac acaggcggtt ctggccagaa gcccttccag            50

<210> SEQ ID NO 12
<211> LENGTH: 57
<212> TYPE: DNA
<213> ORGANISM: Artificial Sequence
<220> FEATURE:
<223> OTHER INFORMATION: Description of Artificial Sequence: modified
      primer B

<400> SEQUENCE: 12
acccacatcc gcacccacac aggcggttct ggcggttctg gcgagaagcc ttttgcc    57

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: modified
      primer D

<400> SEQUENCE: 13
cccgccatat ccgcatccac acaggcggtt ctggcggttc tggccagaag cccttccag  59

<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence: bsA

<400> SEQUENCE: 14 gcgtgggcg                                                          9

<210> SEQ ID NO 15
<211> LENGTH: 9
<212> TYPE: DNA
<213> ORGANISM: Artificial Sequence
<220> FEATURE:
<223> OTHER INFORMATION: Description of Artificial Sequence: bsB

<400> SEQUENCE: 15 gcggacgcg                                                          9

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: bsC

<400> SEQUENCE: 16
gcggacgcgg cgtgggcg                                               18

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: bsD

<400> SEQUENCE: 17
gcggactgcg gcgtttgggcg                                            20
```

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: bsE

<400> SEQUENCE: 18
gcggactcgc ggcgtctggg cg                                             22

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: bsF

<400> SEQUENCE: 19
gcggactgcg gcgtgggcg                                                 19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: bsG

<400> SEQUENCE: 20
gcggacgcgg cgttgggcg                                                 19

<210> SEQ ID NO 21
<211> LENGTH: 543
<212> TYPE: DNA
<213> ORGANISM: Artificial Sequence
<220> FEATURE:
<223> OTHER INFORMATION: Description of Artificial Sequence: ZIF-GAC
      fusion construct

<400> SEQUENCE: 21
atggcagaac gcccgtatgc ttgccctgtc gagtcctgcg atcgccgctt ttctcgctcg    60
gatgagctta cccgccatat ccgcatccac acaggccaga agcccttcca gtgtcgaatc   120
tgcatgcgta acttcagtcg tagtgaccac cttaccaccc acatccgcac ccacacaggc   180
gagaagcctt ttgcctgtga catttgtggg aggaagtttg ccaggagtga tgaacgcaag   240
aggcatacca aaatccattt aagacagaag gacggcgaac ggccgtatgc ttgccctgtc   300
gagtcctgcg atcgccgctt ttctcgctcg gatgagctta cccgccatat ccgcatccac   360
acaggccaga agcccttcca gtgtcgaatc tgcatgcgta acttcagtga tagaagcaat   420
cttgaacgtc acacgaggac ccacacaggc gagaagcctt ttgcctgtga catttgtggg   480
aggaagtttg ccaggagtga tgaacgcaag aggcatacca aaatccattt aagacagaag   540
gac                                                                543

<210> SEQ ID NO 22
<211> LENGTH: 537
<212> TYPE: DNA
<213> ORGANISM: Artificial Sequence
<220> FEATURE:
<223> OTHER INFORMATION: Description of Artificial Sequence: 3x2F ZGS
      construct

<400> SEQUENCE: 22

```
atggcagaac gcccgtatgc ttgccctgtc gagtcctgcg atcgccgctt ttctcgctcg      60
gatgagctta cccgccatat ccgcatccac acaggccaga agcccttcca gtgtcgaatc     120
tgcatgcgta acttcagtcg tagtgaccac cttaccaccc acatccgcac ccacacaggt     180
ggcgagaagc cttttgcctg tgacatttgt gggaggaagt ttgccaggag tgatgaacgc     240
aagaggcata ccaaaatcca taccggtgaa cggccgtatg cttgccctgt cgagtcctgc     300
gatcgccact tttctcgctc ggatgagctt acccgccata tccgcatcca cacaggtggc     360
cagaagccct tccagtgtcg aatctgcatg cgtaacttca gtgatagaag caatcttgaa     420
cgtcacacga ggacccacac aggcgagaag ccttttgcct gtgacatttg tgggaggaag     480
tttgccagga gtgatgaacg caagaggcat accaaaatcc atttaagaca gaaggac        537
```

<210> SEQ ID NO 23
<211> LENGTH: 549
<212> TYPE: DNA
<213> ORGANISM: Artificial Sequence
<220> FEATURE:
<223> OTHER INFORMATION: Description of Artificial Sequence: 3x2F ZGL
      construct

<400> SEQUENCE: 23

```
atggcagaac gcccgtatgc ttgccctgtc gagtcctgcg atcgccgctt ttctcgctcg      60
gatgagctta cccgccatat ccgcatccac acaggccaga agcccttcca gtgtcgaatc     120
tgcatgcgta acttcagtcg tagtgaccac cttaccaccc acatccgcac ccacacaggc     180
ggttctggcg agaagccttt tgcctgtgac atttgtggga ggaagtttgc caggagtgat     240
gaacgcaaga ggcataccaa aatccatacc ggtgaacggc cgtatgcttg ccctgtcgag     300
tcctgcgatc gccactttc tcgctcggat gagcttaccc gccatatccg catccacaca     360
ggcggttctg gccagaagcc cttccagtgt cgaatctgca tgcgtaactt cagtgataga     420
agcaatcttg aacgtcacac gaggacccac acaggcgaga agccttttgc ctgtgacatt     480
tgtgggagga gtttgccag gagtgatgaa cgcaagaggc ataccaaaat ccatttaaga     540
cagaaggac                                                             549
```

<210> SEQ ID NO 24
<211> LENGTH: 567
<212> TYPE: DNA
<213> ORGANISM: Artificial Sequence
<220> FEATURE:
<223> OTHER INFORMATION: Description of Artificial Sequence: 3x2F ZGXL
      construct

<400> SEQUENCE: 24

```
atggcagaac gcccgtatgc ttgccctgtc gagtcctgcg atcgccgctt ttctcgctcg      60
gatgagctta cccgccatat ccgcatccac acaggccaga agcccttcca gtgtcgaatc     120
tgcatgcgta acttcagtcg tagtgaccac cttaccaccc acatccgcac ccacacaggc     180
ggttctggcg gttctggcga gaagcctttt gcctgtgaca tttgtgggag gaagtttgcc     240
aggagtgatg aacgcaagag gcataccaaa atccataccg gtgaacggcc gtatgcttgc     300
cctgtcgagt cctgcgatcg ccactttct cgctcggatg agcttacccg ccatatccgc     360
atccacacag gcggttctgg cggttctggc cagaagccct tccagtgtcg aatctgcatg     420
cgtaacttca gtgatagaag caatcttgaa cgtcacacga ggacccacac aggcgagaag     480
``` cctttttgcct gtgacatttg tgggaggaag tttgccagga gtgatgaacg caagaggcat    540
accaaaatcc atttaagaca gaaggac                                        567

<210> SEQ ID NO 25
<211> LENGTH: 543
<212> TYPE: DNA
<213> ORGANISM: Artificial Sequence
<220> FEATURE:
<223> OTHER INFORMATION: Description of Artificial Sequence: 3x2F ZGSL
      construct

<400> SEQUENCE: 25
atggcagaac gcccgtatgc ttgccctgtc gagtcctgcg atcgccgctt ttctcgctcg     60
gatgagctta cccgccatat ccgcatccac acaggccaga agcccttcca gtgtcgaatc    120
tgcatgcgta acttcagtcg tagtgaccac cttaccaccc catccgcac ccacacaggt     180 ggcgagaagc cttttgcctg tgacatttgt gggaggaagt ttgccaggag tgatgaacgc    240
aagaggcata ccaaaatcca taccggtgaa cggccgtatg cttgccctgt cgagtcctgc    300
gatcgccact tttctcgctc ggatgagctt acccgccata tccgcatcca cacaggcggt    360
tctggccaga agcccttcca gtgtcgaatc tgcatgcgta acttcagtga tagaagcaat    420
cttgaacgtc acacgaggac ccacacaggc gagaagcctt tgcctgtga catttgtggg    480 aggaagtttg ccaggagtga tgaacgcaag aggcatacca aaatccattt aagacagaag    540
gac                                                                  543

<210> SEQ ID NO 26
<211> LENGTH: 543
<212> TYPE: DNA
<213> ORGANISM: Artificial Sequence
<220> FEATURE:
<223> OTHER INFORMATION: Description of Artificial Sequence: 3x2F ZGLS
      construct

<400> SEQUENCE: 26
atggcagaac gcccgtatgc ttgccctgtc gagtcctgcg atcgccgctt ttctcgctcg     60
gatgagctta cccgccatat ccgcatccac acaggccaga agcccttcca gtgtcgaatc    120
tgcatgcgta acttcagtcg tagtgaccac cttaccaccc catccgcac ccacacaggc     180 ggttctggcg agaagccttt tgcctgtgac atttgtggga ggaagtttgc caggagtgat    240
gaacgcaaga ggcataccaa aatccatacc ggtgaacggc cgtatgcttg ccctgtcgag    300
tcctgcgatc gccactttc tcgctcggat gagcttaccc gccatatccg catccacaca    360
ggtggccaga agcccttcca gtgtcgaatc tgcatgcgta acttcagtga tagaagcaat    420
cttgaacgtc acacgaggac ccacacaggc gagaagcctt tgcctgtga catttgtggg    480 aggaagtttg ccaggagtga tgaacgcaag aggcatacca aaatccattt aagacagaag    540
gac                                                                  543

<210> SEQ ID NO 27
<211> LENGTH: 279
<212> TYPE: DNA
<213> ORGANISM: Artificial Sequence
<220> FEATURE:
<223> OTHER INFORMATION: Description of Artificial Sequence: 3x1F ZIF
      construct -continued

<400> SEQUENCE: 27

```
atggcagaac gcccgtatgc ttgccctgtc gagtcctgcg atcgccgctt ttctcgctcg      60
gatgagctta cccgccatat ccgcatccac acaggtggcc agaagcccct tccagtgtcga    120 atctgcatgc gtaacttcag tcgtagtgac caccttacca cccacatccg cacccacaca    180
ggtggcgaga agccttttgc ctgtgacatt tgtgggagga agtttgccag gagtgatgaa    240
cgcaagaggc ataccaaaat ccatttaaga cagaaggac                           279
```

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: HA-antibody
  epitope tag

<400> SEQUENCE: 28

Tyr Pro Tyr Asp Val Pro Asp Tyr Ala
 1               5

<210> SEQ ID NO 29
<211> LENGTH: 54
<212> TYPE: DNA
<213> ORGANISM: Artificial Sequence
<220> FEATURE:
<223> OTHER INFORMATION: Description of Artificial Sequence: Primer A

<400> SEQUENCE: 29

```
acttcggaat tcgcggccca gccggcccat atgggagaga aggcgctgcc ggtg            54
```

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Primer a

<400> SEQUENCE: 30

```
gcaagcatac ggcagctgct gtgtgtgact g                                    31
```

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Primer B

<400> SEQUENCE: 31

```
acacagcagc tgccgtatgc ttgccctgtc gagtcc                               36
```

<210> SEQ ID NO 32
<211> LENGTH: 53
<212> TYPE: DNA
<213> ORGANISM: Artificial Sequence
<220> FEATURE:
<223> OTHER INFORMATION: Description of Artificial Sequence: Primer b

<400> SEQUENCE: 32

```
gagtcattca gctttgcgg ccgcttagtc cttctgtctt aaatggattt tgg             53
```

<210> SEQ ID NO 33
<211> LENGTH: 53
<212> TYPE: DNA
<213> ORGANISM: Artificial Sequence

```
<220> FEATURE:
<223> OTHER INFORMATION: Description of Artificial Sequence: Primer C

<400> SEQUENCE: 33
acttcggaat tcgcggccca gccggcccat atggcagaac gcccgtatgc ttg         53

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: primer c

<400> SEQUENCE: 34
cacatagacg cagatcttga tgttatggat tttggtatgc ctcttgcg              48

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Primer D

<400> SEQUENCE: 35
cataacatca agatctgcgt ctatgtg                                     27

<210> SEQ ID NO 36
<211> LENGTH: 53
<212> TYPE: DNA
<213> ORGANISM: Artificial Sequence
<220> FEATURE:
<223> OTHER INFORMATION: Description of Artificial Sequence: primer d

<400> SEQUENCE: 36
gagtcattca agctttgcgg ccgcttagtc cttctgtctt aaatggattt tgg         53

<210> SEQ ID NO 37
<211> LENGTH: 84
<212> TYPE: DNA
<213> ORGANISM: Artificial Sequence
<220> FEATURE:
<223> OTHER INFORMATION: Description of Artificial Sequence:
       complementary oligonucleotide

<400> SEQUENCE: 37
ggccgttcca gtgtcgaatc tgcatgcgta acttcagttc tagtagctct cttaccagcc  60
acatccgcac ccacacaggt gagc                                         84

<210> SEQ ID NO 38
<211> LENGTH: 84
<212> TYPE: DNA
<213> ORGANISM: Artificial Sequence
<220> FEATURE:
<223> OTHER INFORMATION: Description of Artificial Sequence:
       complementary oligonucleotide

<400> SEQUENCE: 38
ggccgctcac ctgtgtgggt gcggatgtgg ctggtaagag agctactaga actgaagtta  60
cgcatgcaga ttcgacactg gaac                                         84

<210> SEQ ID NO 39
<211> LENGTH: 25
<212> TYPE: DNA
<213> ORGANISM: Artificial Sequence
```

```
<220> FEATURE:
<223> OTHER INFORMATION: Description of Artificial Sequence: bsA1

<400> SEQUENCE: 39
gcgtgggcgt acctggatgg gagac                                          25

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: bsB1

<400> SEQUENCE: 40
gcgtgggcgg tacctggatg ggagac                                         26

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: bsC1

<400> SEQUENCE: 41
gcgtgggcga gtacctggat gggagac                                        27

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: bsD1

<400> SEQUENCE: 42
gcgtgggcgt agtacctgga tgggagac                                       28

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence: bsE1

<400> SEQUENCE: 43
gcgtgggcgt tagtacctgg atgggagac                                      29

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: bsF1

<400> SEQUENCE: 44
gcgtgggcgg ttagtacctg gatgggagac                                     30

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: bsG1

<400> SEQUENCE: 45
gcgtgggcgc ttgacggatg ggagac                                         26
```

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: bsH1

<400> SEQUENCE: 46
gcgtgggcga aaaaggatg ggagac                                26

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: bsA2

<400> SEQUENCE: 47
gcgtgggcgt acctggcgga cgcg                                  24

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: bsB2

<400> SEQUENCE: 48
gcgtgggcgg tacctggcgg acgcg                                 25

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: bsC2

<400> SEQUENCE: 49
gcgtgggcga gtacctggcg gacgcg                                26

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: bsD2

<400> SEQUENCE: 50
gcgtgggcgt agtacctggc ggacgcg                               27

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: bsE2

<400> SEQUENCE: 51
gcgtgggcgt tagtacctgg cggacgcg                              28

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: bsF2

<400> SEQUENCE: 52
gcgtgggcgg ttagtacctg gcggacgcg                                              29

<210> SEQ ID NO 53
<211> LENGTH: 660
<212> TYPE: DNA
<213> ORGANISM: Artificial Sequence
<220> FEATURE:
<223> OTHER INFORMATION: Description of Artificial Sequence:
      TF(F1-4)-ZIF fusion construct

<400> SEQUENCE: 53
atgggagaga aggcgctgcc ggtggtgtat aagcggtaca tctgctcttt cgccgactgc    60
ggcgctgctt ataacaagaa ctggaaactg caggcgcatc tgtgcaaaca cacaggagag   120
aaaccatttc catgtaagga agaaggatgt gagaaaggct ttacctcgct tcatcactta   180
acccgccact cactcactca tactggcgag aaaaacttca catgtgactc ggatggatgt   240
gacttgagat ttactacaaa ggcaaacatg aagaagcact ttaacagatt ccataacatc   300
aagatctgcg tctatgtgtg ccattttgag aactgtggca agcattcaa gaaacacaat    360 caattaaagg ttcatcagtt cagtcacaca cagcagctgc cgtatgcttg ccctgtcgag   420
tcctgcgatc gccgcttttc tgctcggat gagcttaccc gccatatccg catccacaca    480
ggccagaagc ccttccagtg tcgaatctgc atgcgtaact tcagtcgtag tgaccacctt   540
accacccaca tccgcaccca cacaggcgag aagccttttg cctgtgacat tgtgggagg    600 aagtttgcca ggagtgatga acgcaagagg cataccaaaa tccatttaag acagaaggac   660

<210> SEQ ID NO 54
<211> LENGTH: 639
<212> TYPE: DNA
<213> ORGANISM: Artificial Sequence
<220> FEATURE:
<223> OTHER INFORMATION: Description of Artificial Sequence: GAC-F4-ZIF
      construct

<400> SEQUENCE: 54
atggcagaac gcccgtatgc ttgccctgtc gagtcctgcg atcgccgctt ttctcgctcg    60
gatgagctta cccgccatat ccgcatccac acaggccaga agcccttcca gtgtcgaatc   120
tgcatgcgta acttcagtga tagaagcaat cttgaacgtc acacgaggac ccacacaggc   180
gagaagcctt ttgcctgtga catttgtggg aggaagtttg ccaggagtga tgaacgcaag   240
aggcatacca aaatccattt aagacagaag gacaacatca gatctgcgt ctatgtgtgc    300 cattttgaga actgtggcaa agcattcaag aaacacaatc aattaaaggt tcatcagttc   360
agtcacacac agcagctgcc gtatgcttgc cctgtcgagt cctgcgatcg ccgcttttct   420
cgctcggatg agcttacccg ccatatccgc atccacacag gccagaagcc cttccagtgt   480
cgaatctgca tgcgtaactt cagtcgtagt gaccacctta ccacccacat ccgcacccac   540
acaggcgaga agccttttgc ctgtgacatt tgtgggagga gtttgccag gagtgatgaa    600 cgcaagaggc ataccaaaat ccatttaaga cagaaggac                          639

<210> SEQ ID NO 55
<211> LENGTH: 615
<212> TYPE: DNA
<213> ORGANISM: Artificial Sequence
<220> FEATURE:
<223> OTHER INFORMATION: Description of Artificial Sequence: ZIF-ZnF-GAC
      construct

<400> SEQUENCE: 55

```
atggcagaac gcccgtatgc ttgccctgtc gagtcctgcg atcgccgctt ttctcgctcg      60
gatgagctta cccgccatat ccgcatccac acaggccaga agcccttcca gtgtcgaatc     120
tgcatgcgta acttcagtcg tagtgaccac cttaccaccc acatccgcac ccacacaggc     180
gagaagcctt ttgcctgtga catttgtggg aggaagtttg ccaggagtga tgaacgcaag     240
aggcatacca aaatccatac cggtgaacgg ccgttccagt gtcgaatctg catgcgtaac     300
ttcagttcta gtagctctct taccagccac atccgcaccc acacaggtga gcggccgtat     360
gcttgccctg tcgagtcctg cgatcgccgc ttttctcgct cggatgagct acccgccat      420 atccgcatcc acacaggcca aagcccttc cagtgtcgaa tctgcatgcg taacttcagt     480
gatagaagca atcttgaacg tcacacgagg acccacacag gcgagaagcc ttttgcctgt     540
gacatttgtg ggaggaagtt tgccaggagt gatgaacgca agaggcatac caaaatccat     600
ttaagacaga aggac                                                     615
```

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: canonical
      linker sequence variant

<400> SEQUENCE: 56

Gly Glu Lys Pro
 1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: canonical
      linker sequence variant

<400> SEQUENCE: 57

Gly Glu Arg Pro
 1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: canonical
      linker sequence variant

<400> SEQUENCE: 58

Gly Gln Lys Pro
 1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: canonical
      linker sequence variant

<400> SEQUENCE: 59

Gly Gln Arg Pro
 1

```
<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: canonical
      linker sequence variant

<400> SEQUENCE: 60

Gly Gly Glu Lys Pro
 1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: canonical
      linker sequence variant

<400> SEQUENCE: 61

Gly Gly Gln Lys Pro
 1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: canonical
      linker sequence variant

<400> SEQUENCE: 62

Gly Gly Ser Gly Glu Lys Pro
 1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: canonical
      linker sequence variant

<400> SEQUENCE: 63

Gly Gly Ser Gly Gln Lys Pro
 1               5

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: canonical
      linker sequence variant

<400> SEQUENCE: 64

Gly Gly Ser Gly Gly Ser Gly Glu Lys Pro
 1               5                  10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: canonical
      linker sequence variant
```

<400> SEQUENCE: 65

Gly Gly Ser Gly Gly Ser Gly Gln Lys Pro
 1               5                  10

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 66

Leu Arg Gln Lys Asp Gly Glu Arg Pro
 1               5

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: binding
      site Z2G

<400> SEQUENCE: 67
gcggacgcgg tgcgtgggcg                                                 20

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: binding
      site Z3G

<400> SEQUENCE: 68
gcggacgcga gtgcgtgggc g                                               21

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: binding
      site Z4G

<400> SEQUENCE: 69
gcggacgcgt agtgcgtggg cg                                              22

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: binding
      site Z5G

<400> SEQUENCE: 70
gcggacgcgc tagtgcgtgg gcg                                             23

<210> SEQ ID NO 71
<211> LENGTH: 15
<212> TYPE: DNA
<213> ORGANISM: Artificial Sequence
<220> FEATURE:
<223> OTHER INFORMATION: Description of Artificial Sequence: bs1

```
<400> SEQUENCE: 71
gcggacgcgt gggcg                                                    15

<210> SEQ ID NO 72
<211> LENGTH: 16
<212> TYPE: DNA
<213> ORGANISM: Artificial Sequence
<220> FEATURE:
<223> OTHER INFORMATION: Description of Artificial Sequence: bs2

<400> SEQUENCE: 72
gcggactgcg tgggcg                                                   16

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence: bs3

<400> SEQUENCE: 73
gcggactcgc gtgggcg                                                  17

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: bs4

<400> SEQUENCE: 74
gcggacatcg cgtgggcg                                                 18

<210> SEQ ID NO 75
<211> LENGTH: 31
<212> TYPE: PRT
<213> ORGANISM: Artificial Sequence
<220> FEATURE:
<223> OTHER INFORMATION: Description of Artificial Sequence: preferred
      zinc finger framework
<220> FEATURE:
<221> NAME/KEY: SITE
<222> LOCATION: (1)..(2)
<223> OTHER INFORMATION: 'Xaa' may be present or absent
<220> FEATURE:
<221> NAME/KEY: SITE
<222> LOCATION: (1)..(2)
<223> OTHER INFORMATION: 'Xaa' = any amino acid
<220> FEATURE:
<221> NAME/KEY: SITE
<222> LOCATION: (4)..(8)
<223> OTHER INFORMATION: 'Xaa' = any amino acid
<220> FEATURE:
<221> NAME/KEY: SITE
<222> LOCATION: (5)..(8)
<223> OTHER INFORMATION: 'Xaa' may be present or absent
<220> FEATURE:
<221> NAME/KEY: SITE
<222> LOCATION: (10)..(23)
<223> OTHER INFORMATION: 'Xaa' = any amino acid
<220> FEATURE:
<221> NAME/KEY: SITE
<222> LOCATION: (19)..(23)
<223> OTHER INFORMATION: 'Xaa' may be present or absent
<220> FEATURE:
<221> NAME/KEY: SITE
<222> LOCATION: (25)..(30)
<223> OTHER INFORMATION: 'Xaa' = any amino acid
```

```
<220> FEATURE:
<221> NAME/KEY: SITE
<222> LOCATION: (28)..(30)
<223> OTHER INFORMATION: 'Xaa' may be present or absent
<220> FEATURE:
<221> NAME/KEY: SITE
<222> LOCATION: (31)
<223> OTHER INFORMATION: 'Xaa' = His or Cys

<400> SEQUENCE: 75

Xaa Xaa Cys Xaa Xaa Xaa Xaa Xaa Cys Xaa Xaa Xaa Xaa Xaa Xaa Xaa
 1               5                  10                  15

Xaa Xaa Xaa Xaa Xaa Xaa Xaa His Xaa Xaa Xaa Xaa Xaa Xaa Xaa
             20                  25                  30

<210> SEQ ID NO 76
<211> LENGTH: 24
<212> TYPE: PRT
<213> ORGANISM: Artificial Sequence
<220> FEATURE:
<223> OTHER INFORMATION: Description of Artificial Sequence: binding
      motif
<220> FEATURE:
<221> NAME/KEY: SITE
<222> LOCATION: (1)
<223> OTHER INFORMATION: 'Xaa' = any amino acid
<220> FEATURE:
<221> NAME/KEY: SITE
<222> LOCATION: (3)..(6)
<223> OTHER INFORMATION: 'Xaa' = any amino acid
<220> FEATURE:
<221> NAME/KEY: SITE
<222> LOCATION: (5)..(6)
<223> OTHER INFORMATION: 'Xaa' may be present or absent
<220> FEATURE:
<221> NAME/KEY: SITE
<222> LOCATION: (8)..(10)
<223> OTHER INFORMATION: 'Xaa' = any amino acid
<220> FEATURE:
<221> NAME/KEY: SITE
<222> LOCATION: (10)
<223> OTHER INFORMATION: 'Xaa' may be present or absent
<220> FEATURE:
<221> NAME/KEY: SITE
<222> LOCATION: (12)..(16)
<223> OTHER INFORMATION: 'Xaa' = any amino acid
<220> FEATURE:
<221> NAME/KEY: SITE
<222> LOCATION: (18)..(19)
<223> OTHER INFORMATION: 'Xaa' = any amino acid
<220> FEATURE:
<221> NAME/KEY: SITE
<222> LOCATION: (21)..(23)
<223> OTHER INFORMATION: 'Xaa' = any amino acid

<400> SEQUENCE: 76

Xaa Cys Xaa Xaa Xaa Xaa Cys Xaa Xaa Xaa Phe Xaa Xaa Xaa Xaa Xaa
 1               5                  10                  15

Leu Xaa Xaa His Xaa Xaa Xaa His
             20

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: consensus
      structure
```

```
<400> SEQUENCE: 77

Pro Tyr Lys Cys Pro Glu Cys Gly Lys Ser Phe Ser Gln Lys Ser Asp
 1               5                  10                  15

Leu Val Lys His Gln Arg Thr His Thr
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: consensus
      structure

<400> SEQUENCE: 78

Pro Tyr Lys Cys Ser Glu Cys Gly Lys Ala Phe Ser Gln Lys Ser Asn
 1               5                  10                  15

Leu Thr Arg His Gln Arg Ile His Thr
            20                  25

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: leader
      peptide

<400> SEQUENCE: 79

Met Ala Glu Glu Lys Pro
 1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: linker

<400> SEQUENCE: 80

Asn Ile Lys Ile Cys Val
 1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: linker

<400> SEQUENCE: 81

Thr Gln Gln Leu Pro
 1               5

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: linker
```

-continued

```
<400> SEQUENCE: 82

Thr Gly Gly Ser Gly Gly Ser Gly Gly Ser Gly Gly Ser Gly Gly Ser
 1               5                   10                  15

Gly Glu Arg Pro
            20

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: inserted
      residues

<400> SEQUENCE: 83

Gly Gly Ser Gly Gly Ser
 1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: flexible
      linker

<400> SEQUENCE: 84

Thr Gly Glu Arg Pro
 1               5

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: TF5Z
<220> FEATURE:
<221> NAME/KEY: misc_feature
<222> LOCATION: (10)..(14)
<223> OTHER INFORMATION: any nucleotide

<400> SEQUENCE: 85
gcgtgggcgn nnnnggatgg gagac                                           25

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: TF6Z
<220> FEATURE:
<221> NAME/KEY: misc_feature
<222> LOCATION: (10)..(15)
<223> OTHER INFORMATION: any nucleotide

<400> SEQUENCE: 86
gcgtgggcgn nnnnnggatg ggagac                                          26

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: TF7Z
<220> FEATURE:
<221> NAME/KEY: misc_feature
<222> LOCATION: (10)..(16)
<223> OTHER INFORMATION: any nucleotide
```

```
<400> SEQUENCE: 87
gcgtgggcgn nnnnnnggat gggagac                                              27

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: TF8Z
<220> FEATURE:
<221> NAME/KEY: misc_feature
<222> LOCATION: (10)..(17)
<223> OTHER INFORMATION: any nucleotide

<400> SEQUENCE: 88
gcgtgggcgn nnnnnngga tgggagac                                              28

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence: TF9Z
<220> FEATURE:
<221> NAME/KEY: misc_feature
<222> LOCATION: (10)..(18)
<223> OTHER INFORMATION: any nucleotide

<400> SEQUENCE: 89
gcgtgggcgn nnnnnnnngg atgggagac                                            29

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Z1M
<220> FEATURE:
<221> NAME/KEY: misc_feature
<222> LOCATION: (10)
<223> OTHER INFORMATION: any nucleotide

<400> SEQUENCE: 90
gcggacgcgn gcgtgggcg                                                       19

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Z2M
<220> FEATURE:
<221> NAME/KEY: misc_feature
<222> LOCATION: (10)..(11)
<223> OTHER INFORMATION: any nucleotide

<400> SEQUENCE: 91
gcggacgcgn ngcgtgggcg                                                      20

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Z3M
<220> FEATURE:
<221> NAME/KEY: misc_feature
<222> LOCATION: (10)..(12)
<223> OTHER INFORMATION: any nucleotide
```

```
<400> SEQUENCE: 92
gcggacgcgn nngcgtgggc g                                           21

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Z4M
<220> FEATURE:
<221> NAME/KEY: misc_feature
<222> LOCATION: (10)..(13)
<223> OTHER INFORMATION: any nucleotide

<400> SEQUENCE: 93
gcggacgcgn nnngcgtggg cg                                          22

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Z5M
<220> FEATURE:
<221> NAME/KEY: misc_feature
<222> LOCATION: (10)..(14)
<223> OTHER INFORMATION: any nucleotide

<400> SEQUENCE: 94
gcggacgcgn nnnngcgtgg gcg                                         23

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Z6M
<220> FEATURE:
<221> NAME/KEY: misc_feature
<222> LOCATION: (10)..(15)
<223> OTHER INFORMATION: any nucleotide

<400> SEQUENCE: 95
gcggacgcgn nnnnngcgtg ggcg                                        24

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Z7M
<220> FEATURE:
<221> NAME/KEY: misc_feature
<222> LOCATION: (10)..(16)
<223> OTHER INFORMATION: any nucleotide

<400> SEQUENCE: 96
gcggacgcgn nnnnnngcgt gggcg                                       25

<210> SEQ ID NO 97
<211> LENGTH: 26
<212> TYPE: DNA
<213> ORGANISM: Artificial Sequence
<220> FEATURE:
<223> OTHER INFORMATION: Description of Artificial Sequence: Z8M
<220> FEATURE:
<221> NAME/KEY: misc_feature
<222> LOCATION: (10)..(17)
<223> OTHER INFORMATION: any nucleotide
```

```
<400> SEQUENCE: 97
gcggacgcgn nnnnnnngcg tgggcg                                          26

<210> SEQ ID NO 98
<211> LENGTH: 27
<212> TYPE: DNA
<213> ORGANISM: Artificial Sequence
<220> FEATURE:
<223> OTHER INFORMATION: Description of Artificial Sequence: Z9M
<220> FEATURE:
<221> NAME/KEY: misc_feature
<222> LOCATION: (10)..(18)
<223> OTHER INFORMATION: any nucleotide

<400> SEQUENCE: 98
gcggacgcgn nnnnnnnngc gtgggcg                                         27

<210> SEQ ID NO 99
<211> LENGTH: 28
<212> TYPE: DNA
<213> ORGANISM: Artificial Sequence
<220> FEATURE:
<223> OTHER INFORMATION: Description of Artificial Sequence: Z10M
<220> FEATURE:
<221> NAME/KEY: misc_feature
<222> LOCATION: (10)..(19)
<223> OTHER INFORMATION: any nucleotide

<400> SEQUENCE: 99
gcggacgcgn nnnnnnnnng cgtgggcg                                        28

<210> SEQ ID NO 100
<211> LENGTH: 45
<212> TYPE: DNA
<213> ORGANISM: Artificial Sequence
<220> FEATURE:
<223> OTHER INFORMATION: Description of Artificial Sequence: ANF1L12

<400> SEQUENCE: 100
cagttgcgtc tagacgccgc catggcggag aggccctacg catgc             45

<210> SEQ ID NO 101
<211> LENGTH: 56
<212> TYPE: DNA
<213> ORGANISM: Artificial Sequence
<220> FEATURE:
<223> OTHER INFORMATION: Description of Artificial Sequence: ANF2L123

<400> SEQUENCE: 101
cagttgcgtc tagacgccgc catggctgag aggcccttcc agtgtcgaat ctgcat       56

<210> SEQ ID NO 102
<211> LENGTH: 45
<212> TYPE: DNA
<213> ORGANISM: Artificial Sequence
<220> FEATURE:
<223> OTHER INFORMATION: Description of Artificial Sequence: ANF1L23

<400> SEQUENCE: 102
cagttgcgtc tagacgccgc catggcagaa cgcccatatg cttgc             45

<210> SEQ ID NO 103
<211> LENGTH: 39
<212> TYPE: DNA
<213> ORGANISM: Artificial Sequence
<220> FEATURE:
<223> OTHER INFORMATION: Description of Artificial Sequence: ACF3L12
```

<400> SEQUENCE: 103
gcggccgccg gccgctggcc tcctgtatgg attttggta        39

<210> SEQ ID NO 104
<211> LENGTH: 40
<212> TYPE: DNA
<213> ORGANISM: Artificial Sequence
<220> FEATURE:
<223> OTHER INFORMATION: Description of Artificial Sequence: ACF2L123

<400> SEQUENCE: 104
catggcattc ggccgctcgc ctcctgtgtg ggtgcggatg        40

<210> SEQ ID NO 105
<211> LENGTH: 39
<212> TYPE: DNA
<213> ORGANISM: Artificial Sequence
<220> FEATURE:
<223> OTHER INFORMATION: Description of Artificial Sequence: ACF3L23

<400> SEQUENCE: 105
gcggccgccg gccgttgtcc gcccgtgtgt atcttggta        39

<210> SEQ ID NO 106
<211> LENGTH: 35
<212> TYPE: DNA
<213> ORGANISM: Artificial Sequence
<220> FEATURE:
<223> OTHER INFORMATION: Description of Artificial Sequence: BNF1L12

<400> SEQUENCE: 106
tcaagctgcc ggccgtacgc atgccctgtc gagtc        35

<210> SEQ ID NO 107
<211> LENGTH: 35
<212> TYPE: DNA
<213> ORGANISM: Artificial Sequence
<220> FEATURE:
<223> OTHER INFORMATION: Description of Artificial Sequence: BNF2L123

<400> SEQUENCE: 107
agctctcagc ggccgttcca gtgtcgaatc tgcat        35

<210> SEQ ID NO 108
<211> LENGTH: 35
<212> TYPE: DNA
<213> ORGANISM: Artificial Sequence
<220> FEATURE:
<223> OTHER INFORMATION: Description of Artificial Sequence: BNF1L23

<400> SEQUENCE: 108
tcaagctgac ggccgtatgc ttgccctgtc gagtc        35

<210> SEQ ID NO 109
<211> LENGTH: 34
<212> TYPE: DNA
<213> ORGANISM: Artificial Sequence
<220> FEATURE:
<223> OTHER INFORMATION: Description of Artificial Sequence: BCF3L12

<400> SEQUENCE: 109
cgcgtccttc tgggatcctg tatggatttt ggta        34

```
<210> SEQ ID NO 110
<211> LENGTH: 31
<212> TYPE: DNA
<213> ORGANISM: Artificial Sequence
<220> FEATURE:
<223> OTHER INFORMATION: Description of Artificial Sequence: BCF2L123

<400> SEQUENCE: 110
acccttctcg gatcctgtgt gggtgcggat g                                  31

<210> SEQ ID NO 111
<211> LENGTH: 35
<212> TYPE: DNA
<213> ORGANISM: Artificial Sequence
<220> FEATURE:
<223> OTHER INFORMATION: Description of Artificial Sequence: BCF3L23

<400> SEQUENCE: 111
ccgcatcttt ttgggatccc gtgtgtatct tggta                              35

<210> SEQ ID NO 112
<211> LENGTH: 39
<212> TYPE: DNA
<213> ORGANISM: Artificial Sequence
<220> FEATURE:
<223> OTHER INFORMATION: Description of Artificial Sequence: CNF1L12

<400> SEQUENCE: 112
tcaagctgca gatctgagag gccctacgca tgccctgtc                          39

<210> SEQ ID NO 113
<211> LENGTH: 44
<212> TYPE: DNA
<213> ORGANISM: Artificial Sequence
<220> FEATURE:
<223> OTHER INFORMATION: Description of Artificial Sequence: CNF2L123

<400> SEQUENCE: 113
acgtctacga gatctcagaa gcccttccag tgtcgaatct gcat                    44

<210> SEQ ID NO 114
<211> LENGTH: 39
<212> TYPE: DNA
<213> ORGANISM: Artificial Sequence
<220> FEATURE:
<223> OTHER INFORMATION: Description of Artificial Sequence: CNF1L23

<400> SEQUENCE: 114
tcaagctgaa gatctgaacg cccatatgct tgccctgtc                          39

<210> SEQ ID NO 115
<211> LENGTH: 45
<212> TYPE: DNA
<213> ORGANISM: Artificial Sequence
<220> FEATURE:
<223> OTHER INFORMATION: Description of Artificial Sequence: CCF3L12

<400> SEQUENCE: 115
catttaggaa ttccgggccg cgtccttctg tctcagatgg atttt                   45

<210> SEQ ID NO 116
<211> LENGTH: 49
<212> TYPE: DNA
<213> ORGANISM: Artificial Sequence
<220> FEATURE:
<223> OTHER INFORMATION: Description of Artificial Sequence: CCF2L123
```

```
<400> SEQUENCE: 116
catttaggaa ttccgggccg catccttctg gcgcaggtgg gtgcggatg                 49

<210> SEQ ID NO 117
<211> LENGTH: 43
<212> TYPE: DNA
<213> ORGANISM: Artificial Sequence
<220> FEATURE:
<223> OTHER INFORMATION: Description of Artificial Sequence: CCF3L23

<400> SEQUENCE: 117
catttaggaa ttccgggccg catcttttg gcgcaggtgt atc                       43

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: NXbaAMP

<400> SEQUENCE: 118
cagttgcgtc tagacgccgc c                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: CEcoAMP

<400> SEQUENCE: 119
catttaggaa ttccgggccg c                                              21

<210> SEQ ID NO 120
<211> LENGTH: 29
<212> TYPE: DNA
<213> ORGANISM: Artificial Sequence
<220> FEATURE:
<223> OTHER INFORMATION: Description of Artificial Sequence: Promoter
      Sequence

<400> SEQUENCE: 120
tccccgcccc agcggcgcat gcgccgcgc                                      29

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Promoter
      Sequence A

<400> SEQUENCE: 121
tccccgcccc agggcgcagc gccg                                           24

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: 11-9

<400> SEQUENCE: 122
ggccaggcgg caggggtt                                                  18
```

<210> SEQ ID NO 123
<211> LENGTH: 36
<212> TYPE: DNA
<213> ORGANISM: Artificial Sequence
<220> FEATURE:
<223> OTHER INFORMATION: Description of Artificial Sequence: 3x2CF3L23

<400> SEQUENCE: 123
gcggccgccg gccgctggcc cgtgtgtatc ttggta        36

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: linker

<400> SEQUENCE: 124

Thr Gly Gly Glu Lys Pro
 1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: linker

<400> SEQUENCE: 125

Thr Gly Gly Gln Lys Pro
 1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: linker

<400> SEQUENCE: 126

Thr Gly Gln Arg Pro
 1               5

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: 11-9mut1

<400> SEQUENCE: 127
ggccaggcgg cagggacc        18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: 11-9mut3

<400> SEQUENCE: 128
ggccaggcga tgggggtt        18

<210> SEQ ID NO 129
<211> LENGTH: 15
<212> TYPE: DNA
<213> ORGANISM: Artificial Sequence

```
<220> FEATURE:
<223> OTHER INFORMATION: Description of Artificial Sequence: 11-9del3

<400> SEQUENCE: 129
ggccaggcgg gggtt                                                    15

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 130
gcagagctct ctggctaact agag                                          24

<210> SEQ ID NO 131
<211> LENGTH: 181
<212> TYPE: PRT
<213> ORGANISM: Artificial Sequence
<220> FEATURE:
<223> OTHER INFORMATION: Description of Artificial Sequence: ZIF-GAC
      fusion construct

<400> SEQUENCE: 131
```

Met Ala Glu Arg Pro Tyr Ala Cys Pro Val Glu Ser Cys Asp Arg Arg
 1               5                  10                  15

Phe Ser Arg Ser Asp Glu Leu Thr Arg His Ile Arg Ile His Thr Gly
            20                  25                  30

Gln Lys Pro Phe Gln Cys Arg Ile Cys Met Arg Asn Phe Ser Arg Ser
        35                  40                  45

Asp His Leu Thr Thr His Ile Arg Thr His Thr Gly Glu Lys Pro Phe
    50                  55                  60

Ala Cys Asp Ile Cys Gly Arg Lys Phe Ala Arg Ser Asp Glu Arg Lys
65                  70                  75                  80

Arg His Thr Lys Ile His Leu Arg Gln Lys Asp Gly Glu Arg Pro Tyr
                85                  90                  95

Ala Cys Pro Val Glu Ser Cys Asp Arg Arg Phe Ser Arg Ser Asp Glu
            100                 105                 110

Leu Thr Arg His Ile Arg Ile His Thr Gly Gln Lys Pro Phe Gln Cys
        115                 120                 125

Arg Ile Cys Met Arg Asn Phe Ser Asp Arg Ser Asn Leu Glu Arg His
    130                 135                 140

Thr Arg Thr His Thr Gly Glu Lys Pro Phe Ala Cys Asp Ile Cys Gly
145                 150                 155                 160

Arg Lys Phe Ala Arg Ser Asp Glu Arg Lys Arg His Thr Lys Ile His
                165                 170                 175

Leu Arg Gln Lys Asp
            180

```
<210> SEQ ID NO 132
<211> LENGTH: 179
<212> TYPE: PRT
<213> ORGANISM: Artificial Sequence
<220> FEATURE:
<223> OTHER INFORMATION: Description of Artificial Sequence: 3x2F ZGS
      construct
```

<400> SEQUENCE: 132

```
Met Ala Glu Arg Pro Tyr Ala Cys Pro Val Glu Ser Cys Asp Arg Arg
 1               5                  10                  15

Phe Ser Arg Ser Asp Glu Leu Thr Arg His Ile Arg Ile His Thr Gly
            20                  25                  30

Gln Lys Pro Phe Gln Cys Arg Ile Cys Met Arg Asn Phe Ser Arg Ser
        35                  40                  45

Asp His Leu Thr Thr His Ile Arg Thr His Thr Gly Gly Glu Lys Pro
    50                  55                  60

Phe Ala Cys Asp Ile Cys Gly Arg Lys Phe Ala Arg Ser Asp Glu Arg
65                  70                  75                  80

Lys Arg His Thr Lys Ile His Thr Gly Glu Arg Pro Tyr Ala Cys Pro
                85                  90                  95

Val Glu Ser Cys Asp Arg His Phe Ser Arg Ser Asp Glu Leu Thr Arg
            100                 105                 110

His Ile Arg Ile His Thr Gly Gly Gln Lys Pro Phe Gln Cys Arg Ile
        115                 120                 125

Cys Met Arg Asn Phe Ser Asp Arg Ser Asn Leu Glu Arg His Thr Arg
    130                 135                 140

Thr His Thr Gly Glu Lys Pro Phe Ala Cys Asp Ile Cys Gly Arg Lys
145                 150                 155                 160

Phe Ala Arg Ser Asp Glu Arg Lys Arg His Thr Lys Ile His Leu Arg
                165                 170                 175

Gln Lys Asp
```

<210> SEQ ID NO 133
<211> LENGTH: 183
<212> TYPE: PRT
<213> ORGANISM: Artificial Sequence
<220> FEATURE:
<223> OTHER INFORMATION: Description of Artificial Sequence: 3x2F ZGL construct

<400> SEQUENCE: 133

```
Met Ala Glu Arg Pro Tyr Ala Cys Pro Val Glu Ser Cys Asp Arg Arg
 1               5                  10                  15

Phe Ser Arg Ser Asp Glu Leu Thr Arg His Ile Arg Ile His Thr Gly
            20                  25                  30

Gln Lys Pro Phe Gln Cys Arg Ile Cys Met Arg Asn Phe Ser Arg Ser
        35                  40                  45

Asp His Leu Thr Thr His Ile Arg Thr His Thr Gly Gly Ser Gly Glu
    50                  55                  60

Lys Pro Phe Ala Cys Asp Ile Cys Gly Arg Lys Phe Ala Arg Ser Asp
65                  70                  75                  80

Glu Arg Lys Arg His Thr Lys Ile His Thr Gly Glu Arg Pro Tyr Ala
                85                  90                  95

Cys Pro Val Glu Ser Cys Asp Arg His Phe Ser Arg Ser Asp Glu Leu
            100                 105                 110

Thr Arg His Ile Arg Ile His Thr Gly Gly Ser Gly Gln Lys Pro Phe
        115                 120                 125

Gln Cys Arg Ile Cys Met Arg Asn Phe Ser Asp Arg Ser Asn Leu Glu
    130                 135                 140

Arg His Thr Arg Thr His Thr Gly Glu Lys Pro Phe Ala Cys Asp Ile
145                 150                 155                 160
```

```
Cys Gly Arg Lys Phe Ala Arg Ser Asp Glu Arg Lys Arg His Thr Lys
            165                 170                 175

Ile His Leu Arg Gln Lys Asp
            180

<210> SEQ ID NO 134
<211> LENGTH: 189
<212> TYPE: PRT
<213> ORGANISM: Artificial Sequence
<220> FEATURE:
<223> OTHER INFORMATION: Description of Artificial Sequence: 3x2F ZGXL
      construct

<400> SEQUENCE: 134

Met Ala Glu Arg Pro Tyr Ala Cys Pro Val Glu Ser Cys Asp Arg Arg
 1               5                  10                  15

Phe Ser Arg Ser Asp Glu Leu Thr Arg His Ile Arg Ile His Thr Gly
            20                  25                  30

Gln Lys Pro Phe Gln Cys Arg Ile Cys Met Arg Asn Phe Ser Arg Ser
        35                  40                  45

Asp His Leu Thr Thr His Ile Arg Thr His Thr Gly Gly Ser Gly Gly
    50                  55                  60

Ser Gly Glu Lys Pro Phe Ala Cys Asp Ile Cys Gly Arg Lys Phe Ala
65                  70                  75                  80

Arg Ser Asp Glu Arg Lys Arg His Thr Lys Ile His Thr Gly Glu Arg
                85                  90                  95

Pro Tyr Ala Cys Pro Val Glu Ser Cys Asp Arg His Phe Ser Arg Ser
            100                 105                 110

Asp Glu Leu Thr Arg His Ile Arg Ile His Thr Gly Gly Ser Gly Gly
        115                 120                 125

Ser Gly Gln Lys Pro Phe Gln Cys Arg Ile Cys Met Arg Asn Phe Ser
    130                 135                 140

Asp Arg Ser Asn Leu Glu Arg His Thr Arg Thr His Thr Gly Glu Lys
145                 150                 155                 160

Pro Phe Ala Cys Asp Ile Cys Gly Arg Lys Phe Ala Arg Ser Asp Glu
                165                 170                 175

Arg Lys Arg His Thr Lys Ile His Leu Arg Gln Lys Asp
            180                 185

<210> SEQ ID NO 135
<211> LENGTH: 181
<212> TYPE: PRT
<213> ORGANISM: Artificial Sequence
<220> FEATURE:
<223> OTHER INFORMATION: Description of Artificial Sequence: 3x2F ZGSL
      construct

<400> SEQUENCE: 135

Met Ala Glu Arg Pro Tyr Ala Cys Pro Val Glu Ser Cys Asp Arg Arg
 1               5                  10                  15

Phe Ser Arg Ser Asp Glu Leu Thr Arg His Ile Arg Ile His Thr Gly
            20                  25                  30

Gln Lys Pro Phe Gln Cys Arg Ile Cys Met Arg Asn Phe Ser Arg Ser
        35                  40                  45

Asp His Leu Thr Thr His Ile Arg Thr His Thr Gly Gly Glu Lys Pro
    50                  55                  60

Phe Ala Cys Asp Ile Cys Gly Arg Lys Phe Ala Arg Ser Asp Glu Arg
65                  70                  75                  80
```

```
Lys Arg His Thr Lys Ile His Thr Gly Glu Arg Pro Tyr Ala Cys Pro
                85                  90                  95

Val Glu Ser Cys Asp Arg His Phe Ser Arg Ser Asp Glu Leu Thr Arg
            100                 105                 110

His Ile Arg Ile His Thr Gly Gly Ser Gly Gln Lys Pro Phe Gln Cys
        115                 120                 125

Arg Ile Cys Met Arg Asn Phe Ser Asp Arg Ser Asn Leu Glu Arg His
    130                 135                 140

Thr Arg Thr His Thr Gly Glu Lys Pro Phe Ala Cys Asp Ile Cys Gly
145                 150                 155                 160

Arg Lys Phe Ala Arg Ser Asp Glu Arg Lys Arg His Thr Lys Ile His
                165                 170                 175

Leu Arg Gln Lys Asp
            180

<210> SEQ ID NO 136
<211> LENGTH: 181
<212> TYPE: PRT
<213> ORGANISM: Artificial Sequence
<220> FEATURE:
<223> OTHER INFORMATION: Description of Artificial Sequence: 3x2F ZGLS
      construct

<400> SEQUENCE: 136

Met Ala Glu Arg Pro Tyr Ala Cys Pro Val Glu Ser Cys Asp Arg Arg
1               5                   10                  15

Phe Ser Arg Ser Asp Glu Leu Thr Arg His Ile Arg Ile His Thr Gly
            20                  25                  30

Gln Lys Pro Phe Gln Cys Arg Ile Cys Met Arg Asn Phe Ser Arg Ser
        35                  40                  45

Asp His Leu Thr Thr His Ile Arg Thr His Thr Gly Gly Ser Gly Glu
    50                  55                  60

Lys Pro Phe Ala Cys Asp Ile Cys Gly Arg Lys Phe Ala Arg Ser Asp
65                  70                  75                  80

Glu Arg Lys Arg His Thr Lys Ile His Thr Gly Glu Arg Pro Tyr Ala
                85                  90                  95

Cys Pro Val Glu Ser Cys Asp Arg His Phe Ser Arg Ser Asp Glu Leu
            100                 105                 110

Thr Arg His Ile Arg Ile His Thr Gly Gly Gln Lys Pro Phe Gln Cys
        115                 120                 125

Arg Ile Cys Met Arg Asn Phe Ser Asp Arg Ser Asn Leu Glu Arg His
    130                 135                 140

Thr Arg Thr His Thr Gly Glu Lys Pro Phe Ala Cys Asp Ile Cys Gly
145                 150                 155                 160

Arg Lys Phe Ala Arg Ser Asp Glu Arg Lys Arg His Thr Lys Ile His
                165                 170                 175

Leu Arg Gln Lys Asp
            180

<210> SEQ ID NO 137
<211> LENGTH: 93
<212> TYPE: PRT
<213> ORGANISM: Artificial Sequence
<220> FEATURE:
<223> OTHER INFORMATION: Description of Artificial Sequence: 3x1F ZIF
      construct
```

<400> SEQUENCE: 137

```
Met Ala Glu Arg Pro Tyr Ala Cys Pro Val Glu Ser Cys Asp Arg Arg
 1               5                  10                  15

Phe Ser Arg Ser Asp Glu Leu Thr Arg His Ile Arg Ile His Thr Gly
             20                  25                  30

Gly Gln Lys Pro Phe Gln Cys Arg Ile Cys Met Arg Asn Phe Ser Arg
         35                  40                  45

Ser Asp His Leu Thr Thr His Ile Arg Thr His Thr Gly Gly Glu Lys
     50                  55                  60

Pro Phe Ala Cys Asp Ile Cys Gly Arg Lys Phe Ala Arg Ser Asp Glu
 65                  70                  75                  80

Arg Lys Arg His Thr Lys Ile His Leu Arg Gln Lys Asp
                 85                  90
```

<210> SEQ ID NO 138
<211> LENGTH: 220
<212> TYPE: PRT
<213> ORGANISM: Artificial Sequence
<220> FEATURE:
<223> OTHER INFORMATION: Description of Artificial Sequence:
      TFIIIA(F1-4)-ZIF fusion construct

<400> SEQUENCE: 138

```
Met Gly Glu Lys Ala Leu Pro Val Val Tyr Lys Arg Tyr Ile Cys Ser
 1               5                  10                  15

Phe Ala Asp Cys Gly Ala Ala Tyr Asn Lys Asn Trp Lys Leu Gln Ala
             20                  25                  30

His Leu Cys Lys His Thr Gly Glu Lys Pro Phe Pro Cys Lys Glu Glu
         35                  40                  45

Gly Cys Glu Lys Gly Phe Thr Ser Leu His His Leu Thr Arg His Ser
     50                  55                  60

Leu Thr His Thr Gly Glu Lys Asn Phe Thr Cys Asp Ser Asp Gly Cys
 65                  70                  75                  80

Asp Leu Arg Phe Thr Thr Lys Ala Asn Met Lys Lys His Phe Asn Arg
                 85                  90                  95

Phe His Asn Ile Lys Ile Cys Val Tyr Val Cys His Phe Glu Asn Cys
            100                 105                 110

Gly Lys Ala Phe Lys Lys His Asn Gln Leu Lys Val His Gln Phe Ser
        115                 120                 125

His Thr Gln Gln Leu Pro Tyr Ala Cys Pro Val Glu Ser Cys Asp Arg
    130                 135                 140

Arg Phe Ser Arg Ser Asp Glu Leu Thr Arg His Ile Arg Ile His Thr
145                 150                 155                 160

Gly Gln Lys Pro Phe Gln Cys Arg Ile Cys Met Arg Asn Phe Ser Arg
                165                 170                 175

Ser Asp His Leu Thr Thr His Ile Arg Thr His Thr Gly Glu Lys Pro
            180                 185                 190

Phe Ala Cys Asp Ile Cys Gly Arg Lys Phe Ala Arg Ser Asp Glu Arg
        195                 200                 205

Lys Arg His Thr Lys Ile His Leu Arg Gln Lys Asp
    210                 215                 220
```

<210> SEQ ID NO 139
<211> LENGTH: 213
<212> TYPE: PRT
<213> ORGANISM: Artificial Sequence

```
<220> FEATURE:
<223> OTHER INFORMATION: Description of Artificial Sequence: GAC-F4-ZIF
      construct

<400> SEQUENCE: 139

Met Ala Glu Arg Pro Tyr Ala Cys Pro Val Glu Ser Cys Asp Arg Arg
 1               5                  10                  15

Phe Ser Arg Ser Asp Glu Leu Thr Arg His Ile Arg Ile His Thr Gly
                20                  25                  30

Gln Lys Pro Phe Gln Cys Arg Ile Cys Met Arg Asn Phe Ser Asp Arg
            35                  40                  45

Ser Asn Leu Glu Arg His Thr Arg Thr His Thr Gly Glu Lys Pro Phe
 50                  55                  60

Ala Cys Asp Ile Cys Gly Arg Lys Phe Ala Arg Ser Asp Glu Arg Lys
 65                  70                  75                  80

Arg His Thr Lys Ile His Leu Arg Gln Lys Asp Asn Ile Lys Ile Cys
                85                  90                  95

Val Tyr Val Cys His Phe Glu Asn Cys Gly Lys Ala Phe Lys Lys His
               100                 105                 110

Asn Gln Leu Lys Val His Gln Phe Ser His Thr Gln Leu Pro Tyr
           115                 120                 125

Ala Cys Pro Val Glu Ser Cys Asp Arg Arg Phe Ser Arg Ser Asp Glu
130                 135                 140

Leu Thr Arg His Ile Arg Ile His Thr Gly Gln Lys Pro Phe Gln Cys
145                 150                 155                 160

Arg Ile Cys Met Arg Asn Phe Ser Arg Ser Asp His Leu Thr Thr His
                165                 170                 175

Ile Arg Thr His Thr Gly Glu Lys Pro Phe Ala Cys Asp Ile Cys Gly
                180                 185                 190

Arg Lys Phe Ala Arg Ser Asp Glu Arg Lys Arg His Thr Lys Ile His
                195                 200                 205

Leu Arg Gln Lys Asp
            210

<210> SEQ ID NO 140
<211> LENGTH: 205
<212> TYPE: PRT
<213> ORGANISM: Artificial Sequence
<220> FEATURE:
<223> OTHER INFORMATION: Description of Artificial Sequence: ZIF-ZnF-GAC
      construct

<400> SEQUENCE: 140

Met Ala Glu Arg Pro Tyr Ala Cys Pro Val Glu Ser Cys Asp Arg Arg
 1               5                  10                  15

Phe Ser Arg Ser Asp Glu Leu Thr Arg His Ile Arg Ile His Thr Gly
                20                  25                  30

Gln Lys Pro Phe Gln Cys Arg Ile Cys Met Arg Asn Phe Ser Arg Ser
            35                  40                  45

Asp His Leu Thr Thr His Ile Arg Thr His Thr Gly Glu Lys Pro Phe
 50                  55                  60

Ala Cys Asp Ile Cys Gly Arg Lys Phe Ala Arg Ser Asp Glu Arg Lys
 65                  70                  75                  80

Arg His Thr Lys Ile His Thr Gly Glu Arg Pro Phe Gln Cys Arg Ile
                85                  90                  95

Cys Met Arg Asn Phe Ser Ser Ser Ser Leu Thr Ser His Ile Arg
               100                 105                 110
```

```
Thr His Thr Gly Glu Arg Pro Tyr Ala Cys Pro Val Glu Ser Cys Asp
        115                 120                 125

Arg Arg Phe Ser Arg Ser Asp Glu Leu Thr Arg His Ile Arg Ile His
    130                 135                 140

Thr Gly Gln Lys Pro Phe Gln Cys Arg Ile Cys Met Arg Asn Phe Ser
145                 150                 155                 160

Asp Arg Ser Asn Leu Glu Arg His Thr Arg Thr His Thr Gly Glu Lys
                165                 170                 175

Pro Phe Ala Cys Asp Ile Cys Gly Arg Lys Phe Ala Arg Ser Asp Glu
            180                 185                 190

Arg Lys Arg His Thr Lys Ile His Leu Arg Gln Lys Asp
        195                 200                 205

<210> SEQ ID NO 141
<211> LENGTH: 534
<212> TYPE: DNA
<213> ORGANISM: Artificial Sequence
<220> FEATURE:
<223> OTHER INFORMATION: Description of Artificial Sequence: 2x3F
      pep11-9 construct

<400> SEQUENCE: 141
atggcggaga ggccctacgc atgccctgtc gagtcctgcg atcgccgctt ttctagcaac      60
caggagctta tacgccatat ccgcatccac accggtcaga agcccttcca gtgtcgaatc     120
tgcatgcgta acttcagtcg cagcgaccac ctgagcaacc acatccgcac ccacacaggc     180
gagaagcctt ttgcctgtga catttgtggg aggaaatttg cccagagcgc cacccgcaca     240
aagcatacca agatacacac gggatctgaa cgcccatatg cttgccctgt cgagtcctgc     300
gatcgccgct tttctcgctc ggatgagctt acccgccata tccgcatcca cacaggccag     360
aagcccttcc agtgtcgaat ctgcatgcgt aacttcagtc gtagtgacca cctgagcgca     420
cacatccgca cccacacagg cgagaagcct tttgcctgtg acatttgtgg gaggaaattt     480
gccgacagca gccaccgcac acggcatacc aagatacacc tgcgccaaaa agat         534

<210> SEQ ID NO 142
<211> LENGTH: 178
<212> TYPE: PRT
<213> ORGANISM: Artificial Sequence
<220> FEATURE:
<223> OTHER INFORMATION: Description of Artificial Sequence: 2x3F
      pep11-9 construct

<400> SEQUENCE: 142

Met Ala Glu Arg Pro Tyr Ala Cys Pro Val Glu Ser Cys Asp Arg Arg
1               5                   10                  15

Phe Ser Ser Asn Gln Glu Leu Ile Arg His Ile Arg Ile His Thr Gly
                20                  25                  30

Gln Lys Pro Phe Gln Cys Arg Ile Cys Met Arg Asn Phe Ser Arg Ser
            35                  40                  45

Asp His Leu Ser Asn His Ile Arg Thr His Thr Gly Glu Lys Pro Phe
        50                  55                  60

Ala Cys Asp Ile Cys Gly Arg Lys Phe Ala Gln Ser Ala Thr Arg Thr
65                  70                  75                  80

Lys His Thr Lys Ile His Thr Gly Ser Glu Arg Pro Tyr Ala Cys Pro
                85                  90                  95

Val Glu Ser Cys Asp Arg Arg Phe Ser Arg Ser Asp Glu Leu Thr Arg
            100                 105                 110
```

```
His Ile Arg Ile His Thr Gly Gln Lys Pro Phe Gln Cys Arg Ile Cys
        115                 120                 125

Met Arg Asn Phe Ser Arg Ser Asp His Leu Ser Ala His Ile Arg Thr
    130                 135                 140

His Thr Gly Glu Lys Pro Phe Ala Cys Asp Ile Cys Gly Arg Lys Phe
145                 150                 155                 160

Ala Asp Ser Ser His Arg Thr Arg His Thr Lys Ile His Leu Arg Gln
                165                 170                 175

Lys Asp

<210> SEQ ID NO 143
<211> LENGTH: 537
<212> TYPE: DNA
<213> ORGANISM: Artificial Sequence
<220> FEATURE:
<223> OTHER INFORMATION: Description of Artificial Sequence: 3x2F
      pep11-9 construct

<400> SEQUENCE: 143
atggcggaga ggccctacgc atgccctgtc gagtcctgcg atcgccgctt ttctagcaac    60
caggagctta tacgccatat ccgcatccac accggtcaga agcccttcca gtgtcgaatc   120
tgcatgcgta acttcagtcg cagcgaccac ctgagcaacc acatccgcac ccacacaggt   180
ggcgagaagc cttttgcctg tgacatttgt gggaggaaat ttgcccagag cgccacccgc   240
acaaagcata ccaagataca cacgggccag cggccgtatg cttgccctgt cgagtcctgc   300
gatcgccgct tttctcgctc ggatgagctt acccgccata tccgcatcca cacaggtggc   360
cagaagccct ccagtgtcg aatctgcatg cgtaacttca gtcgtagtga ccacctgagc   420
gcacacatcc gcaccacac aggcgagaag ccttttgcct gtgacatttg tgggaggaaa   480
tttgccgaca gcagccaccg cacacggcat accaagatac acctgcgcca aaaagat     537

<210> SEQ ID NO 144
<211> LENGTH: 179
<212> TYPE: PRT
<213> ORGANISM: Artificial Sequence
<220> FEATURE:
<223> OTHER INFORMATION: Description of Artificial Sequence: 3x2F
      pep11-9 construct

<400> SEQUENCE: 144

Met Ala Glu Arg Pro Tyr Ala Cys Pro Val Glu Ser Cys Asp Arg Arg
  1               5                  10                  15

Phe Ser Ser Asn Gln Glu Leu Ile Arg His Ile Arg Ile His Thr Gly
                 20                  25                  30

Gln Lys Pro Phe Gln Cys Arg Ile Cys Met Arg Asn Phe Ser Arg Ser
             35                  40                  45

Asp His Leu Ser Asn His Ile Arg Thr His Thr Gly Gly Glu Lys Pro
         50                  55                  60

Phe Ala Cys Asp Ile Cys Gly Arg Lys Phe Ala Gln Ser Ala Thr Arg
 65                  70                  75                  80

Thr Lys His Thr Lys Ile His Thr Gly Gln Arg Pro Tyr Ala Cys Pro
                 85                  90                  95

Val Glu Ser Cys Asp Arg Arg Phe Ser Arg Ser Asp Glu Leu Thr Arg
                100                 105                 110

His Ile Arg Ile His Thr Gly Gly Gln Lys Pro Phe Gln Cys Arg Ile
            115                 120                 125
```

-continued

```
Cys Met Arg Asn Phe Ser Arg Ser Asp His Leu Ser Ala His Ile Arg
    130             135             140
Thr His Thr Gly Glu Lys Pro Phe Ala Cys Asp Ile Cys Gly Arg Lys
145             150             155             160
Phe Ala Asp Ser Ser His Arg Thr Arg His Thr Lys Ile His Leu Arg
            165             170             175
Gln Lys Asp
```

What is clamed is:

1. A nucleic acid encoding a nucleic acid binding polypeptide modified by a method comprising the steps of:
   (a) providing a nucleic acid binding polypeptide comprising a plurality of nucleic acid binding domains;
   (b) selecting a first binding domain comprising no more than first and second zinc fingers, wherein at least one of the zinc fingers of the first binding domain is engineered to bind to a target site;
   (c) selecting a second binding domain comprising no more than first and second zinc fingers, wherein at least one of the zinc fingers of the second binding domain is engineered to bind to a target site; and
   (d) joining the first and second binding domains with a sequence of five or more amino acid residues between the last residue of the alpha helix of the second zinc finger of the first binding domain and the first residue of the beta sheet of the first zinc finger of the second binding domain, wherein the sequence of five or more amino acid residues comprises a sequence selected from the group consisting of GQRP (SEQ ID NO:59), GGEKP (SEQ ID NO:60), GGQKP (SEQ ID NO:61), GGSGEKP (SEQ ID NO:62), GGSGQKP (SEQ ID NO:63), GGSGGSGEKP (SEQ ID NO:64) and GGSGGSGQKP (SEQ ID NO:65).

2. A nucleic acid encoding a non-naturally occurring nucleic acid binding polypeptide comprising a first binding domain joined to a second binding domain, wherein each binding domain comprises no more than first and second zinc fingers; and
   wherein the binding domains are joined by a sequence of five or more amino acids between the last residue of the alpha helix of the second zinc finger of the first binding domain and the first residue of the beta sheet of the first zinc finger of the second binding domain, wherein the sequence of five or more amino acid residues comprises a sequence selected from the group consisting of GQRP (SEQ ID NO:59), GGEKP (SEQ ID NO:60), GGQKP (SEQ ID NO:61), GGSGEKP (SEQ ID NO:62), GGSGQKP (SEQ ID NO:63), GGSGGSGEKP (SEQ ID NO:64) and GGSGGSGQKP (SEQ ID NO:65).

3. The nucleic acid according to claim 2, in which at least one zinc finger is of the $Cys_2$-$His_2$ type.

4. The nucleic acid according to claim 2, in which at least one zinc finger is selected from the group consisting of naturally occurring zinc fingers and consensus zinc fingers.

5. An isolated host cell transformed with a nucleic acid according to claim 2.

6. A pharmaceutical composition comprising a nucleic acid according to claim 2 and a pharmaceutically acceptable carrier.

7. The nucleic acid according to claim 2, wherein, within each binding domain, the first and second zinc fingers are joined by a sequence having a length of four amino acids or less between the last residue of the alpha helix of the first zinc finger and the first residue of the beta sheet of the second zinc finger.

8. The nucleic acid according to claim 2, wherein the polypeptide further comprises a transcriptional repression domain or a transcriptional activation domain.

9. The nucleic acid according to claim 2, further comprising a third binding domain comprising no more than two zinc fingers, wherein the third binding domain is joined to either the first or the second binding domain.

10. The nucleic acid according to claim 9, wherein, within each binding domain, the first and second zinc fingers are joined by a sequence having a length of four amino acids or less between the last residue of the alpha helix of the first zinc finger and the first residue of the beta sheet of the second zinc finger.

11. A nucleic acid encoding a nucleic acid binding polypeptide produced by a method comprising the steps of:
   (a) providing nucleic acid sequences encoding a first nucleic acid binding domain and a second nucleic acid binding domain, each binding domain comprising no more than first and second zinc fingers, wherein at least one of the zinc fingers of each of the first and second binding domains are engineered to bind to a target site; and
   (b) joining the nucleic acid sequences encoding the first and second nucleic acid binding domains with a nucleic acid sequence encoding five or more amino acids between the last residue of the alpha helix of the second zinc finger of the first binding domain and the first residue of the beta sheet of the first zinc finger of the second binding domain, wherein the sequence of five or more amino acid residues comprises a sequence selected from the group consisting of GQRP (SEQ ID NO:59), GGEKP (SEQ ID NO:60), GGQKP (SEQ ID NO:61), GGSGEKP (SEQ ID NO:62), GGSGQKP (SEQ ID NO:63), GGSGGSGEKP (SEQ ID NO:64) and GGSGGSGQKP (SEQ ID NO:65).

* * * * *